United States Patent [19]
Joao

[11] Patent Number: 5,961,332
[45] Date of Patent: Oct. 5, 1999

[54] APPARATUS FOR PROCESSING PSYCHOLOGICAL DATA AND METHOD OF USE THEREOF

[76] Inventor: Raymond Anthony Joao, 122 Bellevue Pl., Yonkers, N.Y. 10703

[21] Appl. No.: 08/600,771

[22] Filed: Feb. 13, 1996

Related U.S. Application Data

[62] Division of application No. 08/941,413, Sep. 8, 1992, abandoned.

[51] Int. Cl.[6] .................................................... G09B 19/00
[52] U.S. Cl. ........................... 434/236; 434/238; 128/923
[58] Field of Search .................................... 434/236–238; 128/920, 923

[56] References Cited

U.S. PATENT DOCUMENTS

| | | |
|---|---|---|
| 4,895,518 | 1/1990 | Arnold et al. . |
| 5,070,452 | 12/1991 | Doyle, Jr. et al. . |
| 5,185,857 | 2/1993 | Rozmanith et al. . |
| 5,217,379 | 6/1993 | Kirschenbaum et al. . |
| 5,219,322 | 6/1993 | Weathers . |
| 5,435,324 | 7/1995 | Brill . |

OTHER PUBLICATIONS

"The Development Of A Microcomputer–Based Mental Health Information System, A Potential Tool For Bridging the Scientist–Practioner Gap", L. McCullough et al., *American Psychologist*, Feb. 1986, pp. 207–213.

*Primary Examiner*—Richard J. Apley
*Assistant Examiner*—Glenn Richman
*Attorney, Agent, or Firm*—Raymond A. Joao

[57] ABSTRACT

An improvement to an apparatus for processing psychological data, said apparatus comprising means for processing data indicative of at least one of an individual's psychological condition, psychological states, concomitant physiological states, and states of dysfunction in conjunction with at least one of psychological, concomitant physiological, and psycho pathological, at least one of principles, theories and research data in order to generate data indicative of at least one of a diagnosis and a treatment plan for the individual, the improvement comprising a remote user interactive means for providing at least one of a remote accessing and utilization of said apparatus, said remote user interactive means further comprising a user input means for inputting data pertaining to an individual and a user display means for providing at least one of an indication of apparatus operation and data relevant to an individual, wherein said remote user interactive means facilitates at least one of data entry and control over said apparatus, and further wherein data pertinent to at least one of an individual's diagnosis and treatment plan is obtained from said apparatus via said remote user interactive means. A method of use of the improved apparatus is also disclosed.

20 Claims, 20 Drawing Sheets

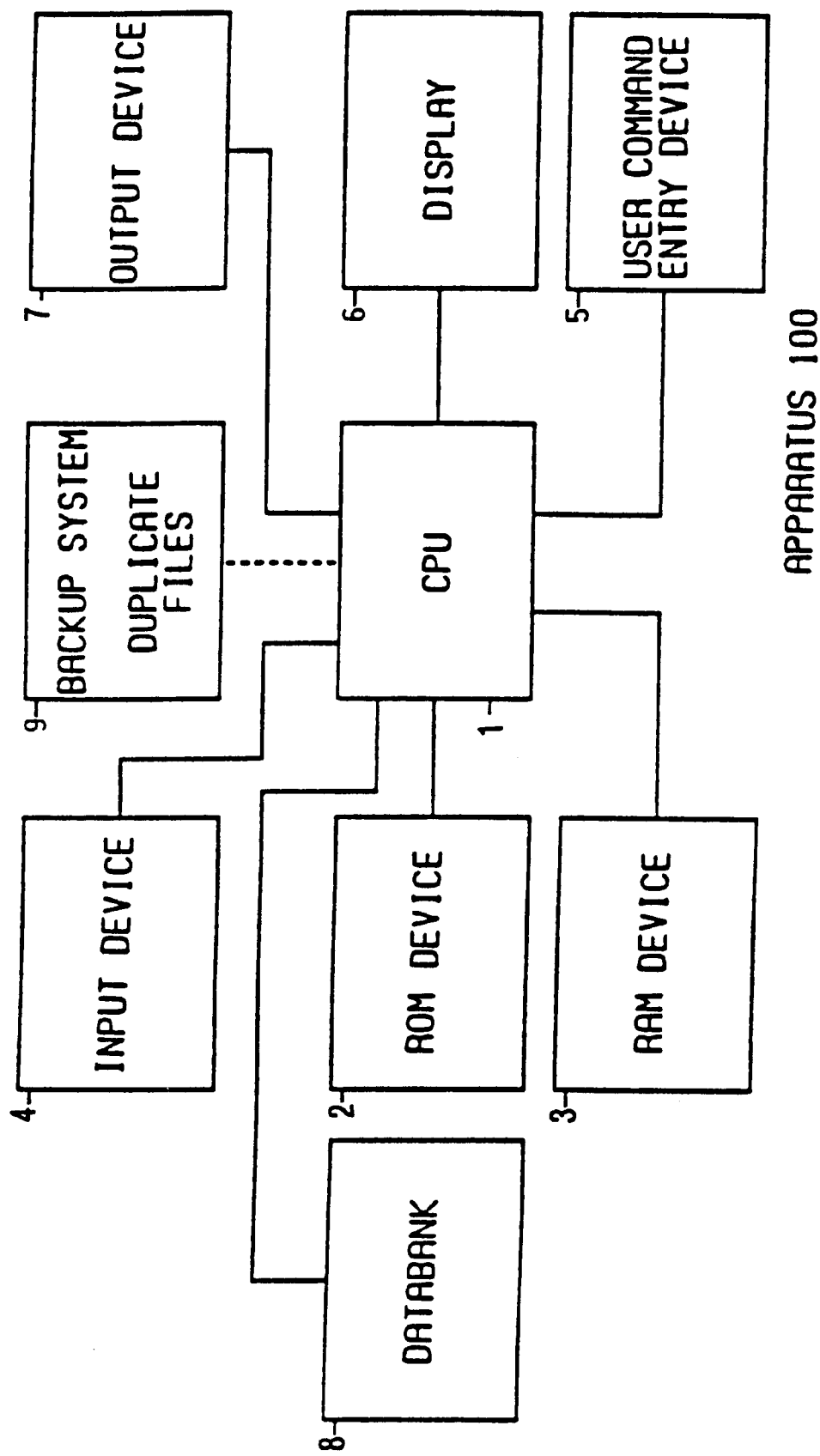

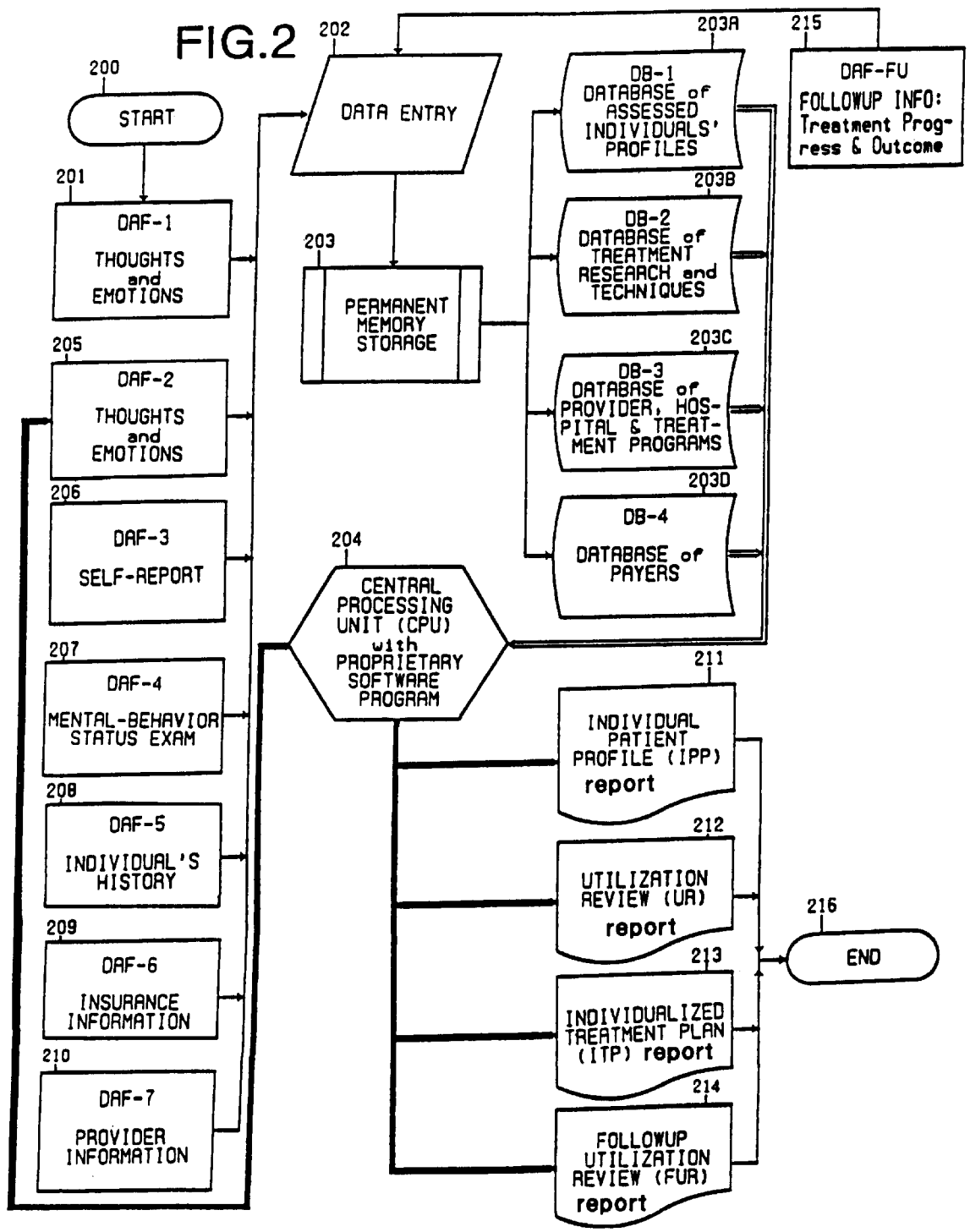

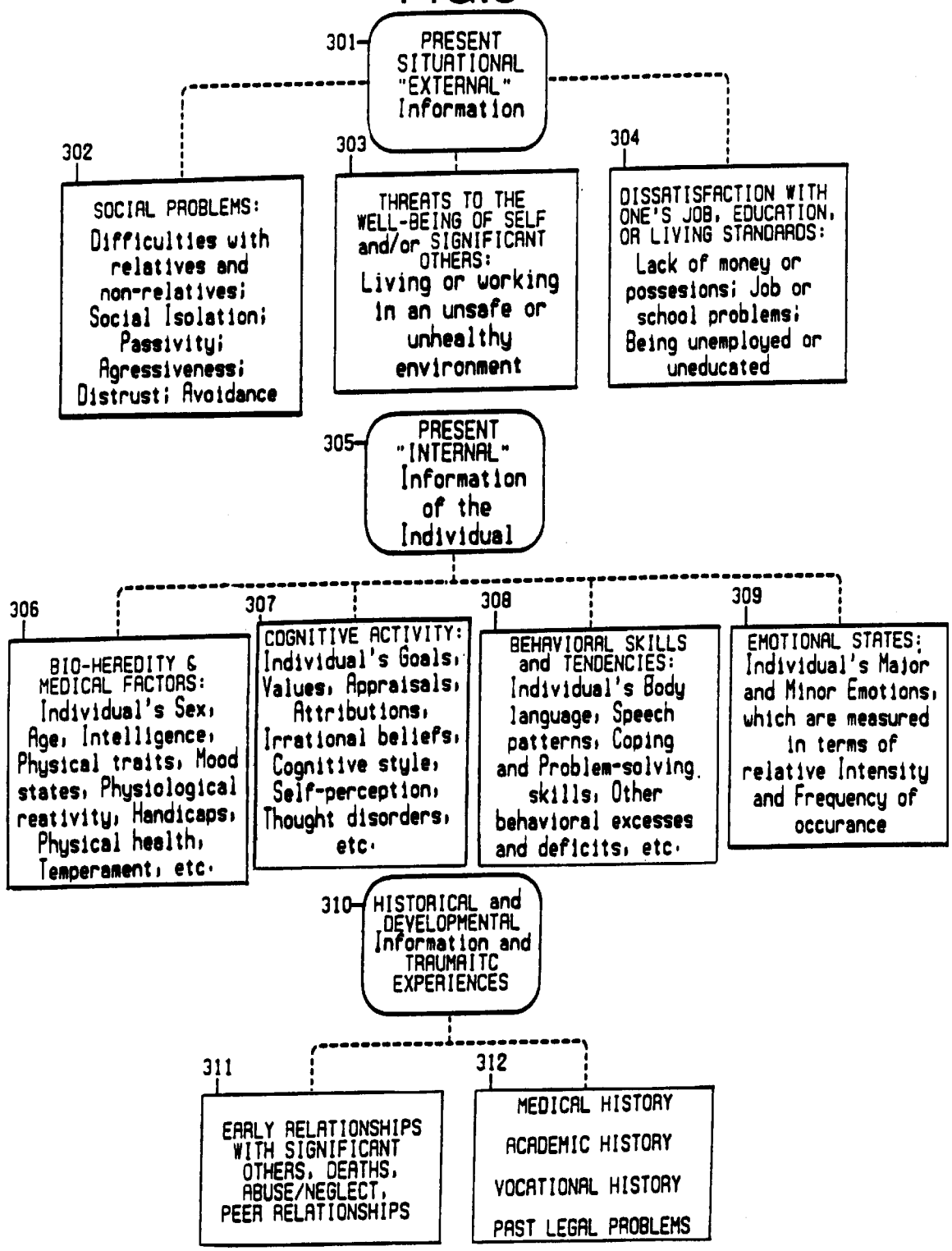

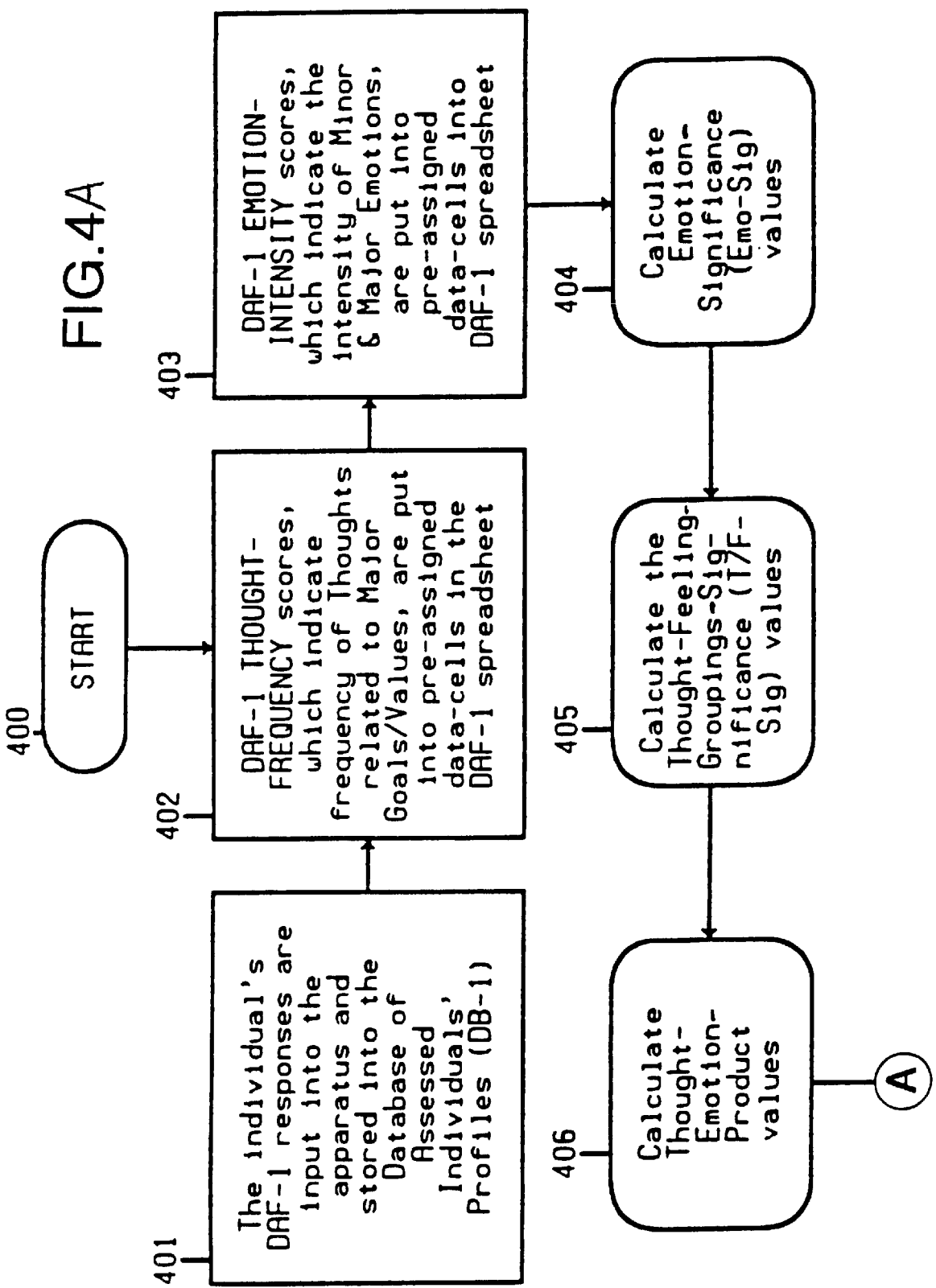

COST-EFFECTIVE PSYCHOTHERAPY & PSYCHOPHARMACOLOGY OPTIONS

1405

PSYCHOTHERAPY TYPES

| Type I | Type II | Type III | Type IV | Type V |
|---|---|---|---|---|
| Relaxation Training | Cognitive-Behavioral Ther. | Person-centered Ther. | Psychoanalysis | Family Systems Restructuring |
| Behavior Modification | Rational-Emotive Therapy | Adlerian Therapy | Existential Therapy | |
| Overt Conditioning | Reality Therapy | Personal Construct Ther. | Logo Therapy | Type VI |
| Assertion Training | Gestalt Therapy | Ego Analysis | | Hypnosis |
| Biofeedback | Social Skills/Communication | | | |

Tx DURATION: Average treatment time required for patients with similar initial score to improve to a score of [ ] or below. 1409

1410  a=<5; b=5-9; c=10-14; d=15-19; e=20-24; f=25-29; g=30-34; h=35-39; i=40-44; j=45-49; k=50-54; L=55-59; m=60+

Tx MODE:
A = Individual Outpatient Psychotherapy (Duration in Outpatient-Hours)
B = Couples/Marital Outpatient Psychotherapy (Duration in Outpatient-Hours)
C = Family Outpatient Psychotherapy (Duration in Outpatient-Hours)
D = Group Outpatient Psychotherapy (Duration in Outpatient-Hours)
E = Inpatient Treatment (Duration in Weeks of Hospitalization)
1407

PSYCHOPHARMACOLOGY:
1 = Antidepressant
2 = Antipsychotics (Neuroleptics)
3 = Anxiolytic Agents
4 = Hypnotics/Sedatives
5 = Mood Stabilizers
6 = Psychostimulants
7 = Sex-Drive Depressants
8 = Anti-Alcohol Drugs
1412

OTHER: 1414
I = Physical Health/Exercise/Eating Program
II = Self-Help Group (Adjunct to Psychotherapy)
III = HOSPITALIZATION if Immanently Suicidal

---

ID No.  228567A
Date:   3/8/92

30 = AGE (in years)
FEMALE = SEX
7 = INTELLIGENCE
7 = VERBAL EXPRESSIVENESS 118-5229  Provider's ID Number

INITIAL ASSESSMENT

1400
SEVERITY SCALE: 1—2—3—4—5—6—7—8—9—10
LOW          MODERATE          HIGH

APPARATUS FOR PROCESSING PSYCHOLOGICAL DATA AND METHOD OF USE THEREOF

This is a divisional application of Ser. No. 07/941,413, filed Sep. 8, 1992, now abandoned.

1. FIELD OF THE INVENTION

The present invention relates to the field of mental health care and pertains to a method and an apparatus for the acquisition, accumulation, analysis and application of psychological and/or psychopathological data and/or other pertinent information. The present invention provides for an objective and scientific method and apparatus by which to acquire and analyze psychological and/or psychopathological data which data operationally defines the severity of an assessed individual's psychological state and/or state of dysfunction. The data obtained therefrom is utilized to objectively determine the most cost-effective and optimum quality mental health care treatment methods, techniques, approaches, programs, and/or facilities available to the mental health care patient. The method and apparatus of the present invention also systematically assesses the progress, process and outcome of the psychological treatment prescribed and/or administered for and to the patient.

2. BACKGROUND OF THE INVENTION

The incidence and frequency of mental health care has grown to such an extent that mental health care costs now exceed 30 billion dollars annually. While technologies have been developed in other areas of health care to help meet the growing needs for cost-containment and quality control, no technology presently exists which is capable of meeting the growing demands for cost-containment and quality control in the growing mental health care field and industry. In particular, no technology presently exists which utilizes and relies upon a method and an apparatus for the systematic acquisition of objective psychological and/or psychopathological data and/or other pertinent information which utilizes the logical and statistical analysis of such data in order to measure and operationally define the nature and severity of an individual's psychological state and/or state of dysfunction so as to produce output data which can be utilized to indicate and to prescribe the most cost-effective and optimum quality treatment methods, techniques, approaches, programs, and/or facilities available for the treatment of an individual's psychological illness or state of dysfunction. Further, no technology exists which also provides a means by which to monitor the progress, process and outcome of these psychological treatments.

In the prior art, psychological tests are known such as the *Minnesota Multiphasic Personality Inventory* (MMPI) test, the *California Psychological Inventory* (CPI) test, and the *Sixteen Personality Factor Questionnaire* (16PF). While these known prior art tests objectively determine the personality types and traits of an individual, they fail to provide a means by which to measure the specific psychological information which may be utilized in order to objectively determine treatment planning, progress, outcome, cost effectiveness, and/or quality control.

In the prior art publications, the *Diagnostic and Statistical Manual of Mental Disorders* (DSM-III-R), published by the American Psychiatric Association, and the *International Classification of Diseases* (ICD-9), developed by the World Health Organization, the descriptions of symptoms are divided into diagnostic categories. These publications, however, have been widely criticized for being fraught with vague and/or arbitrary diagnostic criteria which tend to have little relevance to treatment planning or to the measurement of treatment progress, process or outcomes.

Automated treatment plan generators such as *TPWrite*, published by Reason House, LTD., are also known from the prior art, which utilize data such as that obtained from the above described DSM-III-R publication schemes in order to determine diagnosis, treatment type, treatment goals and estimated duration of treatment, which data and criteria are subjectively determined by the mental health care health care professional, practitioner and or facility (i.e., the psychologist, psychiatrist, social worker, psychiatric nurse, counselor, psychiatric hospital, mental health clinic, substance abuse program, etc.), hereinafter designated the "provider", in order to generate and/or to produce results in the form of computer-generated reports. These automated treatment plan generators, however, lack the scientific data, and the means by which to provide the statistical analysis of such data, which is necessary in order to measure and operationally define the nature and severity of an individual's psychological state and/or state of dysfunction. Further, these known automated treatment plan generators do not provide for the generation of reports which determine the optimum and the most cost-effective treatment methods, techniques, approaches, programs, and/or facilities available to the assessed individual. Further, the treatment generators do not provide for the monitoring of the progress, process and outcome of these treatment methods, techniques, approaches, programs, and/or facilities.

Various other mental health care publications are also known from the prior art which describe psychological treatment alternatives for treating a multitude of psychological disorders. These publications, however, have oftentimes been found to provide contradictory information with regards to treatment options which result from the lack of, or absence of, a sufficient amount of valid, coordinated and integrated mental health care treatment outcome and treatment process research upon which to base conclusions.

The above described shortfalls in the prior art result from the absence of a method and an apparatus, in the mental health care field, which may be utilized consistently and efficiently in the acquisition, accumulation, analysis and application of psychological and/or psychopathological data and/or other pertinent information along with the treatment outcome and process data which relates thereto. The present invention provides a method and an apparatus which serve to overcome the shortfalls of the prior art.

SUMMARY OF THE INVENTION

The method and apparatus of the present invention provide a means by which to overcome the shortfalls inherent in the mental health care field and industry by providing a method and apparatus for providing an objective and scientific method and apparatus by which to acquire, accumulate, analyze and apply psychological and/or psychopathological data and/or other pertinent information as well as psychological treatment outcome and process data, in order to operationally define the nature and degree of severity of an individual's psychological state and/or state of dysfunction. Further, the method and apparatus of the present invention utilizes the data obtained therefrom to objectively determine the optimum and the most cost-effective mental health care treatment options which are available to the assessed individual if such treatment is deemed appropriate. The method and apparatus of the present invention further provides a means by which to systematically assess the progress, process and outcome of the psychological treatment programs, methods, approaches and/or techniques which are prescribed.

The apparatus of the present invention comprises a digital computer system which comprises a Central Processing Unit (CPU). The CPU is utilized for processing the input data obtained during the course of the psychological evaluation methods and processes, which are utilized in the method of the present invention, and for performing various calculations and/or data processing routines which are also utilized in the method of the present invention. The digital computer system generates output data which is indicative of the specific information which indicates and/or models an individual's psychological state and/or state of dysfunction, the severity of the individual's psychological state and/or state of dysfunction, and the most cost-effective and optimum quality mental health care treatment methods, techniques, approaches, programs, and/or facilities available for the treatment of the assessed individual should such treatment be deemed appropriate. The CPU may be a microprocessor, a microcomputer, a macrocomputer or a mainframe computer depending upon the digital computer system utilized, which operates under software control. The method of the present invention may be implemented by computer programs and/or software programs and/or algorithms.

The apparatus also comprises a Read Only Memory (ROM) device for the storage of the software program or operational program data which controls the CPU in the operation of the method utilized in the present invention. A Random Access Memory device (RAM) is also utilized for the storage of the psychological and/or psychopathological data as well as the data which is utilized in the processing of the psychological and/or psychopathological data and/or other pertinent information. An input data device is also utilized for entering data into, and for facilitating the control of, the digital computer system. The apparatus also comprises a user display device which is utilized for displaying information related to the operation of the method and apparatus of the present invention. Further, the user display device provides a means by which to select, on-screen, various operations and/or controls over the digital computer system. The apparatus of the present invention further comprises a data output device for generating and/or for transmitting electronically output data which is generated by the digital computer system.

A memory storage bank or databank is also employed for storing and maintaining current databases of psychological profiles, the data of which may be updated continuously such as by the entry of data of a new assessed individual, revised data of an assessed individual, or other data necessary for the utilization of the present invention. The databank is utilized in order to store data which will provide a continuously updated and ever-increasing memory store of data and statistical information which will be utilized by the present invention. The apparatus may also comprise a backup system which comprises a backup CPU, a ROM device and a RAM device which serve as a redundancy system in the event of a failure or malfunction of the respective primary system counterparts.

The apparatus may also comprise a user interactive interface and delivery device which may be designed to be located at remote locations such as at locations of providers, the companies which pay for mental health care treatment (i.e., managed health care companies, traditional indemnity health insurance companies, self-insured companies, utilization review firms, etc.), hereinafter designated the "payers", as well as other customers, and/or subscribers, and which may be interfaced with the apparatus of the present invention either via telecommunication networks, radio transmitters and/or by any one of a number of communication systems.

The user interface and delivery device, which may be provided to a user at a remote location, may provide a means by which to allow a provider, a payer, and/or other customers or subscribers to access the apparatus in order to allow for a direct transmission of data and information to the apparatus and which allow for an instantaneous processing of the data and information so as to expeditiously enter data or information into the apparatus and obtain processed output data therefrom.

Output data reports may also be delivered via such an interactive user interface and delivery device. The interactive user interface and delivery device may also store data or information particular to the needs of the user (i.e., patient records with provisions being made for maintaining secrecy confidentiality and anonymity). The interactive user interface and delivery device may also be employed to access designated data from unsecured databases, or portions thereof, which may be stored in the apparatus in order to facilitate an on-line database of psychological and/or psychopathological data and information. Also, numerous processing channels may be provided in order to facilitate use of the present invention by multiple users in a network environment. Such a network may be facilitated by any one of a number of communication systems or link-ups which may include telephone communication lines, radio transmitters and satellite communication link-ups, etc.

Further, data may be transmitted via the user interactive interface and delivery device in order to facilitate the complete operation of the present invention. Any information pertaining to input data and/or output data can be electronically transmitted by the user interactive interface and delivery device wherein it may be output via an output means, which may be a printer, or it may be stored in a permanent memory or database located in the device.

The utilization of the user interactive interface and delivery device may be accessed by the specific provider, payer and/or other customers and subscribers by use of a password or access code or via any other security means so as to provide for the maintenance of information, security and confidentiality. The user interactive interface and delivery device may also facilitate the management of information files for numerous individuals so that the provider, payer and/or other customers or subscribers may have these files for its assessed individuals stored in the device at its location. This will provide for easy access of such data and may facilitate more efficient record keeping.

The present invention is premised upon a user interactive scheme wherein data obtained, which is representative of a predetermined assortment of psychological and/or psychopathological data and/or other pertinent information, is input into the apparatus during various stages of data entry. The method and apparatus of the present invention processes this data and information so as to provide intermediate and final output data or reports.

The method of the present invention comprises the obtaining of psychological and/or psychopathological data and/or other pertinent information from the individual; his or her mental health care provider and the payer of his or her mental health care treatment. This data or information is obtained such as by illiciting the responses to predetermined questions found in one or more questionnaires or forms. The questionnaires or forms are specifically designed for use with the present invention. Each questionnaire or form comprises a series of questions which are designed to measure various types of psychological information which are indicative of numerous and various psychological states and/or states of dysfunction (i.e., psychopathology) and/or other pertinent information.

The questionnaires or forms are utilized to illicit data indicative of present situational data which pertain to "external" influences including social problems, threats to the well-being of one's self and/or significant others, and dissatisfaction with one's job, education, or standard of living. The questionnaires or forms are also utilized in order to illicit data which pertains to present "internal" influences including bio-hereditary and medical information, cognitive activity, and the connection between one's thoughts and feelings, and one's behavioral skills and tendencies.

Significant historical and developmental information and traumatic early experiences of an individual may also be assessed, including early relationships with significant others, deaths, an individual's being abused or neglected, and peer relationships, along with an individual's medical, academic, vocational, and legal history.

The data obtained is combined or aggregated to provide information specifically designed for use with the present invention. The data obtained may be assigned in an array or matrix-like database or data structure, such as a spreadsheet, wherein the data is assigned locations, within the matrix-like database or spreadsheet, so as to correspond to specific psychological constructs and diagnostic criteria. These data groupings are derived through a rational and logical review and analysis of the data with respect to psychological principles and theories. The data may also be derived via statistical analysis. The data groupings may be subsequently confirmed or modified as determined by statistical procedures such as by factor analysis.

The method of the present invention may be initiated by administering a first questionnaire or form, to the assessed individual with the assessed individual's responses being recorded. The first questionnaire or form may comprise questions designed to measure the relationship between the assessed individual's thoughts and emotions which are also designed to measure data which pertains to major desired goals and/or difficulties experienced pertaining thereto.

The data and information obtained is then sent via the mail or electronically via a modem to a central processing center where the data is entered into, and stored within, the apparatus.

The method and apparatus of the present invention utilizes the data and information, acquired via the first question or form, along with theoretical and research-based psychological and/or psychopathological data and information. The processing of the data and information may be accomplished using computer programming schemes and data structures as well as by using spreadsheet software and technologies.

The data and information obtained, as well as any additional data and information obtained therefrom, may be stored within the apparatus. The data and information may then undergo a series of mathematical calculations which compute a series of data values which are computed by formulas which may also be stored within the apparatus. The formulas instruct the CPU to perform various calculations and data processing routines upon the data being processed in order to produce a second questionnaire or form which may be obtained from the first questionnaire or form, or set thereof. By providing a means by which to customize a subsequent questionnaire or form according to the responses from a prior questionnaire or form administration time can be minimized while efficiency can be maximized by the elimination of a further assessment of psychological information which may be deemed to be non-significant, or of no value, in or to, the continued assessment or treatment of the individual.

The second questionnaire or form along with any remaining questionnaires or forms may then be administered to the assessed individual for obtaining further individual data. The second questionnaires or forms may then be administered to the individual in order to obtain the balance of the data or information needed for performing the method of the present invention. Open-ended questions may also be provided in the questionnaires or forms which may be utilized to provide supplemental information which may be useful in the assessment and treatment of the individual. The second questionnaire or form may comprise questions which are designed to assess the attributions, appraisals and irrational beliefs of the individual. The assessed individual's endorsement of the attributions, appraisals and irrational beliefs are measured by the individual's responses to the second questionnaire or form.

The administration of open-ended questions, which may be optional, may be useful since these questions provide an opportunity for the assessed individual to elaborate upon limited format questions (e.g., true-false questions). While the responses to the open-ended questions may not be utilized in the method of data processing of the present invention, system processing, they may be utilized by the health care provider in analyzing the assessed individual's condition in conjunction with the output data reports obtained from the present invention. The data from the second questionnaire or form is also stored within the apparatus.

The questions which may comprise a third questionnaire or form may be designed to assess self-reported information which pertain to the assessed individual's background, family dynamics, medical and physical illnesses, problems and symptoms, existing psychological problems and symptoms, history of psychological treatment, medications being taken, current environmental stressors, and the outcome of coping attempts. Once obtained, this data is also stored within the apparatus.

The questions which may comprise a fourth questionnaire or form may be designed to obtain the provider-reported assessment of information concerning the assessed individual's physical and psychological symptoms, including information which may overlap with the assessed individual's self-reported responses. In addition, information may be obtained pertinent to the treatment methods, techniques, approaches, programs, and/or facilities utilized by the provider in treating the individual, as well as other pertinent treatment information. Once obtained, this data is also stored within the apparatus.

The questions which comprise a fifth questionnaire or form may be designed to obtain information pertaining to an assessed individual's past including the assessed individual's early relationships with significant others and critical childhood experiences. This data is also stored within the apparatus.

The questions which may comprise a sixth questionnaire or form may be designed to obtain information relating to payers of mental health care treatment. This information may include an assessed individual's medical and psychological history, the payer's payment schedules or reimbursement rates, and previous payments made to the assessed individual's health care provider. This data is also stored within the apparatus.

The questions which may comprise a seventh questionnaire or form may be designed to obtain information pertaining to the assessed individual's mental health care provider including the provider's age, sex, area of licensure, address, phone number, areas of treatment expertise, and the treatment methods, techniques, and/or approaches the provider is skilled at utilizing, as well as other pertinent treatment information. utilized, medications administered, and the name of the facility wherein the assessed individual may be, or may have been, hospitalized or in a treatment program where he or she may be, or may have been enrolled, such as in a drug treatment center. In addition, questions pertaining to the provider's choice of treatment technique, method, and approaches to be utilized in treating the assessed individual are included. This data is also stored within the apparatus.

A follow-up questionnaire or form may also be utilized depending upon an individual's stage of mental health care treatment and upon the request of the payer or provider. The questions which may comprise the follow-up questionnaire or form may be designed to obtain information from both the assessed individual and the individual's mental health care provider about changes which may have occurred in the previously assessed psychological information representative of the individual's psychological state or state of dysfunction during the course of treatment. Changes in the severity of the components of an assessed individual's condition may result in changes in suggested treatment methods and modes of treatment delivery as well as indicate treatment progress, process and/or outcome. This data may also be stored within the apparatus.

The questionnaires or forms described above, provide a means by which to obtain vital information from the assessed individual, the health care provider and the payer. It should be noted that the specific questions and response possibilities may be subject to modification and revision so as to incorporate future developments in the use and application of the present invention as well as to incorporate future developments in the mental health care field or industry.

Once all of the data and information which may be utilized from the questionnaires or forms have been entered into and stored within the apparatus, the apparatus performs one or more of a series of processing routines which result in data which may be utilized in order to generate a series of reports which may then be utilized by the health care providers as well as by the payers.

The generation of the above mentioned reports may be partially dependent upon accessing data and information which is or may be stored within various databases. A first database may include data representative of an assessed individual's responses to the questionnaires or forms, or sets thereof. A second database may include an exhaustive survey of the findings of psychotherapy research process and outcome studies and theoretical information pertaining to the use of specific treatment techniques, methods and approaches. It may also include information regarding the matching of treatment type, mode, and duration to an assessed individual's particular psychological needs. A third database may include pertinent information about the mental health care providers including identification data, areas of expertise, and the treatment methods employed. A fourth database may include information pertaining to the mental health care payers.

The method and apparatus of the present invention performs various processing routines upon the data obtained from the questionnaires or forms along with the information stored in the various other databases, described above, in order to perform an analysis and diagnosis of an individual's psychological state and/or state of dysfunction. Further, the method and apparatus of the present invention provides a means by which to provide a monitoring and an assessment of the progress, process and outcome of the individual's treatment. The processing routines utilized comprise numerous calculation and comparison routines which are performed upon the data and information obtained and stored within the apparatus. This data and information may be processed in conjunction with psychological principles and theories, research data, and/or other pertinent information stored within the apparatus. The results of the processing routines may then be provided in one or more of a series of reports which are generated by the present invention.

A first report may describe the assessed individual's psychological profile in terms of precise and treatment-relevant objective measurements. From these measurements, data may be obtained which is utilized in order to determine the degree of the assessed individual's emotional discomfort, distorted or dysfunctional thinking, and maladaptive behavior. This data may be statistically determined in order to facilitate comparison with other individuals.

The first report may also include a summary and analysis of the assessed individual's bio-medical condition, the assessed individual's cognitive, emotional and behavioral tendencies as they relate to different situations, the assessed individual's current environmental and social stressors he experiences, and the assessed individual's significant historical and/or childhood data and other diagnostically relevant information. Further, the second report may also be capable of determining the degree of likelihood that the assessed individual and/or the provider are answering the pertinent questions accurately and honestly.

A second report may also be generated which may be sent to the payers of mental health care. The second report is designed to assist payers in determining the most cost-effective treatment type and mode of delivery. Also included in the second report is an assessment of the probable length of time which would be necessary in order to realize a multitude of treatment goals (i.e., treatment duration). The provider and/or the payer may also request that certain data and/or constraints be utilized in the data analysis of the present invention. The present invention may also be utilized to make determinations regarding the type, the mode, and the duration and frequency of treatment by matching the particular aspects of the assessed individual's state of dysfunction with information stored within the apparatus.

The second report may also include information useful in matching a provider's characteristics to an assessed individual's needs. Criteria such as the provider's areas of specialty care, treatment skills, experience, and treatment history with similar types of patients may also be included in the report so as to indicate an accurate and effective provider to patient match. Further, the second report may also be capable of determining the degree of likelihood that the assessed individual and/or the provider are answering the pertinent questions accurately and honestly.

A third report may provide a detailed treatment plan, including a list of treatment goals and suggestions as to which treatment methods, techniques or approaches (including specific types of psychotherapy and psychopharmacology-medication) are likely to be the most cost-effective in treating each aspect of the assessed individual's psychological state of dysfunction. In addition, the third report may list references to the specific research findings upon which the various treatment goals and suggestions may have been based. The choice of the actual treatment plan format may be based upon the provider's and/or the payer's specific needs and/or requests.

Follow-up assessments may be obtained by utilizing the follow-up questionnaires or forms. Following the software processing of the information obtained therefrom, a fourth report may be produced. By administering the follow-up questionnaire or form at various time intervals, the progress, process and outcome of a treatment may be determined and reported in this report. The fourth report may indicate changes in the assessed individual's state or state of dysfunction, the amount of treatment time remaining, modifications to treatment and the cumulative cost of the treatment.

The wealth of psychological and/or psychopathological data and/or other pertinent information accumulated by and stored within the apparatus of the present invention may also be analyzed and utilized in such a manner so as to yield vital actuarial data which may be made available to the payers of mental health care for actuarial purposes. Further, the objective data provided by the present invention may be made available for use in numerous fields including the fields of law, biomedicine, psychology, psychiatry, and government. Utilization of the above data in research, decision-making and litigation are also envisioned. All such analyses, may be normative, meaning, based upon the analyses of groups of data therefore enabling sophisticated statistical analyses of such data as well as maintaining an assessed individual's confidentiality and anonymity thereby.

Accordingly, it is an object of the present invention to provide a method and an apparatus for the acquisition, accumulation, analysis and application of psychological data and/or other pertinent information.

It is another object of the present invention to provide a method and an apparatus for psychological treatment which provides a means by which to measure the specific psychological information upon which to objectively determine treatment planning, progress, process, outcome, cost effectiveness, and/or quality control in the mental health care field.

It is another object of the present invention to provide a method and an apparatus for acquiring, accumulating and processing scientific data, research data, and/or other pertinent data or information, and for performing statistical analysis upon such data, which is necessary in order to measure and operationally define the nature and severity of an assessed individual's psychological state and/or state of dysfunction.

It is yet another object of the present invention to provide a method and an apparatus for the generation of reports which are indicative of an assessed individual's psychological state and/or state of dysfunction and diagnoses along with the optimum and most cost-effective treatments, treatment methods, techniques, approaches, programs, and/or facilities available to the assessed individual, along with monitoring and reporting data and information indicative of the progress, process, and outcome of the treatment provided.

Still another object of the present invention is to provide a method and an apparatus for gathering research data relevant to mental health care treatment in a manner which enables various individuals, entities and organization in the mental health care field and industry to coordinate their research programs and utilize and apply the research findings thereof to maximize the quality and cost-effectiveness of mental health care treatment.

Other objects and advantages of the present invention will be made apparent to those persons skilled in the art upon a review of the Description of the Preferred Embodiment taken in conjunction with the Drawings which follow.

BRIEF DESCRIPTION OF THE DRAWINGS

In the Drawings:

FIG. 1 illustrates a Block diagram of the apparatus of the present invention;

FIG. 2 illustrates an overall functional Block diagram of the operational Steps of the method utilized in the present invention;

FIG. 3 illustrates the data or information groups which are assessed by the method and apparatus of the present invention in a structured diagrammatical format;

DESCRIPTION OF THE PREFERRED EMBODIMENT

Figure 3A:
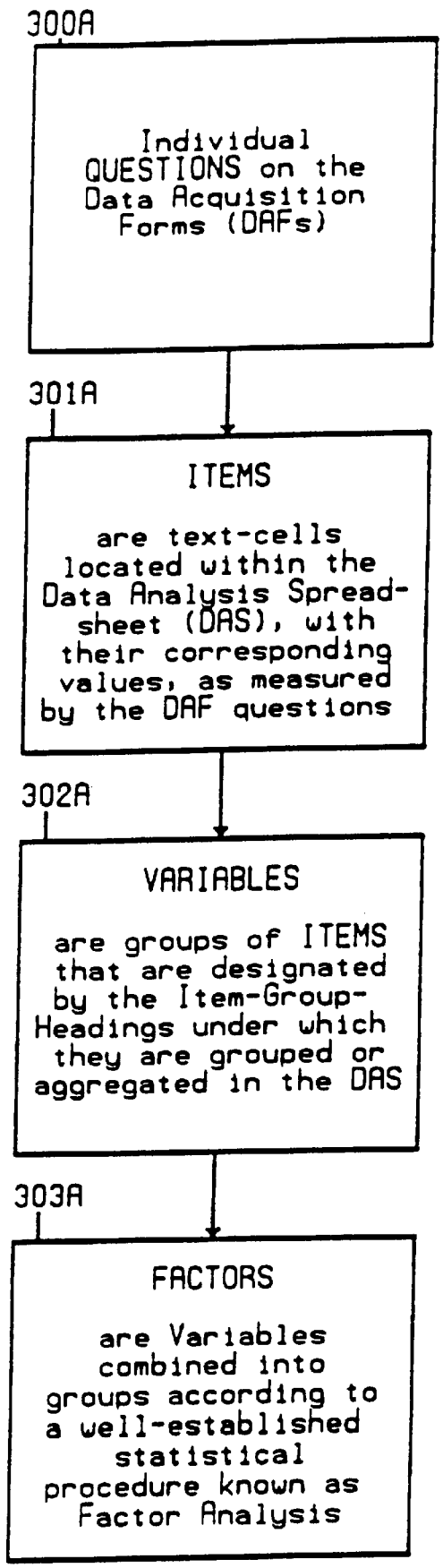
FIG. 3A illustrates the aggregation or combination of input data items utilized by the method and apparatus of the present invention, in a structured diagrammatical format.

FIG. 1 illustrates a block diagram of the apparatus of the present invention which is denoted generally by the reference numeral 100. The apparatus of the present invention comprises a Central Processing Unit (CPU) 1 which is utilized for processing the input data obtained during the course of the psychological assessment methods and processes, as well as data obtained at other times, which will be described in more detail below, and for providing various calculations and data processing routines with and upon this data, in order to generate output data results which are indicative of an individual's psychological state and/or state of dysfunction, the severity of the individual's psychological state and/or state of dysfunction, and the most cost-effective and optimum quality mental health care treatment programs, methods and/or techniques available for the treatment of the individual's psychological state and/or state of dysfunction. The CPU 1 may be a microprocessor, a microcomputer, a macrocomputer or a mainframe computer system depending upon the application and the digital computer system employed.

The apparatus 100 also comprises a Read Only Memory (ROM) device 2 for the storage of the operational program data or codes which control the operation of the apparatus 100 and which further comprises any additional software programs or codes which direct the apparatus 100 to perform the method utilized in the present invention. In this manner, the method of the present invention may be embodied solely as a computer and/or software program or codes. A Random Access Memory (RAM) device 3 is also utilized for storing the data which is utilized in the processing of the psychological data and/or psychopathological data and/or other pertinent information which will be described in more detail below. A data input device 4, which may be a keyboard, a modem, an optical scanner, or any other suitable means for entering data into a digital computer system, is also utilized in the apparatus 100 as well as a user command entry device 5 which may also be a keyboard, a mouse, or any other suitable means by which to facilitate the entry of user control commands and/or the entry of data into a digital computer system. The apparatus 100 also comprises a user display device 6 for displaying information related to the operation of the present invention. In this respect, the operation of the apparatus 100 may be facilitated by the display of on-screen menus which may allow a user, via the user command entry device 5, to select apparatus operation or in other ways exert control over the present invention.

The apparatus 100 further comprises an output device 7 which may be or which may include a printer, for generating output data such as hard copy reports or other suitable printed matter, or a modem or other suitable telecommunication means, for transmitting electronically output data or report data which may then be transmitted to remote locations.

A databank 8 is also employed for maintaining current databases of psychological profiles, and other data which may be utilized by the present invention, which will be described in more detail below, the data of which may be updated continuously such as by the entry of new data or revised data. The databank 8 is utilized in order to store data which may provide a continuously updated and ever-increasing memory store or databank of databases which can be utilized to store the various data and statistical information which may be utilized by the present invention. In this manner, and in conjunction with statistical analysis methods, a more meaningful assessment may be made based upon the general population.

The apparatus 100 may also comprise a backup system 9 which comprises a CPU 1', a ROM device 2' and a RAM device 3', which are identical to the CPU 1, the RAM device 2 and the ROM device 3, respectively, described above. The backup system 9 serves as a redundancy system in the event of a failure or malfunction of any of their primary system counterparts (CPU 1, ROM device 2 and RAM device 3, respectively). In this manner, duplicate files may be stored. Further, the database 8 may also have, corresponding thereto, various back-up systems or devices.

The CPU 1 of apparatus 100 operates under the control of the system operational software data which is stored in the ROM device 2 memory device. The operational software of the apparatus 100, as will be described in more detail below, provides for complete control over the operation of the method of the present invention. The operational software may be provided in any of the conventional programming languages (i.e., BASIC, FORTRAN, COBOL, "C", or any other suitable programming language) or it may be implemented in assembly or assembler language for the particular microprocessor or CPU utilized, depending upon the digital computer or processor utilized as well as depending upon any of the specific application constraints.

The present invention is premised upon a user interactive scheme wherein data is obtained which is representative of a predetermined assortment of psychological and/or psychopathological information. The data is input, via the input device 4, into the apparatus 100, during various stages of data entry, and processed so as to provide intermediate as well as final output data and information which is further utilized in performing certain aspects of the method of the present invention. The final data comprises that data which is or may be incorporated into output data reports. The operation of the present invention will be described below with reference to FIGS. 2 through 14. Further appropriate reference to the operation of the apparatus 100 will be made with reference to FIG. 1.

FIG. 2 illustrates an overall operational flow diagram of the method of the present invention. The method of the present invention comprises the initial steps of illiciting an individual's responses to pre-determined questions which may be found in a series of questionnaires or forms which will hereinafter be referred to as "Data Acquisition Forms" (DAF's). Each DAF comprises a series of questions which measure various psychological information which is indicative of numerous and various types of psychological states and/or states of dysfunction (i.e., psychopathology). In the preferred embodiment of the present invention, a series of eight DAF's are utilized. Typical forms for five of the DAF's (DAF-1 through DAF-5), which may be utilized by the present invention, are appended to this application for illustrative purposes and are denoted by Appendices A through E, respectively. It should be noted that the specific questions, response possibilities and forms of the DAF's are subject to modification and revision so as to incorporate future developments in the use and application of the present invention as well as to incorporate future developments in the mental health care field or industry.

FIG. 3 illustrates diagrammatically the main psychological and/or psychopathological groups of information which are assessed by DAF's 1 through 5. Present situational, "external" information at Block 301 are assessed via DAF-3 and DAF-4. This information includes, at Block 302, social problems (including difficulties with relatives and with non-relatives, social isolation and fears, passivity, aggressiveness, distrust of others, and avoidance of others, etc.); at Block 303, threats to the well-being of one's self and/or significant others (including living or working in an unsafe or unhealthy environment, etc.); and at Block 304, dissatisfaction with one's job, education, or standard of living (including lack of money or possessions, job or school problems, and one's state of employment or education, etc.).

Present "internal" information of the individual, at Block 305, are assessed via DAF-1 thru DAF-4. This information includes, at Block 306, bio-hereditary and medical factors (including the individual's physical appearance, traits, characteristics, emotional/physiological reactivity, physical handicaps and health problems, mood states and temperament, etc.); at Block 307, cognitive activity (including the assessed individual's goals, values, appraisals, attributions, irrational beliefs, cognitive style, perception of oneself and other perceptions, and thought disorders, etc.); at Block 308, the individual's behavioral skills and tendencies (including the assessed individual's body language, speech patterns, coping and problem-solving skills, and other behavioral excesses or deficiencies, etc.); and at Block 309, the individual's emotional states (including both "minor" and "major" emotions as described below).

Significant historical and developmental information and traumatic early experiences of the assessed individual, denoted at Block 310, are assessed via DAF-5. This information includes, at Block 311, early relationships with significant others, deaths, being abused or neglected, and peer relationships, etc., and at Block 312, an individual's medical, academic, vocational, and legal history, etc.

FIG. 3A illustrates diagrammatically the aggregation or the combination of DAF questions. The importance of FIG. 3A is that it assists in clarifying various concepts and terms utilized in the present invention. Block 300A indicates the actual questions in the DAF-1 through DAF-5 to which the assessed individual and provider respond. At Block 301A, in the preferred embodiment of the present invention, the responses to these questions may be assigned to memory locations or "cells" within an array or matrix data structure, or a typical spreadsheet data structure, which will be described in greater detail below.

Since the present invention utilizes array or matrix data structures or spreadsheet technologies, it may be helpful at this point to describe the structure and functions of a matrix data structure and/or spreadsheet program. A typical array, matrix, or spreadsheet is basically a grid comprised of rows, which are designated by sequential numerals, and columns, designated by sequential letters. Since, in the preferred embodiment of the present invention, a spreadsheet is utilized, elaboration in this area will concentrate on spreadsheet technology. The spreadsheet program, which may be utilized by the present invention, may typically be a Microsoft Excel® spreadsheet which may be utilized in a Windows® environment. In the preferred embodiment, the spreadsheet which is utilized contains over 16,000 rows and over 250 columns. Each row and column intersect at memory locations or points which are hereinafter referred to or defined as "cells" on the matrix or spreadsheet grid. A cell is identified by its corresponding column letter and row numeral (e.g., "A1" is the cell in the upper left corner of the spreadsheet grid whereas cell "J10" is located ten columns to the right and ten rows down from A1 cell). The width of a cell may be adjusted by modifying the width of the column within which the cell resides, while the height of a cell may be adjusted by modifying the height of the row within which the cell resides.

Cells may have operational commands, data processing commands and/or formulas stored within them, which are capable of performing command, mathematical, logical, and/or various other procedures as indicated by pre-defined alphanumeric codes and/or mathematical formulas written into and stored within a cell. In addition, a cell may be addressed by another cell so that the data entered directly into or stored within a cell may be utilized by a command or formula stored in other cells. Further, a cell may contain numerical data and/or alphanumeric text. Alphanumeric text may also be included as part of a formula so that a specified numerical value results in a specific string of alphanumeric text which may be utilized in the processing routine. For example, a mathematical computation which yields a value of "1", may result in the word "YES" appearing in the cell, while the word "NO" would appear for a value which is not a "1". In the preferred embodiment of the present invention, cells containing commands, mathematical formulas and/or numerical values are designated "data-cells" whereas cells containing only alphanumeric text (including lines and symbols) are designated "text-cells".

Returning once again to FIG. 3A at Block 301A, the cells which receive the DAF response data are located in a Data Analysis Spreadsheet (DAS), which will be described in more detail below. Is should be noted that, although various other spreadsheets may be utilized by the present invention in addition to the DAS, only the structure of the DAS will be referred to at this point, even though certain of structural aspects of the DAS may be consistent with the other spreadsheets utilized by the present invention. The data-cells in the DAS are adjacent to (i.e., on the same row as) corresponding text-cells which provide reference to specific and diagnostically relevant psychological and/or psycho-pathological data and/or other pertinent information, which are hereinafter referred to as "items". Each item has an "item-score" associated therewith. Each "item-score" is defined as an individual's response to a DAF question or questions which are associated with that particular item. Each item-score is stored in pre-assigned data-cells in the DAS. Adjacent to each item-score is an associated text-cell. The text-cell contains either a DAF question or DAF questions which is reprinted verbatim in the spreadsheet, or a paraphrased DAF question or questions, which indicates the actual item.

Figure 14B:
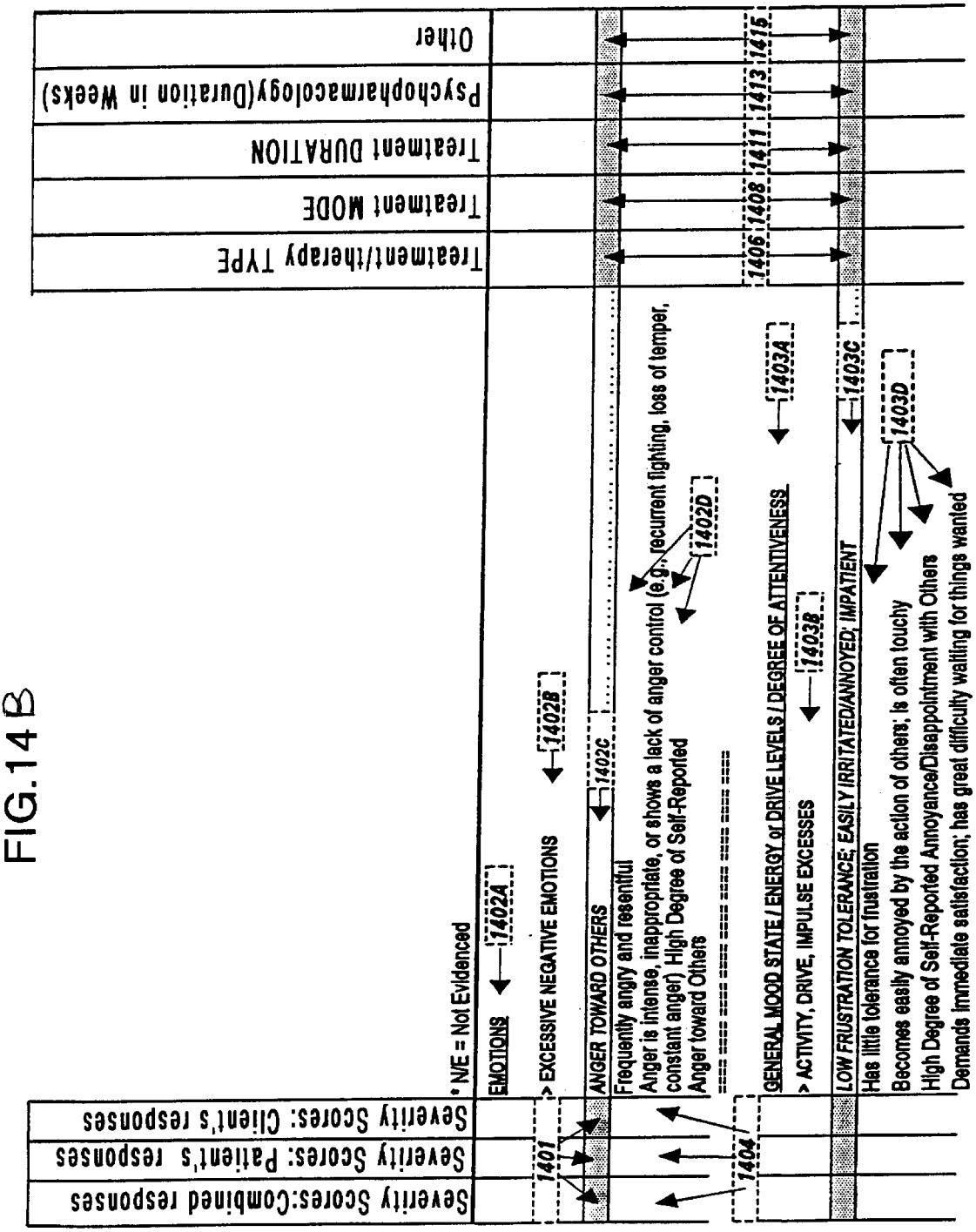
FIG. 14 illustrates a portion of a typical Data Analysis Spreadsheet, utilized by the present invention, which contains data and information stored in memory locations of the apparatus, which constitute certain output data reports which are generated by the present invention.

At Block 302A, the items are grouped into "item-groups" within the DAS, in accordance with known psychological constructs or concepts or statistical analyses, which will be described in more detail below. Refer to FIG. 14 at Location 1402D and 1403D for an example of typical item-groupings. The grouping of items into item-groups is initially derived through a rational and logical review and analysis of the data with respect to psychological principles and theories. The item-groupings may be subsequently confirmed or modified as determined by statistical procedures known as factor analysis, which will also be described in more detail below.

In the DAS, each item-group has a heading, which is hereinafter referred to as an "item-group-heading", which describes the nature of the items therewithin. Refer to FIG. 14 at Locations 1402C and 1403C for an illustration of how the item-group-heading "ANGER TOWARD OTHERS" includes within it items such as "Frequently angry and resentful", "Anger is intense, inappropriate, or shows lack of anger control . . . " and "High Degree of Self-Reported Anger toward Others" and how the item-group-heading "LOW FRUSTRATION TOLERANCE; EASILY IRRITATED/ANNOYED; IMPATIENT" includes within it items such as "Has little tolerance for frustration", "Becomes easily annoyed by the actions of others; is often touchy", "Demands immediate satisfaction; has great difficulty waiting for things wanted" and "High Degree of Self-Reported Annoyance/Disappointment with Others". Each item-group-heading, further, defines a psychological "variable" which is consistent with a known psychological idea, rule, model, construct or concept. Thus, the variables in the present example are labeled "ANGER TOWARD OTHERS" and "LOW FRUSTRATION TOLERANCE; EASILY IRRITATED/ANNOYED; IMPATIENT", respectively. Each variable or item-group-heading, further, has associated therewith, a score which is comprised of the combined scores of the items in its respective item-groups.

At Block 303A, the variables are aggregated, grouped or combined into "factors" of different levels which are utilized to describe patterns of psychological states and/or states of dysfunction, such that a group of factors describe psychopathological disorders and/or syndromes. Refer to FIG. 14 at Locations 1402B and 1403B for examples of level 1 factors (i.e., "EXCESSIVE NEGATIVE EMOTIONS" and "ACTIVITY, DRIVE, IMPULSE EXCESSES", respectively) and at Locations 1402A and 1403A for examples of level 2 factors (i.e., "EMOTIONS" and "GENERAL MOOD STATE/ENERGY or DRIVE LEVELS/DEGREE OF ATTENTIVENESS", respectively).

As with the process of grouping items to make variables, factors can also be derived through a rational and logical review and through an analysis of the data with respect to psychological principles and theories, and/or they may be determined via statistical procedures which are known as factor analysis. While initial factor determinations may be performed without statistical procedures, substantial amounts of data may be factor analyzed statistically so as to confirm or modify the initial variable and factor groups. In addition, such factor analyses may be utilized in the production of various data output reports which, specifically, may be an Individual Patient Profile (IPP) report, a Utilization Review (UR) report and an Individualized Treatment Plan (ITP) report, which will be described in more detail below.

Table 1 provides a more detailed description of the item-groups, variables (item-group-headings) and level 1 and level 2 Factors as they may be organized within the Data Analysis Spreadsheet (DAS). Factors are designated by bold-underlined-upper case letters and by bullets. Variables and items are indented. Also included in Table 1 is a listing of some of the DAF questions and/or items for clarification when necessary. In addition, Table 1 indicates the DAF's from which the data in each main category is obtained.

TABLE 1

DEMOGRAPHICAL INFORMATION
(from DAF-3 and 4)

Age
Sex
Intelligence Level
Verbal Expressiveness
Ethnic/Cultural Background
Family Structure
Occupation TABLE 1-continued EMOTIONS
(from DAF's-1, 3 and 4)

EXCESSIVE NEGATIVE MINOR EMOTIONS
(Degree of Intensity X Frequency)

Annoyance/Disappointment With Self
Annoyance/Disappointment With Others
Sad/Unhappy
Concerned/Uneasy
EXCESSIVE NEGATIVE MAJOR EMOTIONS
(Degree of Intensity X Frequency)

Anger Toward Self
Anger Toward Others
Depression
Worry/Anxiety
- With Panic Attacks
- Phobias
Malicious Envy
Jealousy
Shame
Guilt
EMOTIONAL DEFICITS, INAPPROPRIATENESS, or INSTABILITY Flat Or Grossly Inappropriate Affect
Apathy; Lack Of Empathy, Remorse, And Tender Emotions; Cool Indifference Lack Of Pleasure/Enjoyment In Daily Life; Feelings Of Boredom/Emptiness Affective Instability
  GENERAL MOOD STATE; ENERGY or DRIVE LEVELS;
    DEGREE OF ATTENTIVENESS or AWARENESS
       (from DAF's-3 and 4)

ATTENTIONAL DEFICITS

Inattentive; Distractible; Difficulty Concentrating, Following Instructions, Organizing, Prioritizing Or Persisting On Task
ATTENTIONAL EXCESSES Excessive Vigilance and/or Scanning of the Environment
Difficulty Shifting Focus
ACTIVITY, DRIVE, IMPULSE EXCESSES Hyperactivity
Low Frustration Tolerance; Easily Irritated/Annoyed; Impatient
Poor Impulse/Urge Control; Reckless Behavior; Failure To Adequately Consider The Consequences To One's Actions
Manic Periods
ACTIVITY, DRIVE, IMPULSE DEFICITS Low Energy Level
       COGNITIONS and PERCEPTIONS
          (from DAF's-1 and 2)

THOUGHTS OF DOING HARM TO SELF: SUICIDAL IDEATION
THOUGHTS OF DOING HARM TO OTHERS or PROPERTY
UNFULFILLED/THREATENED/FAILED GOALS and/or VALUES Being Physically Hurt; Handicapped; Seriously Mentally Or Physical Illness Or Disease; Dying
Being Rejected; Ridiculed; Not Enough Love; Affection; Acceptance; Approval; Recognition
Not Having (Or Keeping) Enough Money Or Possessions
Other People Being Physically Or Emotionally Hurt, Ill, Upset; Dying
How Certain People Don't Care About What You Say; What You Want; Don't Respect You; Don't Understand Or Care How You Feel
How You Can't Depend On Or Trust Certain People
Not Having Enough Freedom Or Independence; Not Doing Certain Things On Your Own Or By Yourself; Pressured To Do Things You Don't Want To Do
Not Taking Good Enough Care Of Certain People Or Hurting Them Emotionally Or Physically
Not Enough Fun Or Excitement; Interesting Things To Do; Bored; Not Enough Relaxation, Comforts; Stressed; Not Know What To Do With Your Life; Empty
The Things I Have Done Wrong; Will Do Wrong
The Things Others Have Done Wrong; Will Do Wrong
ATTRIBUTIONS OF RESPONSIBILITY & BLAME TABLE 1-continued Have you ever been bothered by (any of) the above?
If YES, who was RESPONSIBLE for making it happen?
Which person (if any) did something UNFORGIVABLE?
Will you probably be bothered by the (any of) above in the near future?
If YES, who was RESPONSIBLE for making it happen?
Which person (if any) did something UNFORGIVABLE?
FAULTY APPRAISALS, IRRATIONAL BELIEFS,
ERRONEOUS PERCEPTIONS HELPLESS - NOT IN CONTROL . . . like there's NOTHING I CAN DO ABLOUT IT.
There are times that I SHOULD NOT (MUST NOT, OUGHT NOT) get [1] or I SHOULD (MUST, OUGHT TO) have more [2]
I sometimes NEED TO (or HAVE TO) to have less [1] or more [2]
It's sometimes AWFUL (TERRIBLE) to get [1] or not have more [2]
It's a problem that I sometimes CAN'T STAND (CAN'T TOLERATE).
It's a problem that will probably ALWAYS have; it will probably NEVER end.
It's WRONG and UNFAIR for this to happen to me . . . I'm just a VICTIM.
I DESERVE better than this.
It makes me feel INSECURE, SELF-DOUBTING, SELF-CONSCIOUS, or INADEQUATE DEGRADED, BELITTLED, PUT-DOWN, HUMILIATED, or DISGRACED
It makes me feel like I'm NO GOOD or I'm LESS OF A PERSON
It makes me feel like someone else is NO GOOD or is LESS OF A PERSON
It makes me feel like it's PUNISHMENT for things I have done wrong . . . punishment that I DESERVE.
NEGATIVE APPRAISALS OF SELF AND ONE'S ABILITIES Lack Of Self-Efficacy
Pessimism/Hopelessness
Low Self-Esteem; Self-Consciousness; Overly Sensitive; Easily Slighted; Unable To Accept Criticism
INFLATED SELF-APPRAISAL or SELF-IMPORTANCE Narcissism; Self-Centeredness; Grandiosity
IDENTITY PROBLEMS Multiple Personality Disorder OR Personality Changes
Psychogenic Fugue
Psychogenic Amnesia
Depersonalization Disorder
Gender-Identity Problems
NEGATIVE VIEW OF OTHERS Paranoid Ideation; Lack Of Trust; Suspiciousness
COGNITIVE EXCESSES or RIGIDITY Flight OF Ideas/Racing Thoughts
Obsessions
Inflexibility; Dogmatic Thinking Style
DELUSION and HALLUCINATIONS (NON-ORGANIC)

Incoherence/Loosening of Associations/Problems with Reality Testing/ Loss of Body Integration/Disorganized Behavior/Grossly Disturbed Affect or Speech BEHAVIORS
(from DAF's-2, 3 and 4)

EXCESSIVE, ODD, or SOCIALLY INAPPROPRIATE BEHAVIORS

Self-Destructive Behaviors:
Suicidal Behavior
Destructive Behavior Towards Others:
Behaviors That Are Aggressive, Obnoxious, Cruel, Illegal, Irresponsible
Disorders Of Impulse And Compulsive Disorders:

Kleptomania
Pathological Gambling
Pyromania
Trichotillomania
Other Compulsions
Perfectionism
Hoarding Behavior; Lack Of Generosity
Workaholism
Psychoactive Substance Dependence and Abuse TABLE 1-continued Attention/Approval-Seeking; Exhibitionism (Non-Sexual); Manipulative Behavior
Post-Traumatic Stress Reactions
Stereotypy Behavior In Childhood
Peculiar, Odd, or Eccentric Behavior or Appearance
Sexual Paraphilias:

Exhibitionism
Fetishism
Frotteurism
Pedophilia
Sexual Masochism
Sexual Sadism
Transvestic Fetishism
Voyeurism
DEFICIENT BEHAVIORS (Including SKILL DEFICITS)

Poor Or Lack Of Planning/Decision-Making Poor Work Effort/Motivation; Loss Of Initiative; Disinterest; Failure To Persist On Task; Procrastination
Catatonic Behavior
COMMUNICATION PROBLEMS:
EXCESSIVE/DEFICIENT/ECCENTRIC TALKING
and POOR LISTENING
CONSERVATISM versus RISK-TAKING tendencies COGNITIVE-BEHAVIORAL COPING RESPONSES
(from DAF-2)

I tell the person(s) who caused the problem how I feel and try to get them to change the way they act or think. {CONFRONTIVE}
I make sure that I know what I did to cause the problem and/or I apologize or try to make up for what I did. {ACCEPTING RESPONSIBILITY}
I act as if nothing has happened or I try to put it out of my mind and not think about it much. {DISTANCING}
I try to control my feelings and take my time before I act. {SELF-CONTROLLING}
I talk to someone about what I'm going through or I ask certain people for advice or help. {SEEKING SUPPORT}
I try to spend time by myself, away from most people. {ESCAPE-AVOIDANCE through SOCIAL ISOLATION}
I hoped that a miracle would somehow make things better or that my dreams or wishes would be answered {ESCAPE-AVOIDANCE through WISHFUL THINKING}
I decide what I have to do to and then I use my plan to try to solve the problem. {PLANFUL PROBLEM SOLVING}
I hoped that a miracle would somehow make things better {ESCAPE-AVOIDANCE through WISHFUL THINKING}
The problem helped me change or grow in a good way, helped me find new faith, or helped me re-discover what is important in life. {POSITIVE REAPPRAISAL}
I accepted that there was nothing I could do about it, so I did nothing.

CURRENT PSYCHO-SOCIAL STRESSORS
(from the DAF's-3 and 4)

PROBLEMATIC SOCIAL INTERACTIONS

Attachment Difficulties In Infancy Or Early Childhood
Separation Anxiety/Thoughts Of Abandonment
Dependency
Passivity/Unassertiveness; Proneness To Peer-Pressure
Deficient/Minimal Socialization
Social Withdrawal; Avoidance; Reluctance To Enter Relationships; Isolation; Under Socialization; Interpersonal Indifference; Shyness
Loneliness; Distressed Being Alone; Devastated By Relationship Breakup
Dysfunctional Family Dynamics Problems with One's Parents
Problems with One's Own Children
Problems with One's Siblings
Problems with One's Extended Family
Relationship Problems With Non-Family Persons Problems with One's Friends/Peers/Co-workers/etc.
Problems with Authority
PROBLEMS EXPERIENCED BY SIGNIFICANT OTHERS Substance Abuse By Significant Other
Serious Physical Or Emotional Illness Or Death Of A Loved One Or

TABLE 1-continued

Family Member
A family member, loved one, or close friend is having serious troubles
OCCUPATIONAL/EDUCATIONAL PROBLEMS Current Problems with WORK or SCHOOL
If you are going to RETIRE shortly or have already retired: My retirement is a problem
VICTIMIZATION Has recently become the VICTIM of a natural disaster
Has recently become the VICTIM of ACCIDENT, ABUSE or CRIME
Other Problems PROBLEMS WITH ONE'S LIVING ENVIRONMENT
(e.g., Dangerous or Inadequate)
LEGAL PROBLEMS
If you are a MALE: My partner recently got pregnant or I recently became a parent
If you are FEMALE: I recently became pregnant or gave birth
If you WANT TO BE a PARENT: We are unable to have children
    BIO-MEDICAL UNHEALTH/ORGANIC BRAIN DYSFUNCTIONS/
                     GENETIC PREDISPOSITIONS/
            SEXUAL DYSFUNCTIONS and DISORDERS
                     (from the DAF's-3 and 4)

Organically Induced Syndromes
Physical Appearance/Abilities Concerns: Atractiveness;
Coordination; Strength; Talents
Allergies Possibly Affecting Psychological Condition
Eating Problems - Under-Eating/Anorexia-Bulimia/Overeating
Sleeping Problems/Changes
Factitious Disorders
Physiological Symptoms/Somatization
Sexual Dysfunctions
Sexual Arousal Disorders
Orgasm Disorders
Sexual Pain Disorders
Learning Disabilities
Memory Problems and Amnesia
            Important Historical (Childhood) Information
                         (from the DAF-5)

The nature of early relationships between the assessed individual and his or her mother (or primary female caretaker), father (or primary male caretaker), or another unspecified person are measured by the following:
> The amount of ACCEPTANCE, RESPECT, and APPROVAL I received from this person:

This person either:

CRITICIZED, RIDICULED or REJECTED me too much;
made me feel like I was usually DISAPPOINTING him/her;
made me feel that I was NEVER GOOD ENOUGH.
This person either:

SPOILED ME;
made me feel so SPECIAL that I felt I DESERVED ONLY THE BEST;
made me feel that things SHOULD ALWAYS BE MY WAY or that
I MUST GET WHATEVER I WANTED;
told me that I was GREAT even when I knew it was NOT TRUE.
This person either:

gave me ACCEPTANCE, RESPECT, or APPROVAL only if I LIVED UP TO his/her EXPECTATIONS or if I in the things he/she wanted me to do;
Rejected, Ridiculed, or treated ME POORLY if I DISAPPOINTED him/her or if I FAILED to ACHIEVE.
This person either:

gave me LOVE, ACCEPTANCE, or RESPECT was shown to me by this person ALL THE TIME;
made me feel like I was SPECIAL and IMPORTANT to him/her even when I didn't do things well.
> The amount of AFFECTION I received from this person:

This person was usually:

NOT PHYSICALLY or VERBALLY AFFECTIONATE;
usually COLD, ALOOF, SHY, or UNCOMFORTABLE with affection

TABLE 1-continued

This person was usually overly or inappropriately AFFECTIONATE with me (such as being SEDUCTIVE)
This person was usually APPROPRIATELY AFFECTIONATE with me; I felt a HEALTHY
> The amount of ENCOURAGEMENT, SUPPORT, and INSPIRATION I received from this person:

This person usually either:

DISCOURAGED, BLOCKED, or INHIBITED me;
made me feel HOPELESS or made me believe that I could
NEVER AMOUNT TO ANYTHING
This person usually either:

ENCOURAGED me TO DO too much;
PUSHED TO DO things that were TOO DIFFICULT for me
made me feel either FRUSTRATED, STRESSED-OUT or
like a FAILURE
This person usually ENCOURAGED, SUPPORTED, MOTIVATED or INSPIRED me in a good way
> Type of GUIDANCE and DISCIPLINE I received from this person:

This person was either:

TOO LENIENT, TRUSTING, or PERMISSIVE with me;
allowed me to GET AWAY WITH TOO MUCH bad behavior or laziness
This person was either:

overly STRICT, INTRUSIVE, DOMINEERING, DISTRUSTING, OVERBEARING with me;
made me feel like I was BEING CONTROLLED
This person was very INCONSISTENT in the way he/she guided or disciplined me
This person usually RESPECTED my RIGHTS and encouraged my INDEPENDENCE while his/her guidance and discipline HELPED ME make good decisions
> The amount that I could DEPEND UPON, TRUST, or FEEL SECURE with this person:

This person either:

could NOT BE DEPENDED UPON or TRUSTED;
DISHONEST, INSINCERE, or HYPOCRITICAL, or often ACTED in a FALSE (FAKE or PHONEY) WAY;
made me feel INSECURE because he/she often threatened to ABANDON me;
This person either:

was OVERLY HELPFUL, DID TOO MUCH for me, or was OVER-PROTECTIVE;
made me DEPENDENT ON him/her;
made me feel INSECURE or FEARFUL without him/her
This person was so inconsistent that I usually DIDN'T KNOW whether to trust or depend upon him/her
This person was DEPENDABLE and TRUSTWORTHY in a good way and made me FEEL SECURE
> The amount of UNDERSTANDING and COMMUNICATION I had with this person:

This person:

NEVER REALLY UNDERSTOOD what I thought or what I felt;
could NOT communicate well with me
This person:

UNDERSTOOD ME too well;
made me feel like I had NO MIND OF MY OWN
This person really UNDERSTOOD ME in a good way, we COMMUNICATED well
> The amount of CARE, CONCERN, or EMPATHY shown by this person:

This person was usually either:

SELF-CENTERED, SELFISH, or was mostly interested in being the CENTER OF ATTENTION;
INSENSITIVE, UNSYMPATHETIC, IGNORED MY EMOTIONAL NEEDS, MADE ME FEEL UNWANTED;
a MANIPULATIVE USER who TOOK ADVANTAGE OF OTHERS

TABLE 1-continued

This person either:

was TOO INVOLVED in other people's lives;
often SUFFERED for OTHERS like a SELF-SACRIFICING MARTYR
This person was UNSELFISH and DEVOTED to OTHERS in a
PLEASANT and HEALTHY WAY
> The amount to HUMOR, ENJOYMENT, and HAPPINESS shown by
this person:

This person was usually either:

TOO SERIOUS, DULL, UNHAPPY, TENSE, or EASILY UPSET;
almost NEVER HAD FUN or LAUGHED
This person was usually either:

TOO SILLY or FOOLISH;
almost NEVER TOOK ANYTHING SERIOUSLY
This person was: very INCONSISTENT; one day HAPPY or HAVING
FUN and the next day UPSET or UNHAPPY
This person was usually PLEASANT, ENJOYABLE, ABLE TO LAUGH
and FOOL AROUND, but he/she could be
SERIOUS WHEN NECESSARY
Other Important Information about different people When I was growing up, this person:

was mostly ABSENT FROM MY LIFE
EMOTIONALLY ABUSED me
PHYSICALLY or SEXUALLY ABUSED people in my family
EMOTIONALLY ABUSED other people in my family
was in serious TROUBLE with the LAW
let ALCOHOL or DRUG USE cause serious problems
DIED NON-VIOLENTLY while relatively YOUNG
DIED VIOLENTLY (other than Suicide)
KILLED HIM/HERSELF (committed SUICIDE)
was seriously PHYSICAL DISABLED or ILL
had serious EMOTIONAL problems
had serious LEARNING problems
Other Issues about My Past When I was growing up, I often felt:

DIFFERENT, LONELY or like I DIDN'T FIT IN with my peers
UNWANTED, UNLOVABLE or UNDESIRABLE
very FEARFUL, WORRIED or ANXIOUS
very ANGRY
very SAD or DEPRESSED
very ASHAMED or EMBARRASSED
very GUILTY
very JEALOUS or ENVIOUS of certain people
When I was growing up, there was a rather long period of time during
which I believed that:

I was UNATTRACTIVE (UGLY, FUNNY-LOOKING)
I was INTELLECTUALLY INFERIOR (UNINTELLIGENT, STUPID)
I was PHYSICALLY INFERIOR (WEAK, UNCORRDINATED)
I was ECONOMICALLY INFERIOR (POOR, LOW SOCIAL CLASS)
When I was growing up:

I was very OVERWEIGHT
I was very UNDERWEIGHT
I was BULIMIC or ANOREXIC
I had a DRINKING or DRUG ABUSE problem
I had SERIOUS MEDICAL or PHYSICAL PROBLEMS
I had SERIOUS EMOTIONAL problems
I tried to KILL MYSELF
I had been HOSPITALIZED for EMOTIONAL PROBLEMS
I RAN AWAY FROM HOME for a long time
I did things that got me into serious TROUBLE WITH THE LAW
I was very CONFUSED about my SEXUAL IDENTITY
If you are Adopted: I was very upset about my ADOPTION
I sometimes REGRET that:

I was a TEENAGE PARENT
I DROPPED OUT of SCHOOL
I had an ABORTION

Referring once again to FIG. 2, the method of the present invention is initiated by the provider at Step 200. At Step 201, the DAF-1 is administered to the assessed individual by the health service provider who may read questions from the DAF's to the assessed individual and record the individual's responses corresponding thereto on response sheets or answer grids. In the alternative, the assessed individual may simply read and answer the questions independently.

In the preferred embodiment, the DAF-1, comprises questions designed to measure the relationship between the assessed individual's thoughts and emotions. In the preferred embodiment, the thoughts which are measured may pertain to eleven groups of major desired goals which the assessed individual believes he or she is failing to attain, has already failed to attain, or will probably fail to attain in the future, and/or important values which the assessed individual believes he or she is failing to live up to, has already failed to live up to, or will probably fail to live up to in the future (refer to the "Unfulfilled/Threatened/Failed Goals and/or Values" item-group in the "Cognition and Perception" section of Table 1 for the specific items).

In addition, ten emotions, including four "minor" emotions and six "major" emotions (refer to the "Excessive Negative Minor Emotions" and the "Excessive Negative Major Emotions" item-groups in the "Emotions" section of Table 1 for the specific items), are also measured with respect to their connection with each of the aforedescribed beliefs, thoughts, or cognitions. In the preferred embodiment, each assessed individual may answer the DAF questions directly or a provider may reads the questions to the individual and record the assessed individual's responses.

It should be noted at this juncture that the DAF questions, items, item-groups, variables, and factor groupings, described above and/or listed in Table 1, are subject to modification and revision so as to incorporate future developments in the use and application of the present invention as well as to incorporate future developments in the mental health care field or industry and depending upon the results of the statistical factor analysis routines which may be performed on the data acquired via the present invention.

In the preferred embodiment, the assessed individual responds to each item on a nine-point scale by a numeral from "0" though "8" which indicates the frequency of the specific thought, hereinafter designated the "Thought-Frequency scores", and the intensity of the specific emotion which the assessed individual experiences when thinking these thoughts, hereinafter designated the "Emotion-Intensity scores". In the preferred embodiment, the numeral "0" corresponds to a "not at all" or zero frequency or intensity while the numeral "8" corresponds to a frequency or intensity of "a great deal". Further, it should be noted that various scales and various scale ranges may be utilized in order to perform this method. Therefore, the "0" to "8" scale is not the only scaling scheme which may be utilized. It should also be noted that the scaling methods and/or ranges utilized by the present invention are subject to modification and revision so as to incorporate future developments in the use and application of the present invention as well as to incorporate future developments in the mental health care field or industry.

The Thought-Frequency and Emotion-Intensity scores, which are representative of the assessed individual's DAF-1 responses, are then entered into the apparatus 100 of FIG. 1 at Step 202 of FIG. 2, via the data input means 4 of FIG. 1, which may be either via a keyboard, an optical scanner, a modem, or other suitable means of data entry. It should be noted that data may also be entered manually such as by a mouse or by a keyboard via the user command entry device 5.

Information may also be entered into the apparatus 100 at a remote site of testing via a user interactive interface and display device which may be utilized in an alternative embodiment of the present invention and which is described hereinbelow in conjunction with FIG. 15. In the alternative embodiment, information may be transferred via modem or other suitable means, via a network or communication link-up system, into the apparatus 100 at the processing center. It is also envisioned that hard copy responses may be mailed to the processing center and entered into the apparatus 100 by the input device 4 of FIG. 1 or by any suitable method or means. Once entered into the apparatus 100, this data, indicative of DAF-1 responses, is stored, at Step 203 and 203A in FIG. 2, in the databank 8 of FIG. 1 and into the appropriate database which is a Database of Assessed Individuals' Profiles (DB-1).

In the Database of Assessed Individuals' Profiles (DB-1), the data obtained from every individual who has undergone assessment by the present invention may be stored and maintained for present as well as for future use. In the preferred embodiment, all such data is stored so as to obtain a larger and an ever-increasing memory store or database which will be most valuable in performing the statistical routines which may be utilized by the present invention.

The system processing of all of the DAF data occurs at Step 204. The system processing scheme utilizes the data from the DAF's along with theoretical and research-based psychological and/or psychopathological data and/or other pertinent information which exists in the mental health field, in order to arrive at the results sought to be obtained by the present invention. In the preferred embodiment of the present invention, processing is accomplished by utilizing spreadsheet technologies and generic data bases. It is also important to note that conventional programming languages along with their corresponding data structures may also be utilized in conjunction with the present invention. It should be noted that because the processing scheme in the preferred embodiment is presently comprised of interlinked spreadsheets, which may be utilized in conjunction with generic data bases, the processing schemes of the present invention are to be described hereinafter using conventional spreadsheet terminology. It should also be noted, however, that generally known program languages and data structures and array or matrix programs may be utilized as alternatives to the spreadsheet programs.

Figure 4B:
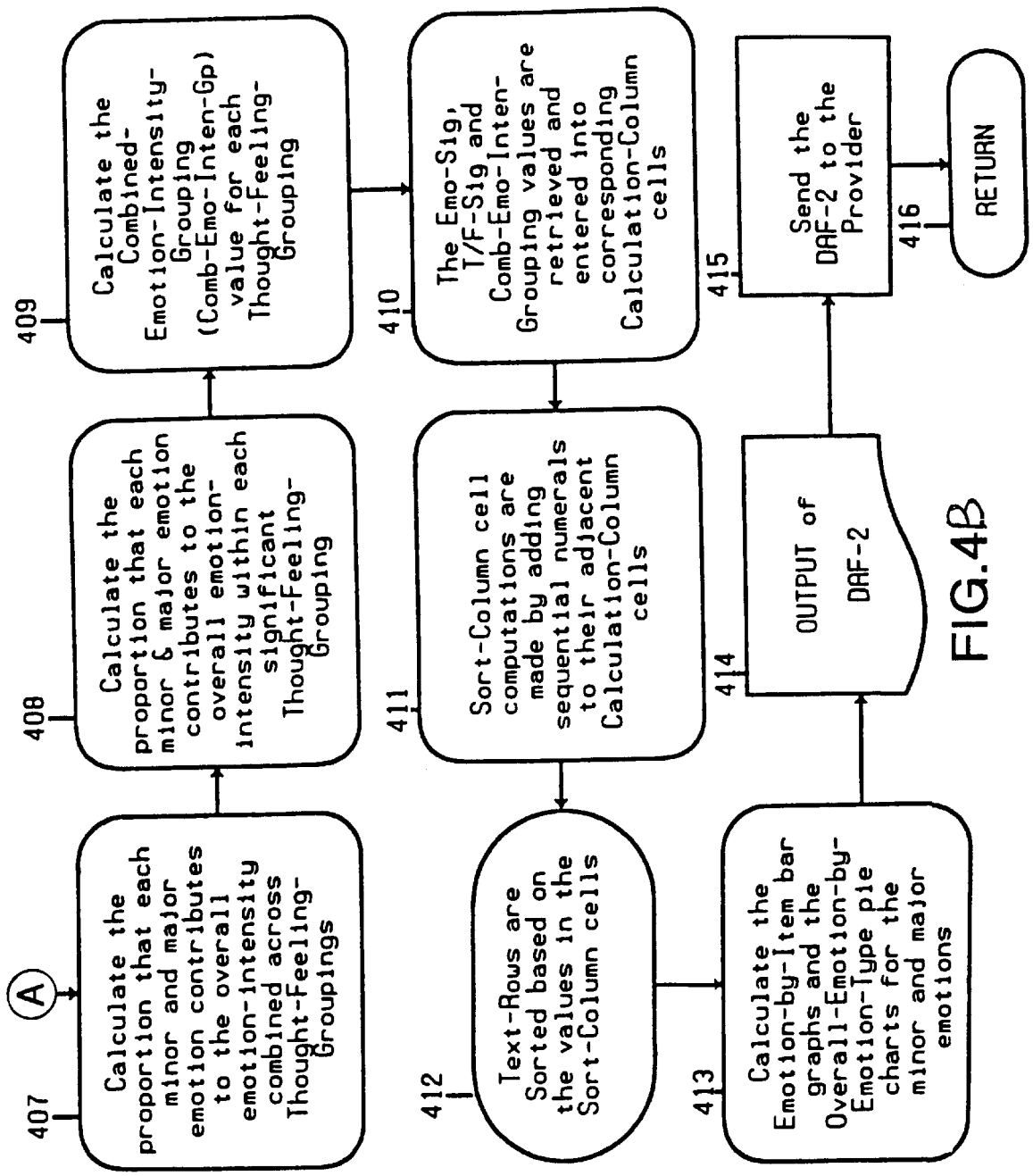
FIG. 4 illustrates an operational flow diagram of the method of the present invention which pertains to the input data, the data processing and the generation of output data obtained from a first data acquisition means.
Figure 5:
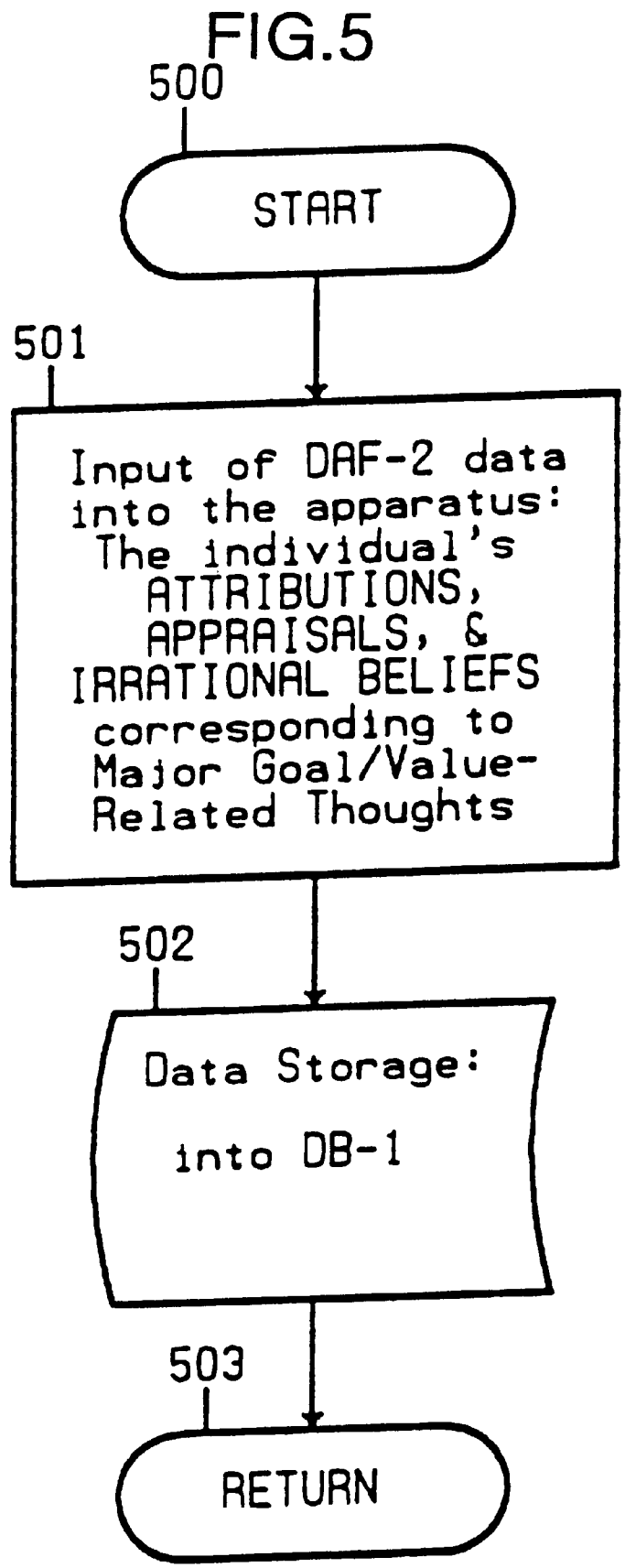
FIG. 5 illustrates an operational flow diagram of the method of the present invention which pertains to the input and storage of data from a second data acquisition means.

Returning once again to FIG. 2, the DAF-1 data is processed by the CPU 1 at Step 204. FIG. 4 illustrates the processing and data storage scheme for the DAF-1 data which takes place at Step 204 of FIG. 2. The processing of the DAF-1 data starts at Step 400 in FIG. 4. At Step 401, the individual's DAF-1 responses are input into the apparatus 100 by any of the aforedescribed data input means and are stored in the Database of Individuals' Profiles (DB-1). At Step 402, each of the Thought-Frequency scores obtained from DAF-1 are entered into pre-assigned data-cells (i.e., spreadsheet cells containing commands, formulas and/or numerical values as described above) in a spreadsheet hereinafter designated the DAF-1 Spreadsheet. The DAF-1 Spreadsheet, it should be noted, constitutes a second spreadsheet utilized by the present invention, which is in addition to the Data Acquisition Spreadsheet (DAS) described above. At Step 403 each of the Emotional-Intensity scores obtained from the DAF-1 are also entered into data-cells in the DAF-1 Spreadsheet.

At Step 404, the Thought-Frequency and Emotional-Intensity scores undergo a series of mathematical calculations which compute the first of a series of data values, hereinafter designated the "Emotion-Significance" values. The Emotion-Significance values are computed by formulas stored in the Emotion-Significance data-cells. The formulas instruct the CPU 1, of the apparatus 100 in FIG. 1, to first determine which of the eleven Thought-Frequency scores are greater than or equal to an arbitrary, or a statistically pre-determined, Thought-Frequency cutoff value. For each of the Thought-Frequency scores which is greater than or equal to the cutoff value, it is then determined which of the ten Emotion-Intensity scores, corresponding to that Thought-Frequency score, is greater than or equal to a statistically pre-determined Emotion-Intensity cutoff value. If an Emotion-Intensity score and its corresponding Thought-Frequency score are both greater than or equal to their respective cutoff values, the score is considered "significant" and the Emotion-Intensity "raw score" value is entered into a pre-assigned Emotion-Significance data-cell. A raw score equals the actual response score which an individual makes in response to a DAF question. However, if the Thought-Frequency and/or Emotion-Intensity score is determined to be non-significant (i.e., it is not greater than or equal to their respective cutoff values), then a value of "0" is assigned to the respective Emotion-Significance data-cell.

At Step 405, the second in the series of calculations is performed with the result designated as the "Thought-Feeling-Grouping-Significance" values. A "Thought-Feeling-Grouping" is defined as a Thought-Frequency item along with the ten corresponding Emotion-Intensity items corresponding thereto. Formulas located in the Thought-Feeling-Grouping-Significance data-cells instruct the CPU 1 to assign to each of the data-cells a value of "1" if the Thought-Frequency score of the corresponding item-group is "significant" (i.e., if it is greater than or equal to its respective cutoff value) and if there is at least one significant corresponding Emotion-Intensity score within that same item-group. If the score is "non-significant" (i.e., if it is less than its respective cutoff value), a value of "0" is assigned to the Thought-Feeling-Grouping-Significance data-cell. This process is repeated for all of the eleven Thought-Feeling-Groupings which may be utilized.

At Step 406, the third in the series of calculations is performed with the result designated as the "Thought-Emotion-Product" values. Formulas in the Thought-Emotion-Product data-cells instruct the CPU 1 to multiply each significant Thought-Frequency score by the corresponding significant Emotional-Intensity scores in order to yield Thought-Emotion-Product values.

At Step 407, the fourth in the series of calculations is performed in order to determine the percentage with which each minor and major emotion contributes to the overall emotional intensity which is combined across the board for all of the eleven Thought-Feeling-Groupings. These calculations are performed by dividing the Thought-Emotion-Product value for each minor emotion by the sum total of all minor emotion Thought-Emotion-Product values and then by dividing the Thought-Emotion-Product value for each major emotion by the sum total of all major emotion Thought-Emotion-Product values.

At Step 408, the fifth in the series of calculations is performed in order to determine the percentage with which each of the Thought-Feeling-Grouping's minor and major emotions contributes to the overall emotional intensity of those particular Thought-Feeling-Groupings. These calculations are performed by dividing the Thought-Emotion-Product value for each minor emotion by the sum total of all minor emotion Thought-Emotion-Product values in the particular Thought-Feeling-Grouping and further, by dividing the Thought-Emotion-Product value for each major emotion by the sum total of all of the major emotion Thought-Emotion-Product values in that particular grouping.

At Step 409, the sixth in the series of calculations is performed with the result designated as the "Combined-Emotion-Intensity-Grouping" values. These values determine the overall combined-emotion-intensity value for each Thought-Feeling-Grouping. The Combined-Emotion-Intensity-Item-Grouping values are calculated by summing the Emotion-Intensity values for the minor emotions and then by summing the Emotion-Intensity values for the major emotions. The sum of the Emotion-Intensity values for the major emotions may then multiplied by a logically and/or statistically determined weighting value (since the major emotions may exert a more "powerful" influence on the person than the minor emotions) and then, finally, by adding the sum of the minor emotion values to the weighted major emotion values.

At Step 410, the CPU 1 is instructed to retrieve the Emotion-Significance values, the Thought-Feeling-Group-Significance values and the Combined-Emotion-Intensity-Grouping values and to enter these values into their corresponding pre-determined cell locations in a designated "calculation-column". The calculation-column cells comprise a pre-specified column in the DAF-1 Spreadsheet.

At Step 411, formulas which are stored in adjacent sort-column cells, instruct the CPU 1 to add, to the calculation-column cell values, sequentially descending numerical values which are located in other adjacent cells. The resulting summed values, which are stored within cells in a designated "sort-column", are then utilized in order to determine whether large cells of text, which are located in other adjacent cells on the same row, will be included in the data output report. These text-cells, it should further be noted, comprise the actual alpha-numerical text which will be utilized in forming the data output reports which will be described below.

The rows of text are then sorted sequentially at Step 412 based upon the values in the sort-column cells. Then, at Step 413, Emotion-by-Item-Group bar graphs and Overall-Emotion-by-Emotion-Type pie graphs may be computed by the apparatus 100 for the minor and major emotions for the use and convenience of the provider or payer. The sorted rows of text are then output at Step 414 by the apparatus 100 in order to produce the second of the DAF's, DAF-2, the generation of which is dependent upon the scores obtained via the DAF-1 so as to formulate a customized DAF-2 which minimizes administration time and maximizes efficiency by eliminating the further assessment of psychological information deemed "non-significant" by the analysis of the assessed individual's DAF-1 responses. The DAF-2 can then be generated via the output device 7 of FIG. 1, and sent or transmitted, at Step 415, to the provider or other appropriate entity for further assessment of the individual. The operational sequence then returns to the main operational program at Step 416.

The responses to the DAF's 2–7 may then obtained in a suitable manner. While the procedure will be described below as being in the order of DAF-number, it should be noted that it is also possible to obtain out-of-sequence responses to the various DAF's, with the only constraint being that the DAF-1 response data be obtained initially in order to generate the DAF-2. While a specifically defined number of DAF's are described as being utilized by the present invention, it should be noted that any number of DAF's, having any one of a number of varieties, forms, or contents, may be utilized as long as the required data and information is obtained for use by the present invention.

The obtaining and processing of the DAF-2 responses at Step 205 of FIG. 2 will be described in more detail below. The DAF-2, in the preferred embodiment, contains questions which are in a true-false format as well as questions designed to illicit open-ended responses and which are designed to be answered in conversational dialogue between the assessed individual and the provider. The administration of the open-ended questions is optional and is not utilized by the computational methods of the present invention. These open-ended questions, however, may provide useful clinical information to the provider as these questions provide an opportunity for the assessed individual to elaborate upon some of the True-False or other limited response questions and to explain in greater detail the individual's reported feelings and/or thoughts. The assessed individual's responses to these optional open-ended questions may be recorded.

The processing and storage scheme for the DAF-2 data takes place at Step 203 of FIG. 2. The processing of the DAF-2 data commences at Step 500 in the flowchart of FIG. 5. In the preferred embodiment of the present invention, the questions which comprise the DAF-2 are designed to assess the individual's cognitive attributions, appraisals and irrational beliefs as they relate to the assessed individual's thoughts and feelings pertaining to the major goals and/or values as assessed by the DAF-1. An assessed individual's endorsement of the attributions, appraisals and irrational beliefs are measured by having the assessed individual respond, in the preferred embodiment, by either a "yes" or a "no" response to various questions which may then be recorded. In the preferred embodiment, the data representative of this information is input via input device 4 into the apparatus 100 at Step 501. Following the input of the data, the data is sent, at Step 502, to the databank 8 of FIG. 1 and, in particular, is stored within the Database of Assessed Individuals'Profiles, DB-1. There is no processing of the DAF-2 data at this time, but rather this data is stored for later use. The system then returns to the main operational program sequence at Step 503.

Figure 6:
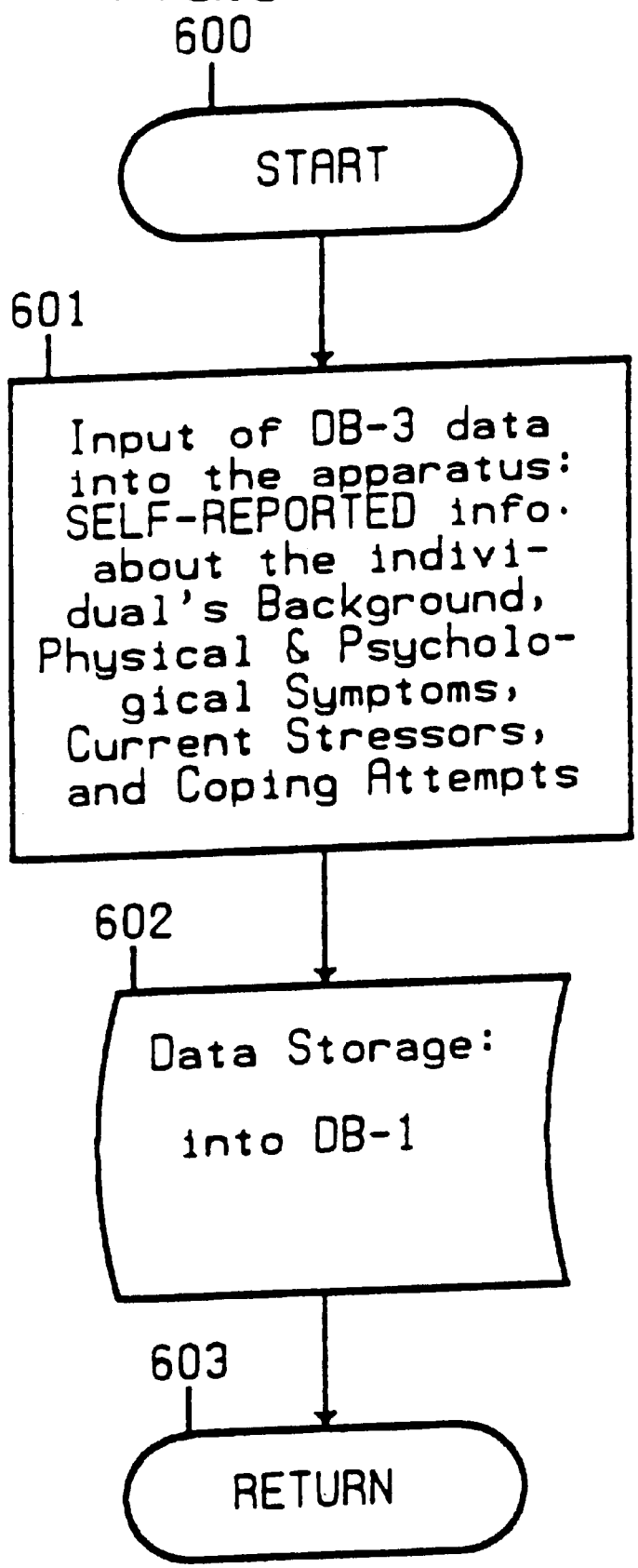
FIG. 6 illustrates an operational flow diagram of the method of the present invention which pertains to the input and storage of data from a third data acquisition means.

The obtaining and processing of the responses to the DAF-3 then occurs at Step 206 of FIG. 2. FIG. 6 illustrates the processing and storage scheme for the DAF-3 data which takes place at Step 203 of FIG. 2. Referring to FIG. 6, the scheme commences at Step 600. In the preferred embodiment of the present invention, the questions which comprise the DAF-3 are designed to assess self-reported information which pertain to the assessed individual's background (i.e., age, sex, nationality, religion, socio-economic status, employment, education, etc.), family dynamics (i.e., birth order, marital status, current relationships with family members, etc.), medical and physical illnesses, problems and symptoms, existing psychological problems and symptoms, history of psychological treatment, medications being taken, current environmental stressors, and the outcome of coping attempts, etc. In the preferred embodiment, the assessed individual provides this data by responding to questions according to various assessment scales. Following the input of the DAF-3 data via input device 4, into the apparatus 100 at Step 601, the data is stored at Step 602 in the Database of Assessed Individuals'Profiles, DB-1, of the databank a of FIG. 1. This step is also illustrated as Step 203A of FIG. 2. The system then returns at Step 603 to the main operational program.

Figure 7:
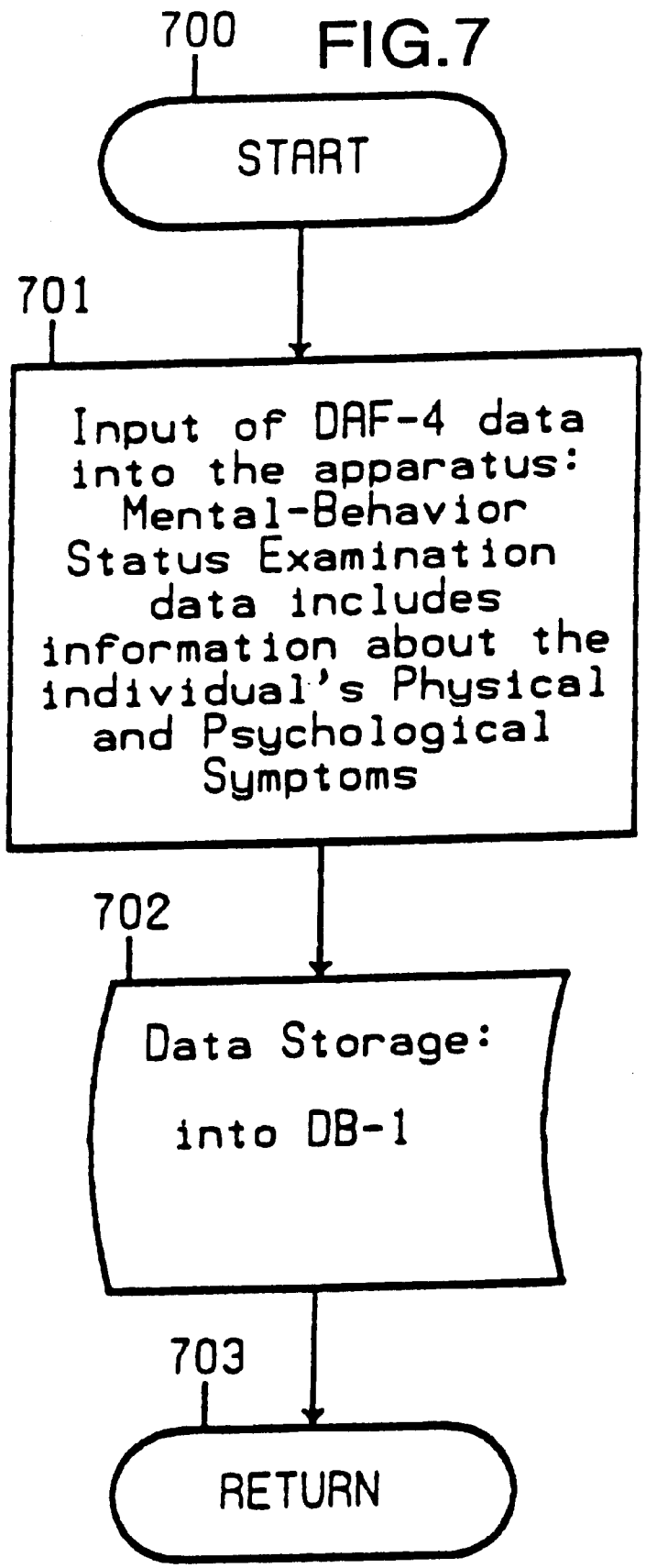
FIG. 7 illustrates an operational flow diagram of the method of the present invention which pertains to the input and storage of data from a fourth data acquisition means.

The obtaining and processing of the DAF-4 responses then occurs at Step 207 of FIG. 2. FIG. 7 illustrates the processing and storage scheme for the DAF-4 data which takes place at Step 207 of FIG. 2. In the preferred embodiment of the present invention, the questions which comprise the DAF-4 are designed to obtain the provider-reported assessment of information concerning the assessed individual's physical and psychological symptoms, including items which may overlap with the assessed individual's self-reports via DAF-3. In addition, the DAF-4 questions may be designed to obtain information pertaining to the treatment methods, techniques, approaches, programs, and/or facilities utilized by the provider in treating the individual, as well as other pertinent treatment information. In the preferred embodiment, the health care provider provides this data by responding to questions with various assessment scales. Following the commencement of the routine at Step 700, the DAF-4 data is input via input device 4 into the apparatus 100 at Step 701. The data is then stored at Step 702 in the databank 8 of FIG. 1 and, in particular, in the Database of Assessed Individuals' Profiles, DB-1, at Step 203A of FIG. 2. The system then returns at Step 703 to the main operational program.

Figure 8:
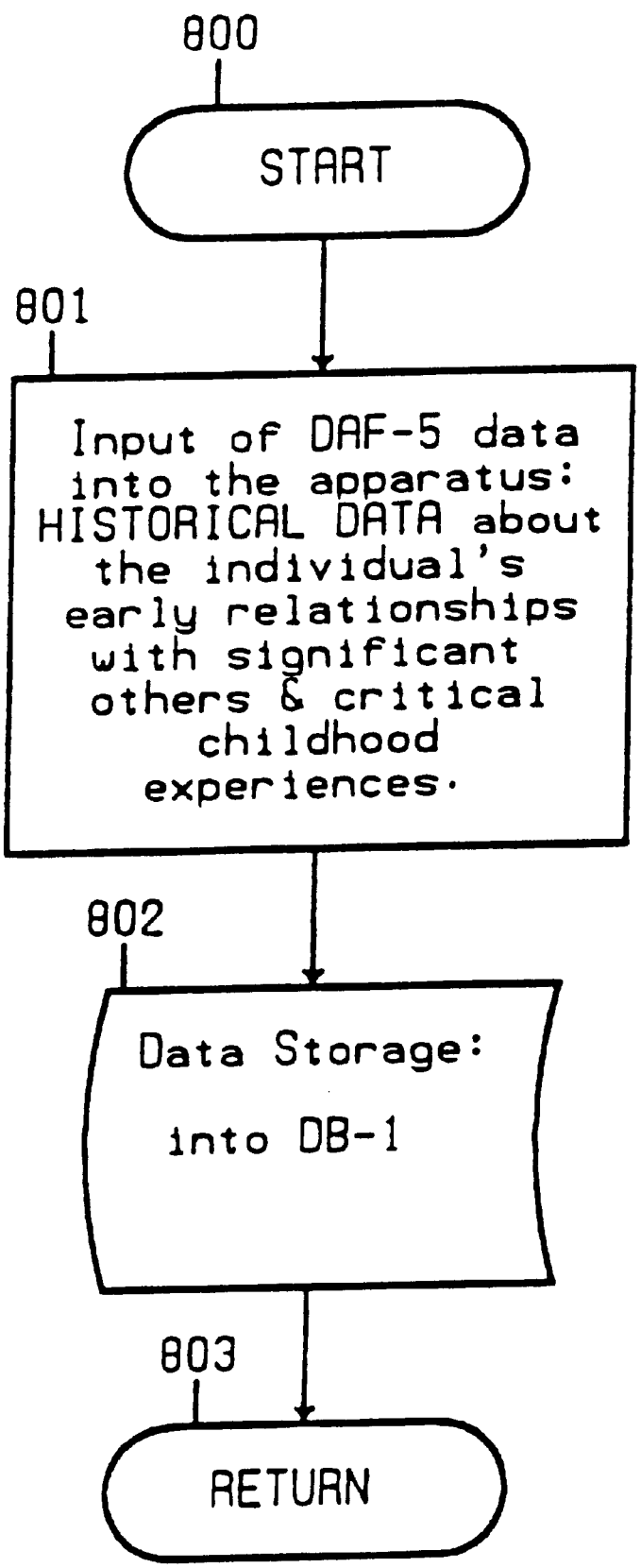
FIG. 8 illustrates an operational flow diagram of the method of the present invention which pertains to the input and storage of data from a fifth data acquisition means.

The obtaining and processing of the responses to the DAF-5 then occurs at Step 208 of FIG. 2. FIG. 8 illustrates the processing and storage scheme for the DAF-5 data which takes place at Step 208 of FIG. 2. In the preferred embodiment of the present invention, the questions which comprise the DAF-5 are designed to obtain information pertaining to the assessed individual's past including the assessed individual's early relationships with significant others (i.e., how the assessed individual, during childhood, was treated by parents, siblings, other relatives, and important people outside of the family, etc.) and critical childhood experiences (i.e., traumatic or painful experiences such as deaths, abuse or neglect, legal difficulties, academic, and health problems, etc.). Following the commencement of the routine at Step 800, the DAF-5 data is input via input device 4 into the apparatus 100 at Step 801. The data is then stored at Step 802 in the DB-1 database of the databank 8 of FIG. 1 at Step 203A of FIG. 2. The system then returns at Step 803 to the main operational program.

Figure 9:
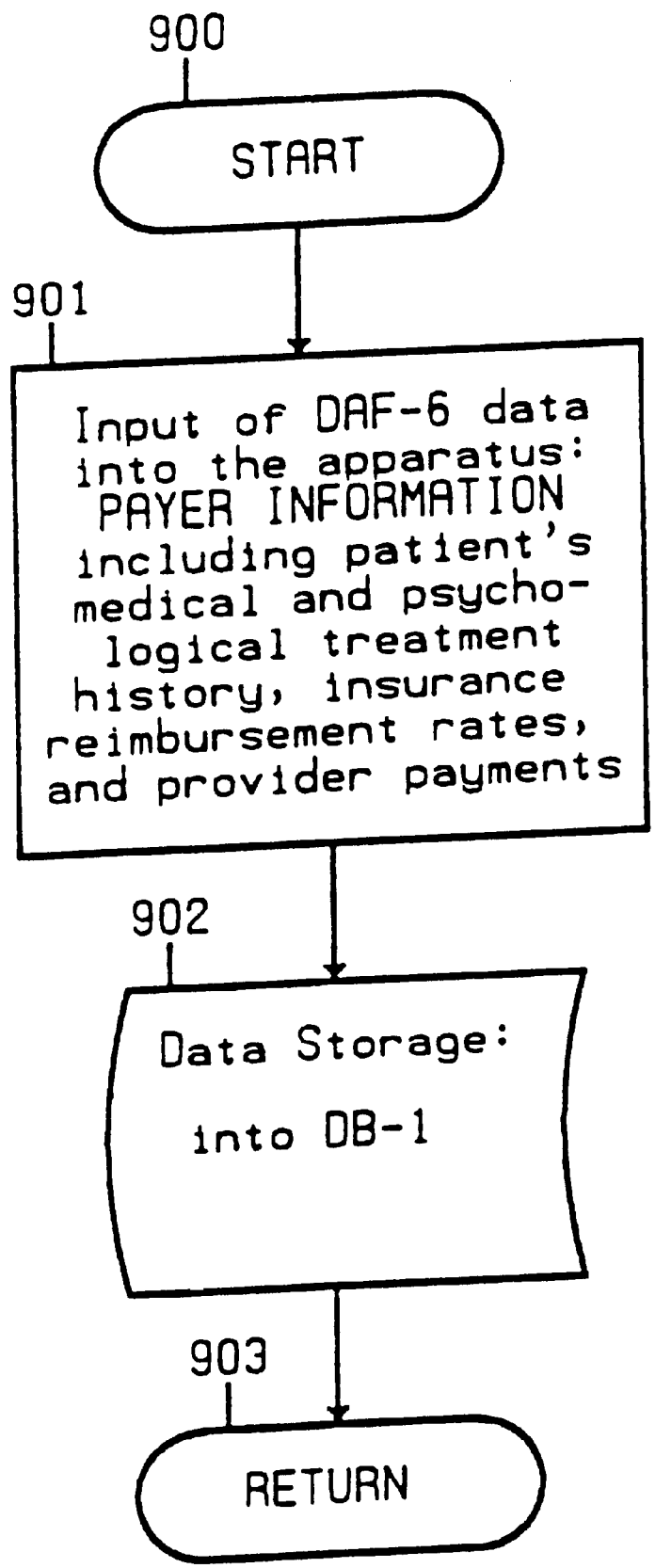
FIG. 9 illustrates an operational flow diagram of the method of the present invention which pertains to the input and storage of data from a sixth data acquisition means.

The obtaining and processing of the responses to the DAF-6 then occurs. FIG. 9 illustrates the processing and storage scheme for the DAF-6 data which takes place at Step 209 of FIG. 2. In the preferred embodiment of the present invention, the questions which comprise the DAF-6 are designed to obtain information from the assessed individual's insurance company or other pertinent organization relating to the assessed individual's medical and psychological history, the insurance company's payment schedules or reimbursement rates, and previous payments made to the assessed individual's health care provider. Following the commencement of the routine at Step 900, the DAF-6 data is input via input device 4 into the apparatus 100 at Step 901. The data is then stored at Step 902 in the DB-1 database of the databank 8 of FIG. 1 at Step 203A of FIG. 2. The system then returns at Step 903 to the main operational program.

Figure 10:
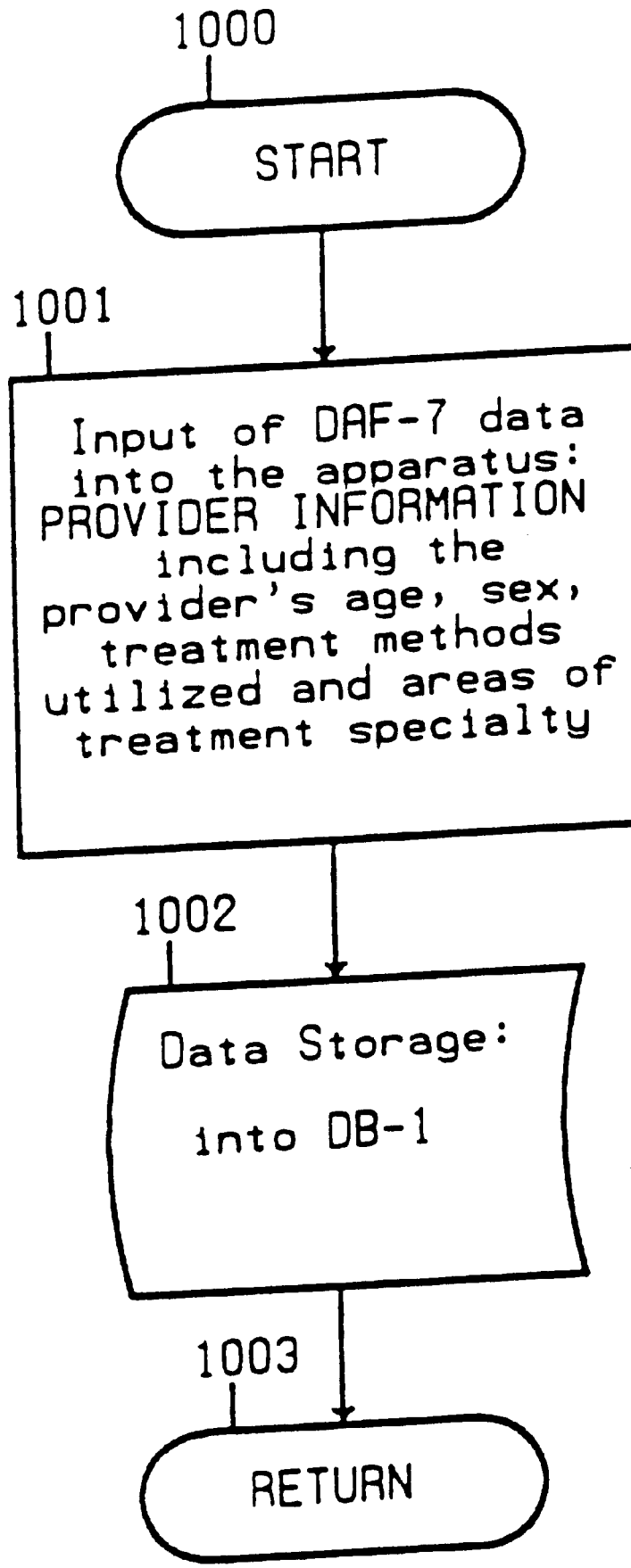
FIG. 10 illustrates an operational flow diagram of the method of the present invention which pertains to the input and storage of data from a seventh data acquisition means.

The obtaining and processing of the responses to the DAF-7 then occurs. FIG. 10 illustrates the processing and storage scheme for the DAF-7 data which takes place at Step 210 of FIG. 2. In the preferred embodiment of the present invention, the questions which comprise the DAF-7 are designed to obtain information pertaining to the assessed individual's provider including the provider's age, sex, area of licensure, address, phone number, areas of treatment expertise, and the treatment methods, techniques, and/or approaches the provider is skilled at utilizing, as well as other pertinent treatment information. utilized, medications administered, and the name of the facility wherein the assessed individual may be, or may have been hospitalized and/or in a treatment program, such as in a drug treatment center. In addition, questions pertaining to the provider's choice of treatment technique, method, and approaches to be utilized in treating the assessed individual are included. Following the commencement of the routine at Step 1000, the DAF-7 data is input via input device 4 into the apparatus 100 at Step 1001. The data is then stored at Step 1002 in the DB-1 database of the databank 8 of FIG. 1 at Step 203A of FIG. 2. The system then returns at Step 1003 to the main operational program.

Figure 11:
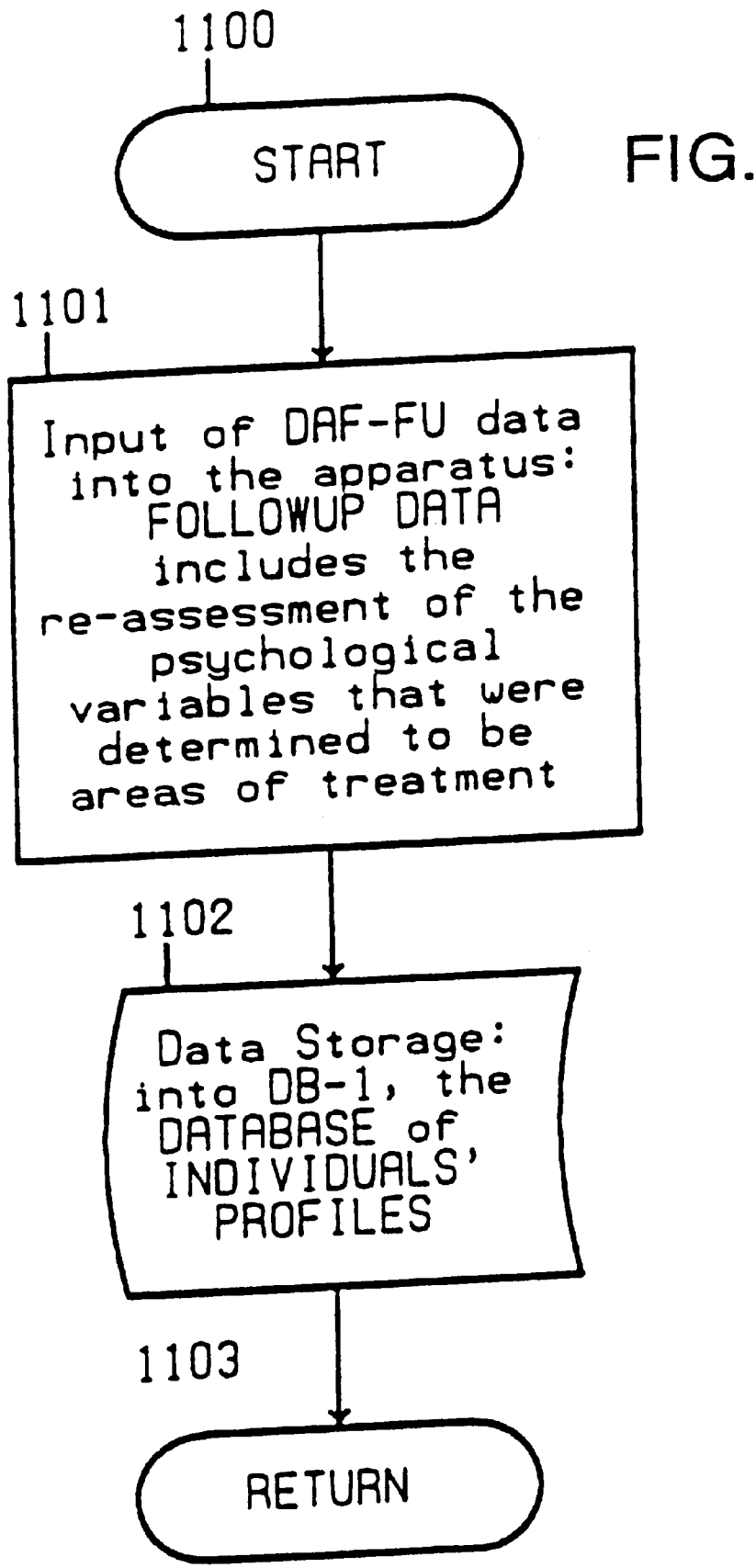
FIG. 11 illustrates an operational flow diagram of the method of the present invention which pertains to the input and storage of data from an eighth data acquisition means.

The obtaining and processing of the responses for a follow-up DAF, DAF-FU, may then occur depending upon the stage of treatment an assessed individual is currently in and depending upon whether such a follow-up is requested by the mental health care provider and/or payer. FIG. 11 illustrates the processing and storage scheme for the DAF-FU data which take place at Step 215 of FIG. 2. In the preferred embodiment of the present invention, the questions which comprise the DAF-FU are designed to obtain information from both the assessed individual and from the individual's provider pertaining to changes which may have occurred in and to the previously assessed psychological information during the course of treatment. As will be described in greater detail below, changes in the severity of the components of an assessed individual's psychological state of dysfunction are determined as are changes in suggested treatment methods and modes of treatment delivery. Following the commencement of the routine at Step 1100, the DAF-FU data is input via input device 4 into the apparatus 100 at Step 1101. The data is then stored at Step 1102 in the DB-1 database of the databank 8 of FIG. 1 at Step 203A of FIG. 2. The system then returns at Step 1103 to the main operational program.

The DAF's described above, in this regard, provide a means by which to obtain vital information from the assessed individual, health care provider and payer. While several of the DAF's are appended to this application and form a part thereof, it should be noted that the specific questions, information and response possibilities are subject to modification and revision so as to incorporate future developments in the use and application of the present invention as well as to incorporate future developments in the mental health care field or industry.

Referring once again to FIGS. 1 and 2, in the preferred embodiment, the data from the seven DAF's, along with the DAF-FU if utilized, is accessed by the apparatus 100 which retrieves relevant DAF data from the DB-1 database of databank 8 and enters the data into pre-assigned memory locations in the cells of various spreadsheets. Specifically, data from the DAF-1 is stored in the DB-1 database and is entered into cells in the DAF-1 spreadsheet as well as into pre-assigned cells in the DAS. It should be noted that data from the other DAF's is also stored in the DB-1 database and entered into various spreadsheets, including the DAS. The above spreadsheets are stored in the RAM device 3 during program operation. It is from these spreadsheets that the data output reports are generated, as will be described below.

It should be noted at this juncture, that it is the CPU 1 of the apparatus 100 of FIG. 1 which performs all of the previously described and hereinafter described data retrieval, data storage, data processing, and/or all operational functions performed during the operation of the present invention. Further, it should also be noted that virtually all of CPU 1 and apparatus 100 control is facilitated by computer programs and/or software programs and/or algorithms which are utilized to implement the method of the present invention.

In addition to the data in the DB-1 database, the data stored in the Database of Treatment Research and Techniques, DB-2, the Database of Providers, Hospital, & Treatment Programs, DB-3, and the Database of Payers, DB-4, is also retrieved and stored into pre-assigned data-cells of the DAS as per software instruction as described in greater detail below. It should be noted that the data in the DB-2 through DB-4 databases are entered, via input device 4 into the apparatus 100, into the respective databases at the processing center independently of the data which is acquired by the DAF's.

In the preferred embodiment of the present invention, the DB-2 database (the Database of Treatment Research and Techniques) includes an exhaustive survey of the findings of psychotherapy research process and outcome studies and theoretical information pertaining to the use of specific treatment methods, techniques, approaches, and/or programs. It is continually updated so that the most current research findings and treatment options in the field of mental health care are stored in the database and are utilized by the present invention.

The DB-2 database may be comprised of fields (i.e., groups of data) which include a "Level 1 Factor-Profile-Group type" (i.e., a group of statistically determined scores reflecting an assessed individual's aggregated DAF responses as determined by a first level factor analysis routine, etc.); a "Level 2 Factor-Profile-Group type" (i.e., a group of statistically determined scores reflecting an assessed individual's aggregated DAF responses accordingly as determined by a second level factor analysis routine, etc.); a "treatment-variable" (i.e., a specific psychopathological condition, such as depression, interpersonal problems or a sleep disturbance, which is determined to be a focus of treatment, etc.); the "Present-Severity-Score-Range of the treatment-variable", which indicates a range of treatment-variable severity-scores which correspond to the existing treatment-variables' severity-scores; the "Severity-Score-Goal-Value" which indicates the goal level below which the treatment-variables' severity-scores are to be reduced by the treatment, the "treatment-type" which indicates a general "school" of therapy or which indicates specific treatment methods, techniques, approaches and/or programs (e.g., Behavioral, Cognitive or Psychoanalytic psychotherapy or Psychopharmacological Medication type, etc.); "treatment-mode", which indicates how the treatment-type is to be delivered (e.g., for psychotherapy there may be an indication of outpatient individual, outpatient group, outpatient family, and/or inpatient treatment, etc., while the dosage may be indicated for the administration of Psychopharmacological Medication); "treatment-duration", which indicates the estimated length of time of treatment required to achieve the Severity-Score-Goal-Value; "Other Treatment Suggestions", which indicate ancillary treatment approaches such as self-help groups or structured physical health care programs; and, finally, "Specific Techniques", which indicate reference to detailed treatment techniques and procedures which may be utilized.

The DB-3 database (Database of Providers, Hospitals, & Treatment Programs) includes pertinent information pertaining to the providers of mental health care including identification data, areas of expertise, the treatment methods employed.

In the preferred embodiment of the present invention, the DB-4 database (the Database of Payers) includes information pertaining to the payers of mental health care treatment. Information in this database includes identification data, payment criteria, limitations to and of coverage, and "severity-score cutoff" values which will be described below.

As noted above, the data stored in the DB-2 database is also entered into the RAM device 3 at the processing center and is entered at Step 203B separately and independently of the data obtained from the DAF's. The data stored in the DB-3 database is also entered into the RAM device 3 at the processing center and is also entered at Step 203C separately and independently of the data obtained from the DAF's. The data stored in the DB-4 database is entered into the RAM device 3 at the processing center and is entered at Step 203D separately and independently of the data obtained from the DAF's. The data from all three of these databases is accessed by the CPU 1 of the apparatus 100 and is analyzed by the method of present invention at Step 204.

Referring once again to FIG. 2, once all of the data to be utilized from the DAF's and from the databases DB-1, DB-3 and DB-4 have been entered and stored in their respective databases at Steps 203 and 203A, the CPU 1 performs a series of processing routines, described in detail below, which results in data which is utilized in order to generate a series of reports which may be utilized by the health care providers and payers. The data can then be output by the output device 7 of FIG. 1 which may be a printer for producing hard copy reports. The hard copy reports can then be sent to the provider, payer and/or other customers or subscribers. Alternately, the output device 7 may be a modem or other electronic, telecommunication, and/or networking means which may be utilized for electronically transferring the output data or report data to the provider, payer and/or other customers or subscribers.

Data indicative of four separate reports may then be provided by the method and apparatus of the present invention. The four reports consist of an Individual Patient Profile (IPP) report, a Utilization Review (UR) report, an Individualized Treatment Plan (ITP) report and a Followup Utilization Review (FUR) report.

The Individual Patient Profile (IPP) report is generated at Step 211 in FIG. 2. In the preferred embodiment of the present invention, the IPP report describes the assessed individual's psychological profile in terms of precise and treatment-relevant objective measurements. These measurements, called "severity-scores", are calculated by downloading into the CPU 1 information from the present invention's Database of Assessed Individuals' Profiles, DB-1, and then by comparing an assessed individual's profile measurements with or against the severity-score measurements for the profiles of all other individuals stored in the DB-1. This analysis yields a series of severity-scores for each of the assessed individual's areas of psychological dysfunction which may then be utilized in order to determine the relative degree of the assessed individual's emotional discomfort, distorted or dysfunctional thinking and perception, and maladaptive behavior, etc. These severity-scores are statistically determined numbers which indicate how severe the assessed individual's state of dysfunction may be compared with other people.

In the preferred embodiment, a low score indicates that a particular problem is relatively mild or of a level experienced by most normal people in society. Also, in the preferred embodiment, a high score indicates that a particular problem is more severe than that experienced by most people. The IPP report may also include a summary and analysis of the assessed individual's bio-medical condition (medical illnesses, physical complaints, etc.), his or her cognitive, emotional and behavioral tendencies as they relate to different situations, the current environmental and social stressors he or she experiences, and significant historical and/or childhood data.

Further, the second report may also determine the degree of likelihood that the assessed individual and/or the provider are answering the pertinent questions accurately and honestly, which will be described in more detail below with reference to the UR report.

Figure 12:
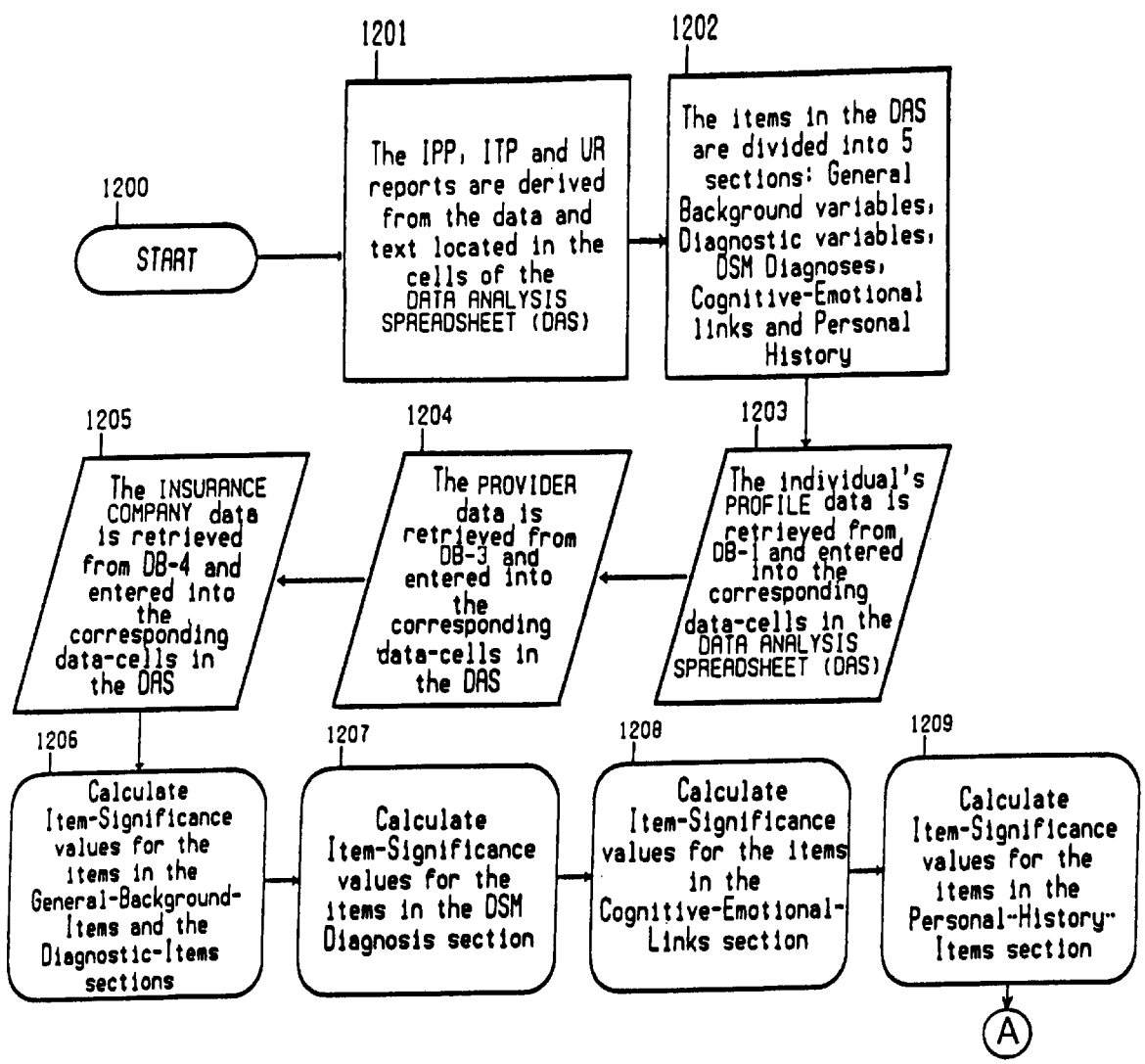
FIG. 12 illustrates an operational flow diagram of the method of the present invention which pertains to the data input and data processing for the generation of a first, a second, and a third output data report.
Figure 12B:
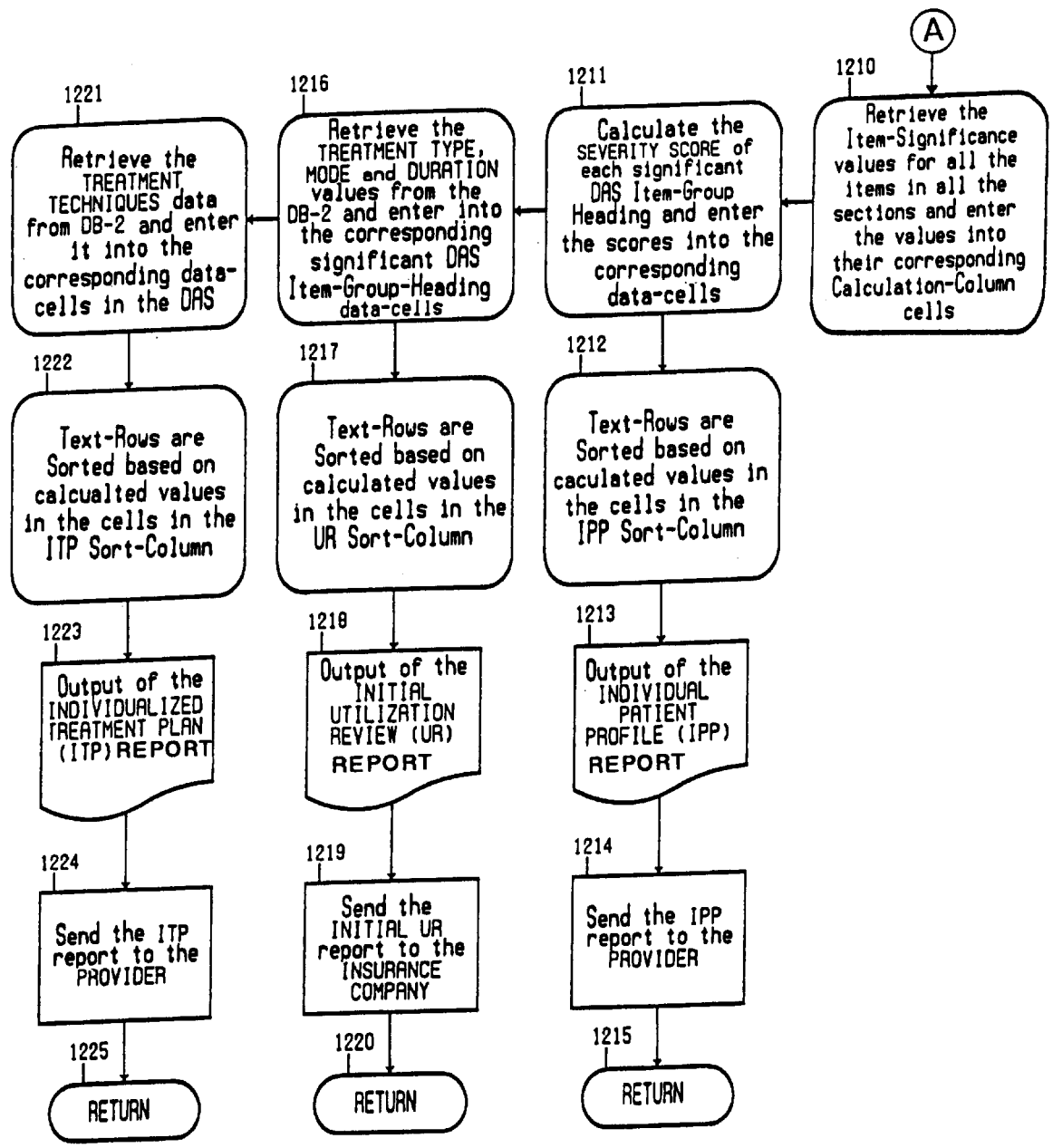

FIG. 12 illustrates the system operation for the generation of the Individual Patient Profile (IPP) report. The routine commences at Step 1200. Step 1201 denotes that the IPP report is derived from data and text which are located in cells within a spreadsheet, which may be the hereinbefore designated Data Analysis Spreadsheet (DAS). It should be noted that this process is similar to utilizing the DAF-1 Spreadsheet in order to perform the analysis of the DAF-1 data with the subsequent output data being of the form of the DAF-2, as described above. Step 1201 denotes that the DAS is divided into rows of items wherein each item is comprised of a row of text-cells adjacent to a series of data-cells.

At Step 1202, these items are divided into five logically determined sections which are designated: the "General-Backgroud-Items" section, the "Diagnostic-Items" section, the "DSM-Diagnosis" section, the "Cognitive-Emotional-Links" section and the "Personal-History-Items" section. These spreadsheet sections are typically defined as areas of the spreadsheet grid comprised of a Block of adjacent spreadsheet cells.

The General-Backgroud-Items section consists of groups of items which are assessed by the DAF-3 and the DAF-4 questions and which pertain to an assessed individual's age, sex, nationality, familial information, physical and medical information, and marital, occupational, and academic history. The Diagnostic-Items section consists of groups of items which are assessed by the DAF-1 through the DAF-4 questions and which pertain to diagnostically-relevant qualitative and quantitative aspects of an assessed individual's emotional, cognitive and behavioral tendencies, traits, characteristics and levels of functioning as well as to existing and former environmental stressors. The DSM-Diagnosis section consists of items chosen and grouped in diagnostic categories in accordance with the most current version of the American Psychiatric Association's *Diagnostic and Statistical Manual of Mental Disorders* (DSM). It should be noted that many of the items in this section are simply a re-arrangement of items which are identical to those items in the Diagnostic-Items section and, as such, are assessed by the DAF-1 through the DAF-4 questions. The Cognitive-Emotional-Links section consists of groups of items which are assessed by the DAF-1 and the DAF-2 questions and which pertain to an assessed individual's thoughts which are related to frustrated or failed goals and/or values and which pertain to the individual's concomitant or related emotions.

Finally, the Personal-History-Items section consists of groups of items which are assessed by the DAF-5 questions and which pertain to an assessed individual's childhood history. In this manner, the data from the DAF's are utilized in order to generate the above described spreadsheet data sections of the DAS.

At Step 1203, the assessed individual's profile data (i.e., all the DAF response data which has been previously stored in the DB-1 database) is retrieved and entered into predetermined data-cells in the Data Analysis Spreadsheet (DAS). In the preferred embodiments of the present invention, these scores are comprised of the assessed individual's, provider's, and/or payer's DAF response raw scores (i.e., the actual responses obtained from the various DAF questions). At Step 1204, the provider data, which has been previously stored in the DB-3 database is retrieved and entered into pre-determined data-cells in the pertinent portions of the abovedescribed sections of the DAS. At Step 1205, the payer data which has been previously stored in the DB-4 database is retrieved and entered into pre-determined data-cells in the pertinent portions of the abovedescribed sections of the DAS.

At Step 1206, the specified data, which have been retrieved from the DB-1, DB-3 and DB-4 databases, are then entered into the General-Background-Items and Diagnostic-Item sections of the DAS, as described above, wherein they undergo a series of mathematical calculations which compute the first of a series of values from the data, which is herein designated the "General-Background-Item-Significance" values and the Diagnostic-Item-Significance values. The General-Background-Significance and Diagnostic-Item-Significance values are then computed by formulas which are stored in pre-assigned DAS data-cells. These formulas instruct the CPU 1 of the apparatus 100 to first determine which of the item-scores are greater than or equal to a pre-determined statistical cutoff value or values. The data-cells which have item-scores which are greater than or equal to the cutoff value or values are then assigned either a value of "1" or another positive numerical value, which is derived by dividing or by multiplying the corresponding DAF raw-score by a specified numerical amount. On the other hand, the data-cells which have item-scores which are less than the cutoff value or values are assigned a value of "0".

At Step 1207, specific data is retrieved from the General-Background-Items and Diagnostic-Item sections of the DAS and is entered into corresponding data-cells in the DSM-Diagnosis section wherein the data undergoes a series of mathematical calculations which compute the second of a series of values from the data, herein designated the DSM-Diagnosis-Item-Significance values. The DSM-Diagnosis-Item-Significance values are computed by utilizing formulas which are stored in their respective DAS data-cells. These formulas instruct the CPU 1 of the apparatus 100 to first determine which of the item-scores are greater than or equal to a pre-determined statistical cutoff value or values. The data-cells which have item-scores which are greater than or equal to the cutoff value or values are then assigned either a value of "1" or another positive numerical value which is derived by dividing or by multiplying a corresponding DAF raw-score by a specified numerical amount. On the other hand, data-cells which have item-scores which are less than the cutoff value or values are assigned a value of "0".

At Step 1208, the specific data which has been retrieved the databases and which have been entered into the Cognitive-Emotional-Links section of the DAS, as described above, then undergoes a series of mathematical calculations which compute a third of a series of values from the data, which are herein designated as the "Cognitive-Emotional-Links-Significance" values. The Cognitive-Emotional-Links-Significance values are computed by formulas which are stored in pre-assigned DAS data-cells. These formulas then instruct the CPU 1 of the apparatus 100 to first determine which of the item-scores are greater than or equal to a pre-determined statistical cutoff value or values. The data-cells which have item-scores which are greater than or equal to the cutoff value or values are assigned either a value of "1" or another positive numerical value, which is derived by dividing or by multiplying the corresponding DAF raw-score by a specified numerical amount. On the other hand, data-cells which have item-scores which are less than the cutoff values are assigned a value of "0".

At Step 1209, the specified data which has been retrieved from the databases and which has been entered into the Personal-History-Items section of the DAS, as described above, then undergoes a series of mathematical calculations which computes a fourth of a series of values from the data, which are herein designated as the Personal-History-Items-Significance values. The "Personal-History-Items-Significance" values are computed by formulas which are stored in pre-assigned DAS data-cells. These formulas then instruct the CPU 1 of the apparatus 100 to first determine which of the item-scores are greater than or equal to a pre-determined statistical cutoff value or values. The data-cells which have item-scores which are greater than or equal to the cutoff value or values are assigned either a value of "1" or another positive numerical value, which is derived by dividing or by multiplying the corresponding DAF raw-score by a specified numerical amount. On the other hand, data-cells which have item-scores which are less than or below than the cutoff value or values are assigned a value of "0".

At Step 1210, the CPU 1 of the apparatus 100 is instructed to retrieve the General-Background-Item-Significance values, the Diagnostic-Item-Significance values, the DSM-Diagnosis-Item-Significance values, the Cognitive-Emotional-Links-Significance values and the Personal-History-Items-Significance values from their respective data-cell locations in the DAS and enter them into their corresponding pre-determined calculation-column cell locations in the DAS.

At Step 1211, item-group-heading severity-scores are then computed. As described earlier, severity-scores are values which are utilized in order to operationally define and to objectively determine the severity of an assessed individual's psychological state and/or state of dysfunction. In the preferred embodiment of the present invention, the actual numerical values, which constitute the severity-score scales, are calculated via statistical procedures which compare the assessed individual's aggregated item values, within each item-groups, to the aggregated item-group values of a large comparison group of other individuals. This comparison group is comprised of a data pool of all of the data from all of the individuals who have had their profile data stored in the DB-1 database. This data pool, however, does not, at this stage of the processing scheme, include the profile data from the individual being assessed. This data pool may also include the aggregated DAF acquired responses of all of the other "clinical" individuals (i.e., people who have been in treatment due to a psychological state of dysfunction) and the responses of the providers who have treated them, as well as the aggregated responses of a large sample of non-clinical individuals (i.e., people who have voluntarily responded to the DAF questions, but who are not in treatment and who are not functioning in a psychological state of dysfunction).

Thus, the severity-scores may be utilized in order to compare an assessed individual's and/or a provider's responses to those of the comparison group of other individuals in the DB-1 database in order to determine the severity of an assessed individual's psychological state of dysfunction in terms of important psychological information, and further, in relation to clinical and non-clinical comparison groups. It should further be noted that, as each assessed individual's responses are added to the DB-1 database, the comparison group and the clinical data group is ever-increasing in size. In this regard, the utilization of the present invention provides for a database which will grow with continued use and which will be ever-increasing in size.

For a visual representation of the Severity-score scale, refer to FIG. 14 at location 1400 which depicts a section of the DAS which comprises a possible format for three of the four possible data output reports which may be provided by the preferred embodiment of the present invention. In the preferred embodiment of the present invention, the severity-scores range from a low value of 1, which indicates that, based upon the responses of the assessed individual and/or the provider, the assessed individual's psychological state is similar to those of normal, well-functioning people, to a high score of 10, which indicates that the assessed individual's psychological state is similar to those of people who have severe psychological states of dysfunction. It should be noted that these severity-scores can easily be translated into percentiles, deviation scores, and/or other statistical values and/or indicators which may provide for a more meaningful indicator to the person or entity utilizing the report (i.e., the providers, payors, and/or other customers or subscribers).

Once calculated, the severity-score values are entered into corresponding data-cells, at location 1401, which are located adjacent to the significant item-group-headings as exemplified at positions 1402C and 1403C. It should also be noted that, in the preferred embodiment of the present invention, the DAF response raw scores (i.e., the assessed individual's actual numerical responses to the various DAF questions) are also entered into their corresponding data-cells at Steps 1203 through 1205 of FIG. 12, as this appears at location 1404 of FIG. 14.

Referring once again to FIG. 12, note that Step 1211 has two process arrows, wherein one arrow indicates that the apparatus may be directed to Step 1212 for the generation of the IPP report, the apparatus may also be directed by the other arrow to Step 1216 for the generation of the UR and/or ITP report. The purpose of illustrating two arrows in the flow diagram of FIG. 12 is that the Steps 1212 through 1215, which are necessary in the generation of the IPP report, can be skipped if the IPP report is not requested. If the IPP report is requested, then processing proceeds to Step 1212 where formulas which are stored in adjacent IPP-sort-column cells, are then utilized in order to instruct the CPU 100 of the apparatus 100 to add to the calculation-column cell values, sequentially descending numerals which are located in other adjacent cells. These summed sort-column cell values are then utilized in order to determine whether large cells of text and data-cells, which are located in other adjacent cells on the same row, will or should be included in the data output report(s). These cells of text, it should further be noted, comprise the actual alpha-numeric script which is utilized in order to formulate the data output report, such as item and item-group-heading text along with the data-cells, which include the assessed individual's DAF response scores and severity-scores. The rows of text-cells and data-cells are then sorted sequentially based upon the values which are stored in the IPP-sort-column cells.

The sorted rows of text-cells and data-cells are then output at Step 1213 by the apparatus 100 in order to produce the IPP report. The IPP report is generated by the output device 7 of FIG. 1 and is sent to the provider, payer and/or other customers or subscribers at Step 1214 via the various alternative means described above (i.e., printer hardcopy or via a modem) and the program operation continues at Step 1215. The report may also be sent to the provider, payer, customers and/or subscribers by means of the user interactive interface and delivery device which may be employed in an alternative embodiment of the present invention and which will be described below with reference to FIG. 15. At this point, the operation of apparatus 100 can be haulted or terminated, if desired, by going to Step 216 of FIG. 2. The instruction which may be utilized to terminate the operation of the present invention may be by input command by the user via the user command entry device 5, or this instruction may be entered into the apparatus via input device 4 at the time of data entry by utilizing the corresponding response to a DAF question regarding the haulting and/or termination of the processing routine.

The Utilization Review (UR) report is generated at Step 212 in FIG. 2. The UR report is sent to the payers of mental health care. The UR report is designed to assist payers in determining the most cost-effective and optimum quality type of treatment and mode of treatment delivery (i.e., whether treatment should be delivered via inpatient or outpatient means or methods, and whether treatment should be administered to the individual, couple, family and/or in a group therapy environment). Also included in the UR report is an assessment of the probable length of time (i.e., treatment duration) which may be necessary in order to reduce the severity-scores of each aspect of the assessed individual's psychological state of dysfunction to a specific predetermined level (i.e., an operationally defined "cut-off score").

The provider and/or the payer may request any arbitrary severity cut-off score, which is to be utilized in determining treatment type, mode, and duration. The provider or payer selected severity cutoff score may then be utilized in the generation of the UR report. For example, a provider or payer may ask for determinations with respect to the type, mode and estimated duration of treatment which would be required to reduce the severity-scores corresponding to an assessed individual's psychological state of dysfunction, to a level which is equal to or less than the severity-scores determined for 50 percent of the other individuals who have been assessed by the present invention and whose scores have been stored in the DB-1 database. The severity cutoff score of 50 percent is then utilized by the present invention, as will be described in more detail below, in order to make the determinations regarding the type, duration and frequency of the treatment.

The UR report also includes information which may be useful in matching provider characteristics with an assessed individual's needs. As will be described in greater detail below, this is accomplished by comparing the assessed individual's profile data with or against the Database of Providers, Hospitals, & Treatment Programs (DB-3). Criteria such as the provider's areas of specialty care, treatment skills and experiences, and treatment histories with similar types of individuals may also be included in the UR report so as to indicate the nature and degree of the provider/ assessed individual match.

Further, the UR report is capable of performing "validity checks" which may be utilized in order to determine the likelihood that the assessed individuals and/or the providers are answering the pertinent questions accurately and honestly. These "validity checks" can be accomplished by analyzing the assessed individual's responses to certain DAF questions which are designed to assess the individual's willingness to admit to socially unacceptable actions which virtually everyone sometimes engages in (such as gossiping and the telling of untruths), determining which DAF questions are responded to in a similar manner by virtually everyone and determining whether or not the assessed individual responds in a like manner to those questions. These "validity checks" may also be designed to compare the provider's DAF responses to the assessed individual's DAF responses on identical items in order to determine how close their responses coincide with one another, and to determine the responses of the assessed individual and the provider to certain questions which are logically consistent with other questions which are utilized in order to measure similar psychological constructs (e.g., if an assessed individual's responses indicate that he or she is depressed, socially fearful, distrustful and/or resentful of most people, it would be illogical for the individual to report that he or she is socially popular and outgoing). The failure of and individual to admit to performing certain common, normal, yet socially desirable acts, and/or the less similar the assessed individual's responses are as compared to other individuals, and/or the less the agreement between the provider and the assessed individual, and/or the greater the logical inconsistencies, then the greater the likelihood would be that the assessed individual and/or the provider has failed to respond accurately or honestly. These "validity check" determinations can also help to detect fraud in diagnosis and treatment of individuals.

FIG. 12 illustrates the system operation for the generation of the Utilization Review (UR) report. Steps 1200 to Step 1211, it should be noted, have already been described above in conjunction with the description of the generation of the IPP report routine. Although the UR report may be generated without having to first generate the IPP report, the initial eleven Steps of 1200 to 1211 are identical to, and are required for, the generation of both the IPP and the UR reports and thus, once performed, these Steps 1200 to 1211 need not be repeated in generating the UR report. Therefore, the description of the UR report routine will begin at Step 1216.

Note that Step 1216 has two process arrows in the flow diagram of FIG. 12, wherein one arrow points to Step 1217 and indicates that the apparatus may be directed to Step 1217 for the generation of the UR report, while the other arrow directs the apparatus to Step 1221 for the generation of the ITP report. The purpose for illustrating two arrows is that the Steps 1217 through 1220, which are necessary in the generation of the UR report, can be skipped if the UR report is not requested. If the UR report or the ITP report (which will be described in detail below) is requested, then processing proceeds to Step 1216. If the UR report is not requested, processing will proceed to Step 1221.

At Step 1216, the treatment-type, treatment-mode and treatment-duration values are retrieved by the CPU 1 of the apparatus 100 from the Database of Treatment Research and Techniques, DB-2. In the preferred embodiment, the determination of these values may be made by a review of existing mental health care treatment literature and research findings and from a review of one or more of a consensus of surveyed experts in the field of mental health care treatment. This procedure will involve the questioning of acknowledged experts in the various types (or "schools") of psychotherapy and psychopharmacology regarding how and for how long they would most likely treat individuals who are logically grouped in assessed individual-profile-groups by virtue of their having similar "significant" variables and severity-score ranges. In addition, a thorough review of mental health treatment care literature and research may also provide other types of suggested treatment alternatives for various assessed individual-profile-groups. All of this information may be stored, in the preferred embodiment of the present invention, in the Database of Treatment Research and Techniques, DB-2, of FIG. 2 at Step 203B in the form of alphanumeric values (with regard to treatment-type, treatment-mode and treatment-duration determinations) and in the form of text (with regard to treatment technique suggestions). It should be noted that the present invention may determine these values statistically, as described below, and/or via logical and rational analyses of the data. Further, it should also be noted that all such data which is to be incorporated into the DB-2 database may be input by inputting such data and information via input device 4 of the apparatus 100.

A determination of the treatment-type, the treatment-mode and the treatment-duration values obtained from, and for, a sufficient number of assessed individual's may also be based upon statistical factor analyses of the DAF response data. These analyses may aggregate (i.e., combine or group) the item-group variables into a relatively few number of factors as indicated in FIG. 3A at Block 303A. These factors may then be utilized in order to form a basis for determining how assessed individuals' variables (i.e., DAS item-group-heading scores) may be aggregated. These aggregated variable-scores, which represent an assessed individual's factor-scores, may then be utilized in order to determine the most cost-effective and optimum quality treatment type for that particular individual's psychological state of dysfunction.

An assessed individual's factor-scores may then enable or facilitate the determination of treatment type, treatment mode, and/or treatment duration by comparing an assessed individual's "factor-profile" (i.e., the way the individual's factor-scores are distributed) with the factor-profiles of other individuals. This may be accomplished by first grouping assessed individuals according to their factor-profiles which is possible since the assessed individuals whose factors have similar scores should most likely have similar factor-profiles. Treatment outcome and process data may then be statistically analyzed vis-a-vis the above-described factor-profiles. Treatment outcome and process data comprises data which is or may be indicative of changes in severity-scores, as a consequence of receiving psychotherapeutic treatment, across treatment-variables. It should be noted that a treatment-variable is defined as being an item-group-heading whose initial severity-score is severe enough to make it a focus of treatment.

By virtue of the above noted statistical analyses, it is possible to determine which treatments may result in the greatest reduction in the severity-scores of specified treatment-variables in the least amount of time and for the least amount of cost for individuals who may exhibit a particular type of factor-profile.

Cost-effective and optimum quality treatment, therefore, could be operationally defined as that treatment which produces the greatest reduction in severity-scores, for the greatest number of treatment-variables, in the least amount of time and with the least amount of expense, for an individual who possesses a specific factor-profile. Further, statistical analyses may also then be utilized in order to determine which types of factor-profiles may be grouped together as a function of their responsiveness to particular forms of treatment. The most cost-effective and optimum quality treatment for an individual possessing a factor-profile-group type which is within a particular group may then be determined by converting the assessed individual's factor-profile to a numerical value which reflects the factor-profile-group to which the assessed individual appears to belong. All of the above described information may then be stored, in the preferred embodiment of the present invention, in the Database of Treatment Research and Techniques, DB-2, of FIG. 2 at Step 203B in the form of alphanumeric values (with regard to treatment-type, treatment-mode and treatment-duration determinations) and in the form of text (with regard to treatment technique suggestions).

Regardless of whether the treatment-type, the treatment-mode and the treatment-duration values, which are stored within the DB-2 database, are determined by logical or statistical methods, the apparatus 100 may be instructed, at Step 1216 of FIG. 12, for the UR report, and/or at Step 1221 of FIG. 12, for the ITP report, to retrieve these values by matching the individual's assessed individual-profile-group or factor-profile-group type and the individual's significant variables with the corresponding fields in the DB-2 database. The respective treatment-type, the treatment-mode and the treatment-duration values may then be retrieved from the DB-2 database and may be assigned to appropriate pre-determined data-cells and/or text-cells in the Data Analysis Spreadsheet (DAS).

FIG. 14 depicts a possible format by which one or more possible types, modes and/or durations of treatments may be reported. A scale of psychotherapeutic treatment types, depicted at Location 1405, is indicated by a symbol (Roman numerals "I" through "VI" in the present example) in a pre-determined data-cell which is located adjacent to each significant variable as depicted at Location 1406. A possible format by which one or more possible treatment modes, as listed in a scale of psychotherapeutic treatment types, as depicted at Location 1407, may be indicated by a symbol (capital letters "A" through "E" in the present example) in a pre-determined data-cell which is located adjacent to each significant variable as depicted at Location 1408.

The duration of treatment, that is, on the average, the amount of treatment time which is required for an assessed individual, having specific initial severity-scores, to improve (i.e., to have a desired severity-score reduction) to a severity-score level which may be below a pre-specified cutoff value or point, may also be reported. The cutoff value or point, depicted at Location 1409 of FIG. 14, may arbitrarily be determined by the payer and/or the provider, or it may be statistically determined for a given group or for the general population, whichever the protocol may be. A possible format by which possible treatment durations may be determined., in terms of outpatient psychotherapy hours, weeks of psychotropic medication, and/or weeks of inpatient hospitalization, as listed in a scale of treatment durations, as depicted at Location 1410, may be indicated by a symbol (e.g., lower case letter "a", for less than 5 units of care, through lower case letter "m", for over 60 units of care, in the present example) which is stored in a pre-determined data-cell which is located adjacent to each significant variable as depicted at Location 1411.

A possible format by which psychopharmacological suggestions may be made is depicted at Location 1412, wherein classes of medication are indicated by a number ("1" through "8" in the present example) in a predetermined data-cell, which is adjacent to each significant variable, as depicted at Location 1413. It should be noted that additional statistical analyses are also envisioned which may provide for the determinations of specific types and dosages of medication within each class of treatment. In this manner, both the necessity of the psychopharmacological treatment and the specific class, types and dosages of the drug(s) which may be administered, may then be determined.

In addition, treatment suggestions concerning the assessed individual's physical health, other forms of support services (i.e., self-help groups, etc.), contraindications to specific kinds of treatment (i.e., when not to use certain treatments, etc.) and the indication of warnings (i.e., the potential for the assessed individual's doing harm to him or herself or to others, etc.) may be reported. FIG. 14 depicts a possible format by which such information may be listed on a scale which may be labeled "Other Information" as depicted at Location 1414, and which may be indicated by a symbol (lower case Roman numerals "i" through "iii" in the present example) in a pre-determined data-cell which is located adjacent to each significant variable as depicted at Location 1415.

Other information (not shown), but nevertheless included in the UR and IPP reports, include an "Overall Level Of Vocational And Psycho-Social Functioning Impairment As A Result Of Psychological Disturbance" score, which may be based upon a weighted sum of all of the psychological variables which may be affecting the assessed individual and which may be interfering with the individual's ability to function adequately. Finally, the "validity check" analyses, described above, may also be included in the UR and IPP reports.

Returning once again to FIG. 12, at Step 1217, formulas which are stored in the UR-sort-column cells instruct the CPU 1 of the apparatus 100 to add to the calculation-column cell values, sequentially descending numerals which are stored in other adjacent cells. The summed sort-column cell values which result may be utilized in order to determine whether large cells of text, which are located in other adjacent cells on a same row, will be included in the data output report. These cells of text, it should further be noted, comprise the actual alpha-numerical text which may be utilized in forming the data output report, including the assessed individual's DAF response scores, severity-scores, item and item-group-heading text, and treatment-type, treatment-mode, treatment-duration and other treatment-relevant information. The rows of text may then be sorted sequentially based upon the values which are stored in the UR-sort-column cells. The sorted rows of text may then be output, at Step 1218, by the apparatus 100 in order to produce the UR report. The UR report may then be output via the output device 7 in FIG. 1 which may be a printer, a modem, or other suitable device. The UR report may then be sent to the providers, the payers, the customers, and/or the subscribers, at Step 1219, and the program operation continues at Step 1220. The report may also be sent to the provider, payer, customers and/or subscribers by means of the user interactive interface and delivery device which may be employed in an alternative embodiment of the present invention which will be described below and with reference to FIG. 15. At this point, the operation of apparatus 100 can be haulted, if desired, by going to Step 216 of FIG. 2. The instruction which may be utilized to terminate the operation of the present invention may be by input command by the user via the user command entry device 5, or this instruction may be entered into the apparatus via input device 4 at the time of data entry by utilizing the corresponding response to a DAF question regarding the haulting and/or termination of the processing routine.

The Individualized Treatment Plan (ITP) report is generated at Step 213 in FIG. 2. The ITP report provides a detailed treatment plan, including a list of treatment goals and suggestions as to which treatment techniques or approaches (including specific types of psychotherapy and psychopharmacology-medication) may likely be the most cost-effective and optimum quality in treating each aspect of the assessed individual's psychological state of dysfunction. While the ITP report may be similar to the UR report, it is more detailed regarding treatment specifics which may include, but not be limited to, suggested specific treatment methods, techniques, approaches, and/or programs, technical references research findings to support such treatment options, etc.

FIG. 12 illustrates the system operation for the generation of an Individualized Treatment Plan (ITP) report. Steps 1200 to Step 1211, as described above in the description of the IPP and the UR report routines, are also utilized in generating the ITP. While required in generating the ITP report, Steps 1200 to Step 1211, in order to prevent repetition, will not be described again below. Although the ITP report may be generated without having to first generate the IPP and/or the UR reports, Steps 1200 to 1211 and Step 1216 must be performed in order to generate the ITP report. The ITP report generation routine begins at Step 1221.

It should be noted at this juncture, that while the present invention may generate IPP, UR and ITP reports, such report generation is optional. That is, a user may select any one or all of such reports via appropriate commands which may be entered via the user command entry device 5. Further, if the input of an individual's DAF response data is all that is desired, no report may be requested and, therefore, no report would be generated.

At Step 1221 of FIG. 12, the apparatus 100 is instructed, in the preferred embodiment of the present invention, to retrieve Treatment Techniques data from the DB-2 database and to enter the data into corresponding data-cells in the Data Analysis Spreadsheet (DAS). The ITP portion of the DAS is divided into a number of sections, each of which utilizes different criteria by which to provide a custom treatment plan which addresses the specific needs of the assessed individual in terms, and with techniques, which are relevant to the specific schools of mental health care treatment. The treatment plan sections include, but are not limited to, the following treatment plans and treatment techniques:

1. Cognitive-Behavioral treatments such as "Transactional Problem-Solving", which may include the treatment methods of problem identification, goal setting, the assessment of emotional-coping and/or active problem-solving strategies, the generation of alternative solutions, the evaluation of the best solution, and the implementation of the solution and the assessment of its effectiveness, and "Cognitive Restructuring" which assists the assessed individual to change his or her cognitive-emotional links.

2. Behavioral treatments such as "Systematic Desensitization", which may be utilized in order to reduce phobias, and "Behavior Modification" which utilizes rewards and punishments in order to change behavior.

3. "Psychoneurolinguistic" techniques which may be utilized in order to modify self-defeating behaviors and attitudes.

4. The use of "Paradoxical Intervention" techniques which may be utilized in order to break treatment deadlocks.

5. "Reframing" techniques which may be utilized in order to redefine the way in which a situation is viewed.

6. "Family Systems Restructuring" techniques which may be utilized in order to modify the way members of a family interact.

7. "Social Skills Training" techniques which may include the development of assertiveness skills and the ability to engage in effective interpersonal dialogue (i.e., communication skills training).

8. Psychoanalytic psychotherapy treatment plans which may include "Self Psychology" and "Short-Term Dynamic" therapeutic techniques and strategies.

9. The use of Hypnosis, "Systematic Relaxation", "Imaginal" and "Regressive" techniques.

In addition, the ITP report may list references to specific research findings upon which the various treatment plans and/or suggestions pertaining to specific treatment methods, techniques, approaches, and/or programs may have been made. The choice of which treatment plan and of the related techniques, which are to, or which may be reported, in the ITP report, may also be based upon both the provider's and/or the payer's request as well as upon the assessed individuals-profile-group values and the treatment-variables and severity-score values described above. The request for a specific treatment plan type (i.e., a treatment plan generated in accordance with a specified treatment type) may be made via the questions illicited in the DAF-6 and/or the DAF-7 wherein such data may have been entered as values, hereinafter designated the treatment-choice values, which may then be stored in the DB-1 database as described above. By matching the treatment-choice retrieval values, the assessed individual-profile-group values, the treatment-variable and the severity-score values, with the values in the corresponding fields in the Database of Treatment Research and Techniques, DB-2, the data from the DB-2 database may then be retrieved and entered into pre-determined cells in the Data Acquisition Spreadsheet at Step 1221 of FIG. 12.

At Step 1222, the formulas which are stored in the ITP-sort-column cells then instruct the CPU 100 of the apparatus 100 to add to the calculation-column cell values, sequentially descending numerals which are located in adjacent cells. The resulting values, defined as the summed sort-column cell values, are utilized in order to determine whether large cells of text, which are located in adjacent cells on a same row, will be included in the ITP report. These cells of text, it should further be noted, comprise the actual alpha-numeric text which are utilized in forming the ITP output report, which includes the assessed individual's DAF response scores, the severity-scores, the item and the item-group-heading text, and the text depicting the treatment plan and treatment techniques. The rows of text may then be sorted sequentially based upon the values stored in the ITP-sort-column cells. The sorted rows of text may then be output at Step 1223 by the apparatus 100 in order to produce the ITP report.

The ITP report is then sent to the providers, by any of the above describe methods, at Step 1224, and the program operation continues at Step 1225. The report may also be sent to the providers and/or other customers or subscribers by means of the user interactive interface and delivery device which may be employed in an alternative embodiment of the present invention which will be described below and with reference to FIG. 15. At this point, the operation of apparatus 100 can be haulted or terminated, if desired, by going to Step 216 of FIG. 2. The instruction which may be utilized to terminate the operation of the present invention may be by input command by the user via the user command entry device 5, or this instruction may be entered into the apparatus via input device 4 at the time of data entry by utilizing the corresponding response to a DAF question regarding the haulting and/or termination of the processing routine.

Followup assessments may also be performed by the present invention by utilizing a Followup Data Acquisition Form (DAF-FU). The data obtained from the DAF-FU may be utilized to generate Followup Utilization Review (FUR) reports. By using follow-up DAF's at various time intervals, treatment progress and outcome may be determined and reported in the FUR report. The FUR report may typically indicate, among other things, changes in the assessed individual's severity-scores, as a consequence of treatment, the amount of treatment time remaining, treatment modifications and the cumulative cost of treatment.

Figure 13:
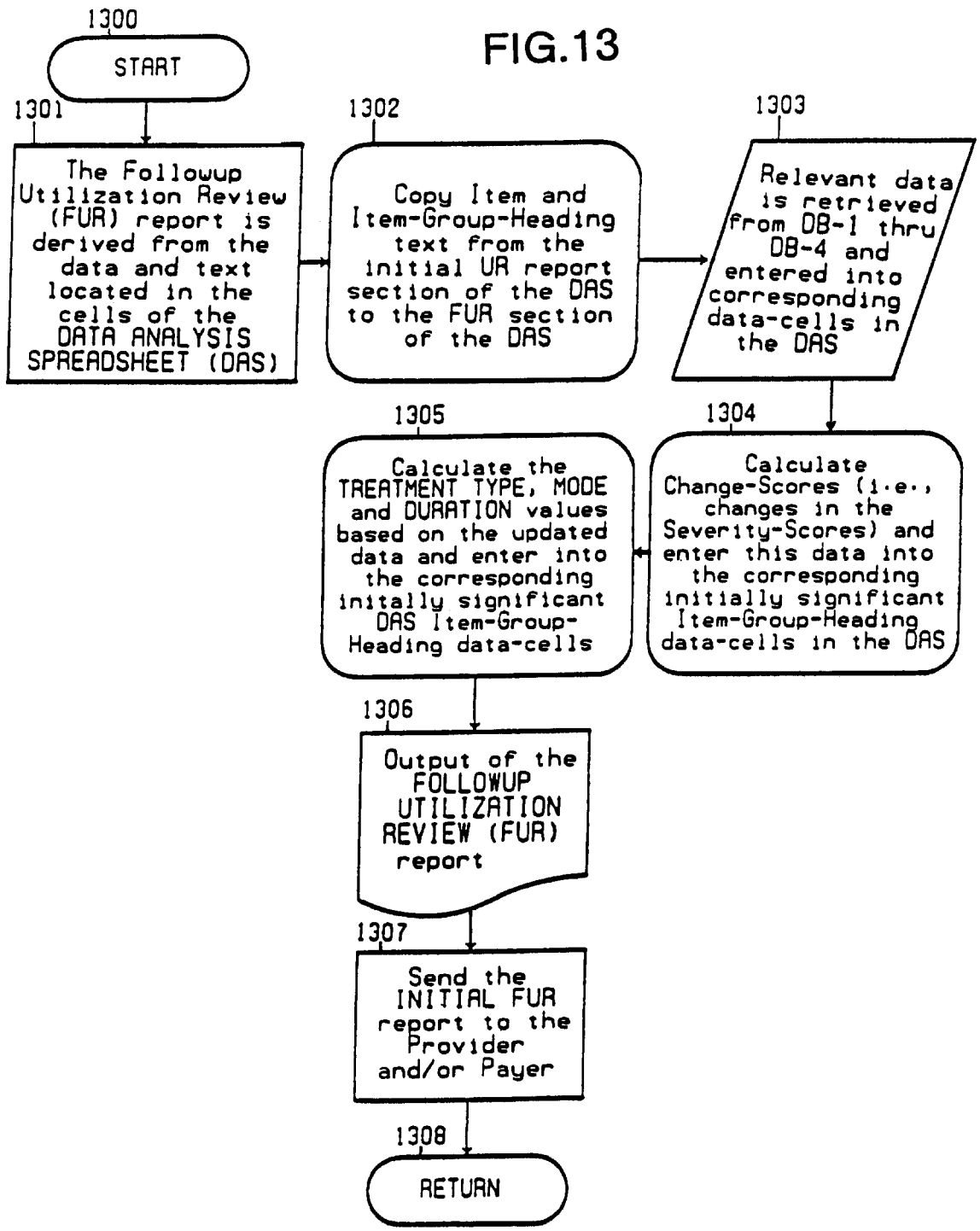
FIG. 13 illustrates an operational flow diagram of the method of the present invention which pertains to the data input and data processing for the generation of a fourth output data report.

FIG. 13 illustrates the system operation for the generation of the Followup Utilization Review (FUR) report. The routine commences at Step 1300. At Step 1301, in the preferred embodiment of the present invention, the FUR report is derived from data which is or may be stored in the DAS which was utilized in the generation of the IPP, the UR and the ITP reports. At Step 1302, the apparatus 100 copies the item text-cells (i.e., the cells of text corresponding to each significant item and item-group-heading) of the previously sorted UR report section of the DAS, generated at Step 1218, to the FUR report section of the DAS.

At Step 1303, the apparatus 100 is then instructed to retrieve the data from the DB-1 through DB-4 databases, including the previous and the most recent item and item-group-heading severity-scores and Treatment-Techniques Retrieval values. This data may then be entered into corresponding data-cells in the FUR section of the DAS. At Step 1304, changes in the severity-scores, for the items and item-group-headings which were determined to be significant during the initial analysis of the DAF-1 through the DAF-5 response data, are then calculated by subtracting the initial severity-scores from the severity-scores which were determined by the DAF-FU for each of the items and the item-group-headings. These "change scores" may then be entered into corresponding data-cells in a FUR section of the DAS.

At Step 1305, the treatment-type, the treatment-mode and the treatment-duration values may then be computed by using the most recent severity-score data and by following the same procedure as described above at Step 1216 of FIG. 12, which was employed in generating the UR report. In addition, an assessed individual satisfaction index may be computed via questions from the DAF-FU.

At Step 1306, the rows containing the assessed individual's DAF-FU response scores, severity-scores, severity-change-scores and item and item-group-heading text which comprise the FUR report, may then be output by the apparatus 100 by any of the above described techniques or devices in order to generate the FUR report. The FUR report may be sent to the providers, payers, and/or other customers or subscribers at Step 1307 and then the program operation continues at Step 1308. The report may also be sent to the provider, payer, customer and/or subscriber by means of the user interactive interface and delivery device which may be employed in an alternative embodiment of the present invention which will be described below and with reference to FIG. 15. At this point, the operation of apparatus 100 can be haulted or terminate, if desired, by going to Step 216 of FIG. 2. The instruction which may be utilized to terminate the operation of the present invention may be by input command by the user via the user command entry device 5, or this instruction may be entered into the apparatus via input device 4 at the time of data entry by utilizing the corresponding response to a DAF question regarding the haulting and/or termination of the processing routine.

Once the IPP, the ITP, the UR, and the FUR (if applicable) reports have been generated, the system operation is completed at Step 216 in FIG. 2. The above process may then be repeated for the next assessed individual routine or for the next follow-up routine. In this instance, user friendly means may appear on the display device to which the user may respond.

Figure 15:
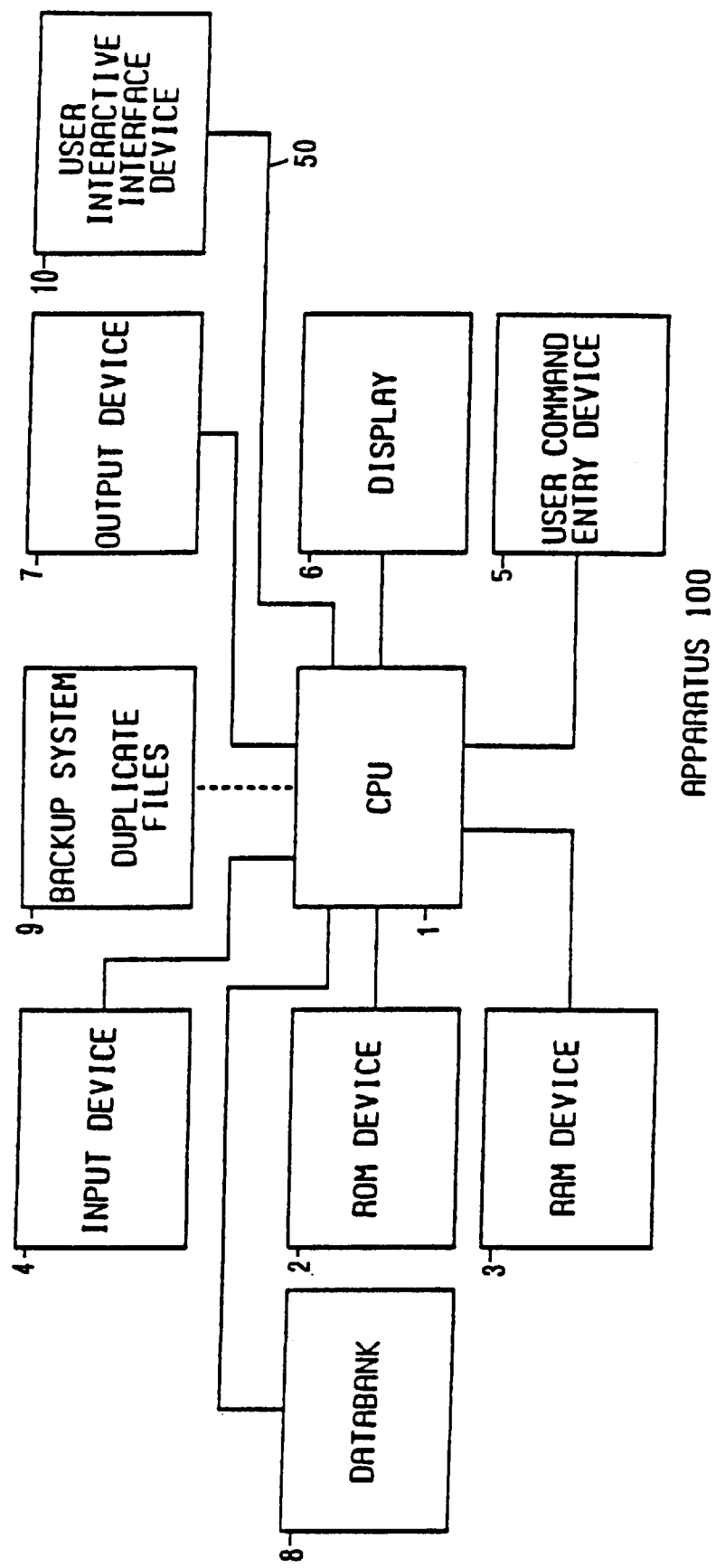
FIG. 15 illustrates an alternative embodiment of the present invention wherein the present invention may utilize a user interactive interface and display device which may allow multiple users to utilize the present invention from remote locations.
Figure 16:
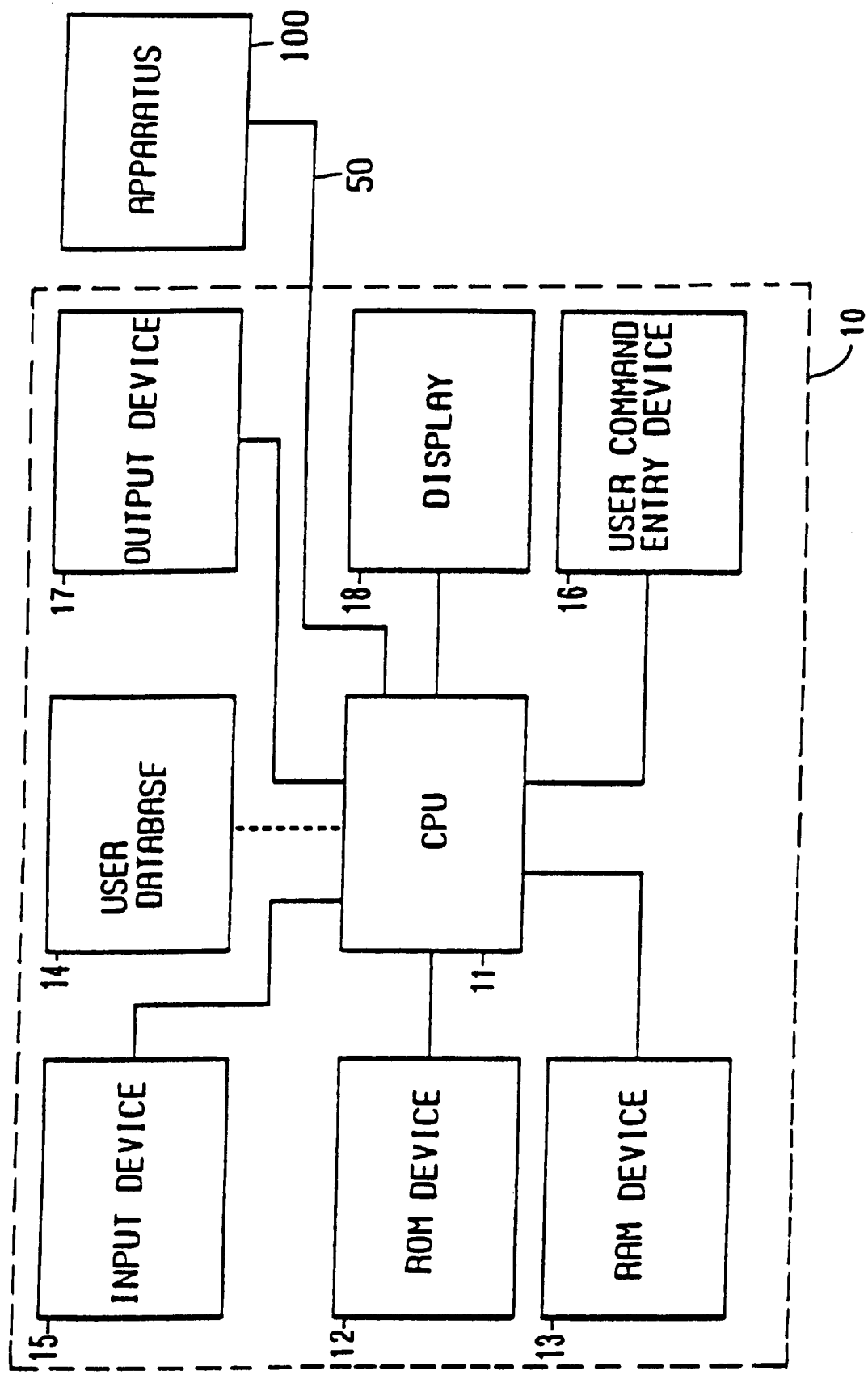
FIG. 16 illustrates a preferred embodiment of the user interactive interface device of FIG. 15 illustrating the components thereof.

FIG. 15 illustrates an alternate embodiment of the present invention. The alternate embodiment of the present invention as illustrated in FIG. 15 further comprises a user interactive interface and delivery system 10. FIG. 16 illustrates a preferred embodiment of the user interactive interface and delivery system 10 illustrating the components thereof. The user interactive interface and delivery system 10 may be a separate computer which may contain CPU 11, ROM 12 and RAM 13 memory devices, and/or user databases 14, data input 15 and user command entry 16 devices, which may include a keyboard, a mouse, and/or a modem or any other suitable device, a data output device 17 which may be a printer or any other suitable device for obtaining, receiving or storing data output reports and user display 18. The user interactive interface and delivery system 10 is designed to be utilized by remote users such as providers, payers, customers and/or subscribers and is further designed to be located at remote locations such as at the locations of the abovedescribed users. The user interactive interface and delivery device 10, may be interfaced with the apparatus 100 of the present invention either via a communication link 50 which may be a telecommunication means and/or other suitable communication networks which may include direct communication link-ups and/or radio communication link-ups via transmitting and/or satellite communication systems or means.

The user interactive interface and delivery device 10, in the embodiment of FIG. 15, provides a means by which to allow a remote user, as defined above, to access the apparatus 100. This may allow for a direct transmission of responses, to the DAF's, to be entered via any suitable data entry means located at the user's location. It may also provide for an instantaneous processing of the data from DAF-1 with a corresponding direct transmission to the user via the user interactive interface delivery device 10 of the DAF-2 so that the DAF-2 may be expeditiously administered to the individual and so that the responses of same may also be transmitted to the apparatus. All further DAF data may be transmitted via the user interactive interface and delivery system 10 so as to facilitate a complete operation of the present invention from any remote user location. It should be noted that adequate precautions are to be taken, in this alternative embodiment, so as to prevent a non-authorized user from interfering with data stored in any of the databases DB-1 through DB-4. Any of the DAF's, such as the DAF-2, and any of the reports, such as the IPP, the UR, the ITP and the FUR reports, if desired, may be electronically transmitted to the user via the user interactive interface and delivery device 10 wherein the report or reports may be output via the output means (not shown), which may be a printer, or wherein said report data may be stored in a user memory device.

Utilization of the user interactive interface and delivery system 10 in the embodiment of FIG. 15 may be accompanied by a security scheme or means whereby the user may be required to input a user password or access code in order to access the system. Any other suitable security system may also be utilized to safeguard the apparatus 100 of the present invention as well as a user's files and/or other interests. The security scheme or means may also be provided to ensure security and confidentiality of individual and/or user information. Further, the device 10 allows for an expedited data entry process as the data may be entered directly and/or instantaneously into the apparatus 100 and stored in a separate file which may be serviced by an ancillary program which will accept and monitor data entry so as to ensure that the requisite data, or complete data, for a given DAF or input routine is entered into the apparatus 100 before processing continues.

The user interactive interface and delivery device 10 also facilitates the management of numerous individual files at the same time. Users may also obtain grouped information for their individuals. Such grouped data or information may be provided as a separate processing routine in the method of the present invention. In this manner, the user interactive interface and delivery device 10 provides for an easy and convenient access to individual data and may facilitate enhanced record keeping arrangements as or information well as group information data which may be utilized by the user.

Further, the apparatus 100 of the present invention may be adapted to service multiple users over multiple channels in a network environment such as in local area networks (LANS) as well as wide area networks (WANS) wherein the present invention may be utilized over communications and/or long distance communication lines or systems such as telephone networks (phone lines) and/or radio communication and/or satellite communication networks. In the alternate embodiment, the CPU 1 of the apparatus 100 must be designed to operate over multiple channels or to process data and service users over multiple channels or lines. In this manner, the present invention may be utilized in a network environment which may service multiple users simultaneously, or nearly simultaneously, such as in a time-sharing system.

In another embodiment of the present invention, the user interactive interface and delivery system 10 may be employed to allow a user access to unsecured databases, or portions thereof, which may be stored in the databank 8 of the apparatus 100 or which may be used in association with the present invention. The user interactive interface and delivery device 10 therefore may also provide for a means by which the present invention may be utilized as an on-line database for psychological and/or psychopathological data and/or other pertinent information and along with information which may be of further valuable assistance to the above described users. In this manner it can be seen that the present invention, which may be utilized in conjunction with network systems described above, can be utilized for providing vast amounts and varieties of psychological and/or psychopathological data along with data processing and/or other pertinent information. In this regard, the potential users and utilization of the present invention may be limitless. The present invention may also be adopted for use in and/or in conjunction with other fields, including, but not limited to the medical field.

It should also be noted at this point that, in the preferred embodiment of the present invention, macro-commands (macros) are employed in order to control the sequential processes of inputting data into the various databases and spreadsheets, in the data processing by the apparatus 100 and the generation of output data. In the preferred embodiment, the macros may, for instance, be written in macro command language which may be compatible with the digital computer system utilized.

The output data and report data provided by the present invention may be utilized to assist payers and providers in formulating diagnosis and treatment plans. Further, the output data and report data provided may be utilized in assisting payers and providers in the monitoring of mental health care claims so as to prevent fraudulent claims and other related problems which are prone to arise in the business operation of payers and providers in the mental health care field and industry, The wealth of psychological and/or psychopathological data and/or other pertinent information which may be accumulated by and stored within the databases of the present invention may also be analyzed in such a manner so as to yield vital actuarial data which may be made available to payers and various other interested parties, or other interested industries or organizations, for actuarial purposes. The objective data which is provided by the present invention may be provided and may be made available for use in the fields of law, bio-medicine, psychology, psychiatry, and government, among others. Further, the utilization of the above data in research, decision-making and litigation also envisioned. All such analyses may be normative, that is, based upon the analyses of groups of data. Also, the present invention may be designed so as to provide the most stringent safeguards of the data obtained thereby and therefrom so as to preserve confidentiality and anonymity of the assessed individuals as well as the confidentiality of the many different types of users.

While the present invention has been described in preferred embodiments, such are only meant to be illustrative of same and are not to be construed as limitations thereof. Accordingly, the present invention includes all modifications and/or variations of the embodiments described herein with the scope of the invention limited only by the claims which follow.

1. Which of the following things do you think about:
   (a) having PHYSICALLY (BODILY) PAIN, being HURT, or being INJURED? ........ [Y]
   (b) having a PHYSICAL HANDICAP or becoming HANDICAPPED? ................ [Y]
   (c) having a LEARNING DISABILITY ............................................. [Y]
   (d) having a SERIOUS PHYSICAL ILLNESS or DISEASE? ........................ [Y]
   (e) having a SERIOUS EMOTIONAL or MENTAL ILLNESS? ..................... [Y]
   (f) DYING? ................................................................... [Y]

If you answered YES to any of the above, then *how often* do you usually think about those things:
      *NOT AT ALL* [0] [1] [2] [3] [4] [5] [6] [7] [8] *A GREAT DEAL*

When you think about these things, *how strongly* do you feel the following emotions:

ANNOYED or DISAPPOINTED
     with Yourself ............. [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or  ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY  ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL*  ... [0] [1] [2] [3] [4] [5] [6] [7] [8]

2. Which of the following things do you think about:
   (a) being REJECTED by certain people? .......................................... [Y]
   (b) being RIDICULED by certain people? ......................................... [Y]
   (c) NOT having enough LOVE? ................................................. [Y]
   (d) NOT having enough AFFECTION or SEX? .................................... [Y]
   (e) NOT being ACCEPTED by certain people? .................................... [Y]
   (f) NOT having the APPROVAL of certain people? ............................... [Y]
   (g) NOT having the RECOGNITION of certain people? ........................... [Y]

If you answered YES to any of the above, then *how often* do you usually think about those things:
      *NOT AT ALL* [0] [1] [2] [3] [4] [5] [6] [7] [8] *A GREAT DEAL*

When you think about these things, *how strongly* do you feel the following emotions:

ANNOYED or DISAPPOINTED
     with Yourself ............. [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or  ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY  ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL*  ... [0] [1] [2] [3] [4] [5] [6] [7] [8]

Appendix A

< page 1 > continued on back

3. Do you think about the following:
    NOT HAVING (or KEEPING) ENOUGH MONEY or POSSESSIONS? ........... [Y]

If you answered YES to the above, then *how often* do you usually think about it:

NOT AT ALL [0] [1] [2] [3] [4] [5] [6] [7] [8] A GREAT DEAL

When you think about this, *how strongly* do you feel the following emotions:

ANNOYED or DISAPPOINTED
   with Yourself ............. [0] [1] [2] [3] [4] [5] [6] [7] [8]
* *ANGRY at Yourself* ........ [0] [1] [2] [3] [4] [5] [6] [7] [8]
* *ASHAMED/EMBARRASSED* [0] [1] [2] [3] [4] [5] [6] [7] [8]
* *GUILTY or REMORSEFUL* . [0] [1] [2] [3] [4] [5] [6] [7] [8]

ANNOYED or DISAPPOINTED
   with Other People or ...... [0] [1] [2] [3] [4] [5] [6] [7] [8]
   the Circumstances
* *ANGRY* ................. [0] [1] [2] [3] [4] [5] [6] [7] [8]

SAD or UNHAPPY ......... [0] [1] [2] [3] [4] [5] [6] [7] [8]
* *DEPRESSED* ............. [0] [1] [2] [3] [4] [5] [6] [7] [8]

CONCERNED or UNEASY ... [0] [1] [2] [3] [4] [5] [6] [7] [8]
* *ANXIOUS or FEARFUL* ... [0] [1] [2] [3] [4] [5] [6] [7] [8]

4. Which of the following things do you think about:
   (a) OTHER PEOPLE being PHYSICALLY HURT or ILL? ......................... [Y]
   (b) OTHER PEOPLE being EMOTIONALLY ILL or UPSET? ..................... [Y]
   (c) OTHER PEOPLE DYING? ................................................. [Y]

If you answered YES to any of the above, then *how often* do you usually think about those things:

NOT AT ALL [0] [1] [2] [3] [4] [5] [6] [7] [8] A GREAT DEAL

When you think about these things, *how strongly* do you feel the following emotions:

ANNOYED or DISAPPOINTED
   with Yourself ............. [0] [1] [2] [3] [4] [5] [6] [7] [8]
* *ANGRY at Yourself* ........ [0] [1] [2] [3] [4] [5] [6] [7] [8]
* *ASHAMED/EMBARRASSED* [0] [1] [2] [3] [4] [5] [6] [7] [8]
* *GUILTY or REMORSEFUL* . [0] [1] [2] [3] [4] [5] [6] [7] [8]

ANNOYED or DISAPPOINTED
   with Other People or ...... [0] [1] [2] [3] [4] [5] [6] [7] [8]
   the Circumstances
* *ANGRY* ................. [0] [1] [2] [3] [4] [5] [6] [7] [8]

SAD or UNHAPPY ......... [0] [1] [2] [3] [4] [5] [6] [7] [8]
* *DEPRESSED* ............. [0] [1] [2] [3] [4] [5] [6] [7] [8]

CONCERNED or UNEASY ... [0] [1] [2] [3] [4] [5] [6] [7] [8]
* *ANXIOUS or FEARFUL* ... [0] [1] [2] [3] [4] [5] [6] [7] [8]

< page 2 > continued on next page

5. Which of the following things do you think about:
   (a) how certain people DON'T CARE WHAT YOU SAY? .......................... [Y]
   (b) how certain people DON'T DO WHAT YOU WANT? .......................... [Y]
   (c) how certain people DON'T RESPECT YOU? .................................. [Y]
   (d) how certain people DON'T UNDERSTAND or CARE HOW YOU FEEL? ......... [Y]

If you answered YES to any of the above, then *how often* do you usually think about those things:
           *NOT AT ALL* [0] [1] [2] [3] [4] [5] [6] [7] [8] *A GREAT DEAL*

When you think about these things, *how strongly* do you feel the following emotions:

ANNOYED or DISAPPOINTED
     with Yourself ............. [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL* ... [0] [1] [2] [3] [4] [5] [6] [7] [8]

6. Which of the following things do you think about:
   (a) how YOU CAN'T DEPEND ON certain people? ............................... [Y]
   (b) how YOU CAN'T TRUST certain people? ..................................... [Y]

If you answered YES to either of the above, then *how often* do you usually think about those things:
           *NOT AT ALL* [0] [1] [2] [3] [4] [5] [6] [7] [8] *A GREAT DEAL*

When you think about these things, *how strongly* do you feel the following emotions:

ANNOYED or DISAPPOINTED
     with Yourself ............. [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL* ... [0] [1] [2] [3] [4] [5] [6] [7] [8]

<page 3> continued on back

7. Which of the following things do you think about:
   (a) NOT having enough FREEDOM or INDEPENDENCE TO DO
       WHAT YOU WANT TO DO? ................................................ [Y]
   (b) NOT being able to DO CERTAIN THINGS ON YOUR OWN or BY YOURSELF? .. [Y]
   (c) being FORCED or PRESSURED into doing things YOU DON'T WANT TO DO? .. [Y]

If you answered YES to either of the above, then *how often* do you usually think about those things:
               *NOT AT ALL* [0] [1] [2] [3] [4] [5] [6] [7] [8] *A GREAT DEAL*

When you think about this, *how strongly* do you feel the following emotions:

ANNOYED or DISAPPOINTED
     with Yourself .............. [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL* ... [0] [1] [2] [3] [4] [5] [6] [7] [8]

8. Which of the following things do you think about:
   (a) you NOT taking good enough CARE of CERTAIN PEOPLE? ..................... [Y]
   (b) you PHYSICALLY HURTING CERTAIN PEOPLE? ........................... [Y]
   (c) you EMOTIONALLY HURTING CERTAIN PEOPLE? ........................ [Y]

If you answered YES to the above, then *how often* do you usually think about it:
               *NOT AT ALL* [0] [1] [2] [3] [4] [5] [6] [7] [8] *A GREAT DEAL*

When you think about this, *how strongly* do you feel the following emotions:

ANNOYED or DISAPPOINTED
     with Yourself .............. [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL* ... [0] [1] [2] [3] [4] [5] [6] [7] [8]

*< page 4 >  continued on next page*

9. Which of the following things do you think about:
   (a) NOT having enough FUN or EXCITEMENT? .................................... [Y]
   (b) NOT having enough INTERESTING THINGS TO DO? ......................... [Y]
   (c) being BORED? ........................................................... [Y]
   (d) NOT having enough RELAXATION, COMFORT, or PEACE OF MIND? ......... [Y]
   (e) being OVER-WORKED or OVER-STRESSED? ................................. [Y]
   (f) how you DON'T KNOW WHAT YOU WANT TO DO WITH YOUR LIFE? ....... [Y]
   (g) how your LIFE is EMPTY, MEANINGLESS, or WITHOUT PURPOSE? .......... [Y]

If you answered YES to any of the above, then *how often* do you usually think about those things:
           *NOT AT ALL* [0] [1] [2] [3] [4] [5] [6] [7] [8] *A GREAT DEAL*

When you think about these things, *how strongly* do you feel the following emotions:

ANNOYED or DISAPPOINTED
     with Yourself ............ [0] [1] [2] [3] [4] [5] [6] [7] [8]
   • *ANGRY at Yourself* ........ [0] [1] [2] [3] [4] [5] [6] [7] [8]
   • *ASHAMED/EMBARRASSED* [0] [1] [2] [3] [4] [5] [6] [7] [8]
   • *GUILTY or REMORSEFUL* . [0] [1] [2] [3] [4] [5] [6] [7] [8]

ANNOYED or DISAPPOINTED
     with Other People or ...... [0] [1] [2] [3] [4] [5] [6] [7] [8]
     the Circumstances
   • *ANGRY* ................. [0] [1] [2] [3] [4] [5] [6] [7] [8]

SAD or UNHAPPY ......... [0] [1] [2] [3] [4] [5] [6] [7] [8]
   • *DEPRESSED* ............. [0] [1] [2] [3] [4] [5] [6] [7] [8]

CONCERNED or UNEASY ... [0] [1] [2] [3] [4] [5] [6] [7] [8]
   • *ANXIOUS or FEARFUL* ... [0] [1] [2] [3] [4] [5] [6] [7] [8]

10. Which of the following things do you think about:
    (a) the THINGS YOU HAVE DONE WRONG? .................................... [Y]
    (b) the THINGS YOU MAY DO WRONG in the FUTURE? ........................ [Y]

If you answered YES to the above, then *how often* do you usually think about it:
            *NOT AT ALL* [0] [1] [2] [3] [4] [5] [6] [7] [8] *A GREAT DEAL*

When you think about this, *how strongly* do you feel the following emotions:

ANNOYED or DISAPPOINTED
      with Yourself ............ [0] [1] [2] [3] [4] [5] [6] [7] [8]
    • *ANGRY at Yourself* ........ [0] [1] [2] [3] [4] [5] [6] [7] [8]
    • *ASHAMED/EMBARRASSED* [0] [1] [2] [3] [4] [5] [6] [7] [8]
    • *GUILTY or REMORSEFUL* . [0] [1] [2] [3] [4] [5] [6] [7] [8]

ANNOYED or DISAPPOINTED
      with Other People or ...... [0] [1] [2] [3] [4] [5] [6] [7] [8]
      the Circumstances
    • *ANGRY* ................. [0] [1] [2] [3] [4] [5] [6] [7] [8]

SAD or UNHAPPY ......... [0] [1] [2] [3] [4] [5] [6] [7] [8]
    • *DEPRESSED* ............. [0] [1] [2] [3] [4] [5] [6] [7] [8]

CONCERNED or UNEASY ... [0] [1] [2] [3] [4] [5] [6] [7] [8]
    • *ANXIOUS or FEARFUL* ... [0] [1] [2] [3] [4] [5] [6] [7] [8]

< page 5 > continued on back

11. Which of the following things do you think about:
    (a) the THINGS OTHER PEOPLE HAVE DONE WRONG? ...................... [Y]
    (b) the THINGS OTHERS MAY DO WRONG in the FUTURE? ................... [Y]

If you answered YES to the above, then *how often* do you usually think about it:
          NOT AT ALL [0] [1] [2] [3] [4] [5] [6] [7] [8] *A GREAT DEAL*

When you think about this, *how strongly* do you feel the following emotions:

ANNOYED or DISAPPOINTED
      with Yourself ............ [0] [1] [2] [3] [4] [5] [6] [7] [8]
    • *ANGRY at Yourself* ....... [0] [1] [2] [3] [4] [5] [6] [7] [8]
    • *ASHAMED/EMBARRASSED* [0] [1] [2] [3] [4] [5] [6] [7] [8]
    • *GUILTY or REMORSEFUL* . [0] [1] [2] [3] [4] [5] [6] [7] [8]

ANNOYED or DISAPPOINTED
      with Other People or ...... [0] [1] [2] [3] [4] [5] [6] [7] [8]
      the Circumstances
    • *ANGRY* ................. [0] [1] [2] [3] [4] [5] [6] [7] [8]

SAD or UNHAPPY ......... [0] [1] [2] [3] [4] [5] [6] [7] [8]
    • *DEPRESSED* ............. [0] [1] [2] [3] [4] [5] [6] [7] [8]

CONCERNED or UNEASY ... [0] [1] [2] [3] [4] [5] [6] [7] [8]
    • *ANXIOUS or FEARFUL* ... [0] [1] [2] [3] [4] [5] [6] [7] [8]

12. Do you think about:
      how YOU are NOT a GOOD ENOUGH PERSON? .............................. [Y]

If you answered YES to the above, then *how often* do you usually think about those things
          NOT AT ALL ... [0] [1] [2] [3] [4] [5] [6] [7] [8] *A GREAT DEAL*

13. Do you think about:
      how OTHERS are NOT GOOD ENOUGH PEOPLE? ............................ [Y]

If you answered YES to the above, then *how often* do you usually think about those things:
          NOT AT ALL [0] [1] [2] [3] [4] [5] [6] [7] [8] *A GREAT DEAL*

14. Do you think about:
      how YOU are NOT a VALUABLE, WORTHY or IMPORTANT ENOUGH PERSON .. [Y]

If you answered YES to the above, then *how often* do you usually think about those things:
          NOT AT ALL [0] [1] [2] [3] [4] [5] [6] [7] [8] *A GREAT DEAL*

15. Do you think about:
      how OTHERS are NOT VALUABLE, WORTHY or IMPORTANT ENOUGH PEOPLE [Y]

If you answered YES to the above, then *how often* do you usually think about those things:
          NOT AT ALL [0] [1] [2] [3] [4] [5] [6] [7] [8] *A GREAT DEAL*

---

Note: If the patient/client appears *unable or unwilling to adequately or honestly answer the items in this questionnaire*, please indicate the probable reason(s) below:
[ ] Cannot understand the items due to low intellect (mental retardation).
[ ] Cannot adequately respond to the items due to a formal thought disorder (psychotic thought processes - *see the Mental-Behavioral Status Questionnaire*).
[ ] Cannot adequately respond to the items due to inability to identify or quantify his/her emotions.
[ ] Refuses to respond adequately or honestly to the items due to suspiciousness, distrust, or defensiveness.

*END*

*No. 1*

When I think about:
- □ having serious PHYSICAL HURT,
- □ having serious PHYSICAL HANDICAPS,
- □ having serious LEANING DISABILITIES,
- □ having serious ILLNESS or DISEASE,
- □ having serious EMOTIONAL or MENTAL ILLNESS,
- □ DYING in the near future I often feel:

B01- [Y] [N]   HELPLESS - NOT IN CONTROL ... like there's NOTHING I CAN DO ABOUT IT.

I believe that:

B02- [Y] [N]   There are times that I SHOULD NOT (MUST NOT, OUGHT NOT) be [ ... ]

B03- [Y] [N]   I sometimes NEED TO (or HAVE TO) feel well - learn easily - or stop thinking about dying.

B04- [Y] [N]   It's sometimes AWFUL (TERRIBLE) to be [ ... ]

B05- [Y] [N]   It's a problem that I sometimes CAN'T STAND (CAN'T TOLERATE).

B06- [Y] [N]   It's a problem that will probably ALWAYS have; it will probably NEVER end.

B07- [Y] [N]   It's WRONG and UNFAIR for this to happen to me ... I'm just a VICTIM.

B08- [Y] [N]   I DESERVE better than this.

Having {or thinking about being} [ ... ] makes me feel:

B09- [Y] [N]   INSECURE, SELF-DOUBTING, SELF-CONSCIOUS, or INADEQUATE

B10- [Y] [N]   DEGRADED, BELITTLED, PUT-DOWN, HUMILIATED, or DISGRACED

B11- [Y] [N]   like I'm NO GOOD or I'm LESS OF A PERSON

B12- [Y] [N]   like someone else is NO GOOD or is LESS OF A PERSON

B13- [Y] [N]   like it's PUNISHMENT for things I have done wrong ... punishment that I DESERVE.

B14- [Y] [N]   I ENVY certain people who feel better and are healthier than I am.

B15- [Y] [N]   I sometimes RESENT IT when they feel better and are healthier than I am.

Notes:

< Phase II - supplement B to ITEM # 1 >

Appendix B

**\*No. 2\***

When I think about:
- ☐ getting REJECTED¹,
- ☐ getting RIDICULED¹,
- ☐ NOT HAVING ENOUGH LOVE²
- ☐ NOT HAVING ENOUGH AFFECTION OR SEX²
- ☐ NOT HAVING ENOUGH ACCEPTANCE²
- ☐ NOT HAVING ENOUGH APPROVAL²
- ☐ NOT HAVING ENOUGH RECOGNITION²

I often feel:

B01- [Y] [N]   HELPLESS - NOT IN CONTROL ... like there's NOTHING I CAN DO ABOUT IT.

I believe that:

B02- [Y] [N]   There are times that I SHOULD NOT (MUST NOT, OUGHT NOT) get [ ... ]¹ or I SHOULD (MUST, OUGHT TO) have more [ ... ]²

B03- [Y] [N]   I sometimes NEED TO (or HAVE TO) to have less [ ... ]¹ or more [ ... ]²

B04- [Y] [N]   It's sometimes AWFUL (TERRIBLE) to get[ ... ]¹ or not have more[ ... ]²

B05- [Y] [N]   It's a problem that I sometimes CAN'T STAND (CAN'T TOLERATE).

B06- [Y] [N]   It's a problem that will probably ALWAYS have; it will probably NEVER end.

B07- [Y] [N]   It's WRONG and UNFAIR for this to happen to me ... I'm just a VICTIM.

B08- [Y] [N]   I DESERVE better than this.

Getting [ ... ]¹ or not having enough [ ... ]²

B09- [Y] [N]   INSECURE, SELF-DOUBTING, SELF-CONSCIOUS, or INADEQUATE

B10- [Y] [N]   DEGRADED, BELITTLED, PUT-DOWN, HUMILIATED, or DISGRACED

B11- [Y] [N]   like I'm NO GOOD or I'm LESS OF A PERSON

B12- [Y] [N]   like someone else is NO GOOD or is LESS OF A PERSON

B13- [Y] [N]   like it's PUNISHMENT for things I have done wrong ... punishment that I DESERVE.

B14- [Y] [N]   I ENVY certain people who are more popular or well-liked than I am.

B15- [Y] [N]   I sometimes RESENT IT when I get rejected or ridiculed instead of them.

B16- [Y] [N]   I often get JEALOUS thinking about a special person giving their love to someone other than me.

Notes:

< Phase II - supplement B to ITEM # 2->

*No. 3*

When I think about NOT HAVING or KEEPING ENOUGH MONEY or POSSESSIONS, I often feel:

B01- [Y] [N]   HELPLESS - NOT IN CONTROL ... like there's NOTHING I CAN DO ABOUT IT.

I believe that:

B02- [Y] [N]   There are times that I SHOULD (MUST, OUGHT TO) have more money or possessions.
B03- [Y] [N]   I sometimes NEED TO (or HAVE TO) have more money or possessions.
B04- [Y] [N]   It's sometimes AWFUL (TERRIBLE) not to have enough money or possessions.
B05- [Y] [N]   It's a problem that I sometimes CAN'T STAND (CAN'T TOLERATE).
B06- [Y] [N]   It's a problem that will probably ALWAYS have; it will probably NEVER have enough money or possessions..
B07- [Y] [N]   It's WRONG and UNFAIR for this to happen to me ... I'm just a VICTIM.
B08- [Y] [N]   I DESERVE better than this.

Not having or keeping enough MONEY or POSSESSIONS makes me feel:

B09- [Y] [N]   INSECURE, SELF-DOUBTING, SELF-CONSCIOUS, or INADEQUATE
B10- [Y] [N]   DEGRADED, BELITTLED, PUT-DOWN, HUMILIATED, or DISGRACED
B11- [Y] [N]   like I'm NO GOOD or I'm LESS OF A PERSON
B12- [Y] [N]   like someone else is NO GOOD or is LESS OF A PERSON
B13- [Y] [N]   like it's PUNISHMENT for things I have done wrong ... punishment that I DESERVE.

B14- [Y] [N]   I ENVY certain people who have more money or possessions than I do.
B15- [Y] [N]   I sometimes RESENT IT when they have more than me.
B16- [Y] [N]   I sometimes feel: JEALOUS thinking about a special person who considers money to be more important than he/she considers me.

Notes:

< Phase II - supplement B to ITEM # 3 >

* No. 4 *

When I think about CERTAIN PEOPLE BEING:
☐ SERIOUSLY HURT or ILL,
☐ EMOTIONALLY ILL or UPSET-or DYING,
I often feel:

B01- [Y] [N]    HELPLESS - NOT IN CONTROL ... like there's NOTHING I CAN DO ABOUT IT.

I believe that:

B02- [Y] [N]    Certain people I know SHOULD NOT (MUST NOT, OUGHT NOT) be [ ... ]

B03- [Y] [N]    They sometimes NEED TO (or HAVE TO) be well and feel all right., and be alive B04- [Y] [N]    It's sometimes AWFUL (TERRIBLE) when certain people are [ ... ]

B05- [Y] [N]    It's a problem that I sometimes CAN'T STAND (CAN'T TOLERATE).

B06- [Y] [N]    It's a problem that will probably ALWAYS have; it will probably NEVER end.

B07- [Y] [N]    It's WRONG and UNFAIR for this to happen to me...they're just VICTIMS.

B08- [Y] [N]    They DESERVE better than this.

When CERTAIN PEOPLE ARE [ ... ], I tend to feel

B09- [Y] [N]    INSECURE, SELF-DOUBTING, SELF-CONSCIOUS, or INADEQUATE

B10- [Y] [N]    DEGRADED, BELITTLED, PUT-DOWN, HUMILIATED, or DISGRACED

B11- [Y] [N]    like I'm NO GOOD or I'm LESS OF A PERSON

B12- [Y] [N]    like someone else is NO GOOD or is LESS OF A PERSON

B13- [Y] [N]    like it's PUNISHMENT for things I have done wrong ... punishment that I DESERVE.

B14- [Y] [N]    I ENVY people who feel better than [-?-] do/does.

B15- [Y] [N]    I sometimes RESENT people who are healthier and happier than they are.

Notes:

< Phase II - supplement B to ITEM # 4 >

*No. 5*

When I think about how certain people DON'T:
☐ CARE ABOUT WHAT I SAY,
☐ CARE ABOUT WHAT I WANT,
☐ RESPECT ME,
☐ UNDERSTAND or CARE HOW I FEEL,
I often feel:

B01- [Y] [N]    HELPLESS - NOT IN CONTROL ... like there's NOTHING I CAN DO ABOUT IT.

I believe that:

B02- [Y] [N]    There are times that I SHOULD (MUST, OUGHT TO) [ ... ]

B03- [Y] [N]    I sometimes NEED TO (or HAVE TO) have more respect and understanding from others.

B04- [Y] [N]    It's sometimes AWFUL (TERRIBLE) when certain people don't [ ... ]

B05- [Y] [N]    It's a problem that I sometimes CAN'T STAND (CAN'T TOLERATE).

B06- [Y] [N]    It's a problem that will probably ALWAYS have; it will probably NEVER have enough respect and understanding from others.

B07- [Y] [N]    It's WRONG and UNFAIR for this to happen to me ... I'm just a VICTIM.

B08- [Y] [N]    I DESERVE better than this.

When certain people don't [ ... ], I often feel:

B09- [Y] [N]    INSECURE, SELF-DOUBTING, SELF-CONSCIOUS, or INADEQUATE

B10- [Y] [N]    DEGRADED, BELITTLED, PUT-DOWN, HUMILIATED, or DISGRACED

B11- [Y] [N]    like I'm NO GOOD or I'm LESS OF A PERSON

B12- [Y] [N]    like someone else is NO GOOD or is LESS OF A PERSON

B13- [Y] [N]    like it's PUNISHMENT for things I have done wrong ... punishment that I DESERVE.

B14- [Y] [N]    I ENVY certain people who are more respected, important or influential than I am.

B15- [Y] [N]    I sometimes RESENT IT when people care more about what certain others than what I want or say.

B16- [Y] [N]    I sometimes feel: JEALOUS thinking about how a special person cares more about what other people want or say than about what I want or say.

Notes:

*< Phase II - supplement B to ITEM # 5 >*

*No. 6*

When I think about NOT BEING ABLE TO:
☐ DEPEND ON certain people,
☐ TRUST certain people,
I often feel:

B01- [Y] [N]   HELPLESS - NOT IN CONTROL ... like there's NOTHING I CAN DO ABOUT IT.

I believe that:

B02- [Y] [N]   There are times that I SHOULD (MUST, OUGHT TO) be able to [ ... ].

B03- [Y] [N]   I sometimes NEED TO (or HAVE TO) be able to [ ... ].

B04- [Y] [N]   It's sometimes AWFUL (TERRIBLE) when certain people are not dependable - trustworthy.

B05- [Y] [N]   It's a problem that I sometimes CAN'T STAND (CAN'T TOLERATE).

B06- [Y] [N]   It's a problem that I will probably ALWAYS have; certain will probably NEVER be more dependable - trustworthy.

B07- [Y] [N]   It's WRONG and UNFAIR for this to happen to me ... I'm just a VICTIM.

B08- [Y] [N]   I DESERVE better than this.

When I am not able to [ ... ], I often feel:

B09- [Y] [N]   INSECURE, SELF-DOUBTING, SELF-CONSCIOUS, or INADEQUATE

B10- [Y] [N]   DEGRADED, BELITTLED, PUT-DOWN, HUMILIATED, or DISGRACED

B11- [Y] [N]   like I'm NO GOOD or I'm LESS OF A PERSON

B12- [Y] [N]   like someone else is NO GOOD or is LESS OF A PERSON

B13- [Y] [N]   like it's PUNISHMENT for things I have done wrong ... punishment that I DESERVE.

B14- [Y] [N]   I ENVY certain individuals who have more people they can depend upon or trust than I do.

B15- [Y] [N]   I sometimes RESENT IT when they can depend on or trust others while I can't.

B16- [Y] [N]   I sometimes feel: JEALOUS thinking about how a special person is dependable or trustworthy to others, but not to me.

Notes:

*< Phase II - supplement B to ITEM # 6 >*

*No. 7*

When I think about When I think about:
- ☐ NOT HAVING ENOUGH [FREEDOM or INDEPENDENCE TO DO WHAT I WANT TO DO]$^1$,
- ☐ NOT BEING ABLE TO [DO CERTAIN THINGS ON MY OWN or BY MYSELF]$^2$,
- ☐ BEING [FORCED or PRESSURED INTO DOING THINGS I DON'T WANT TO DO]$^3$, I often feel:

B01- [Y] [N]  HELPLESS - NOT IN CONTROL ... like there's NOTHING I CAN DO ABOUT IT.

I believe that:

B02- [Y] [N]  There are times that I SHOULD (MUST, OUGHT TO) have more [ ... ]$^1$ - be able to [ ... ]$^2$ - or I SHOULD NOT (MUST NOT, OUGHT NOT) be [ ... ]$^3$ B03- [Y] [N]  I sometimes NEED TO (or HAVE TO) have more [ ... ]$^1$ - be able to [ ... ]$^2$ - or not be [ ... ]$^3$ B04- [Y] [N]  It's sometimes AWFUL (TERRIBLE) not to have more [ ... ]$^1$ - be able to [ ... ]$^2$ - or not be [ ... ]$^3$ B05- [Y] [N]  It's a problem that I sometimes CAN'T STAND (CAN'T TOLERATE).

B06- [Y] [N]  It's a problem that will probably ALWAYS have; it will probably NEVER have enough [ ... ]$^1$ - not be able to [ ... ]$^2$ - or people won't stop [ ... ]$^3$ B07- [Y] [N]  It's WRONG and UNFAIR for this to happen to me ... I'm just a VICTIM.

B08- [Y] [N]  I DESERVE better than this.

Not having enough [ ... ]$^1$ - not being able to [ ... ]$^2$ - or being [ ... ]$^3$ B09- [Y] [N]  INSECURE, SELF-DOUBTING, SELF-CONSCIOUS, or INADEQUATE B10- [Y] [N]  DEGRADED, BELITTLED, PUT-DOWN, HUMILIATED, or DISGRACED B11- [Y] [N]  like I'm NO GOOD or I'm LESS OF A PERSON B12- [Y] [N]  like someone else is NO GOOD or is LESS OF A PERSON B13- [Y] [N]  like it's PUNISHMENT for things I have done wrong ... punishment that I DESERVE.

B14- [Y] [N]  I ENVY certain people who have more freedom and independence - autonomy than I do.

B15- [Y] [N]  I sometimes RESENT IT when they have more freedom and independence - autonomy than I do.

B16- [Y] [N]  I sometimes feel: JEALOUS thinking about a special person who considers money to be more important than he/she considers me.

Notes:

< Phase II - supplement B to ITEM # 7 >

* No. 8 *

When I think about me:
☐ NOT [TAKING GOOD ENOUGH CARE of certain people][1],
☐ PHYSICALLY HURTING certain people[2],
☐ EMOTIONALLY HURTING certain people[2],
I often feel:

B01- [Y] [N]   HELPLESS - NOT IN CONTROL ... like there's NOTHING I CAN DO ABOUT IT.

I believe that:

B02- [Y] [N]   There are times that I SHOULD (MUST, OUGHT TO) be [ ... ][1] - I SHOULD NOT (MUST NOT, OUGHT NOT) be [ ... ][2].

B03- [Y] [N]   I sometimes NEED TO (or HAVE TO) take better care of certain people.

B04- [Y] [N]   It's sometimes AWFUL (TERRIBLE) when I'm not [ ... ][1] or when I am [ ... ][2].

B05- [Y] [N]   It's a problem that I sometimes CAN'T STAND (CAN'T TOLERATE).

B06- [Y] [N]   It's a problem that will probably ALWAYS have; it will probably NEVER take good enough care of certain people.

B07- [Y] [N]   It's WRONG and UNFAIR for this to happen to me ... I'm just a VICTIM.

B08- [Y] [N]   I DESERVE better than this.

When I am [ ... ][1&2] I often feel:

B09- [Y] [N]   INSECURE, SELF-DOUBTING, SELF-CONSCIOUS, or INADEQUATE

B10- [Y] [N]   DEGRADED, BELITTLED, PUT-DOWN, HUMILIATED, or DISGRACED

B11- [Y] [N]   like I'm NO GOOD or I'm LESS OF A PERSON

B12- [Y] [N]   like someone else is NO GOOD or is LESS OF A PERSON

B13- [Y] [N]   like it's PUNISHMENT for things I have done wrong ... punishment that I DESERVE.

B14- [Y] [N]   I ENVY certain people who take better care of others than I do.

B15- [Y] [N]   I sometimes RESENT IT when they take better care of others than I do.

Notes:

< Phase II - supplement B to ITEM # 8 >

*No. 9 *

When I think about:
- ☐ NOT [HAVING ENOUGH FUN or EXCITEMENT]$^1$,
- ☐ NOT [HAVING ENOUGH INTERESTING THINGS TO DO]$^1$,
- ☐ being [BORED]$^2$,
- ☐ NOT [HAVING ENOUGH RELAXATION. COMFORT, or PEACE OF MIND]$^1$,
- ☐ being [OVER-WORKED or OVER-STRESSED]$^2$,
- ☐ NOT [KNOWING WHAT I WANT TO DO WITH MY LIFE]$^1$,
- ☐ HAVING A LIFE THAT IS EMPTY, MEANINGLESS, or WITHOUT PURPOSE$^2$, I often feel:

B01- [Y] [N]   HELPLESS - NOT IN CONTROL ... like there's NOTHING I CAN DO ABOUT IT.

I believe that:

B02- [Y] [N]   There are times that I SHOULD (MUST, OUGHT TO) be [ ... ]$^1$ or I SHOULD NOT (MUST NOT , OUGHT NOT) be [ ... ]$^2$ B03- [Y] [N]   I sometimes NEED TO (or HAVE TO) have more fun - excitement - interests - relaxation - direction - meaning in my life.

B04- [Y] [N]   It's sometimes AWFUL (TERRIBLE) not to be [ ... ]$^1$ or to be [ ... ]$^2$ B05- [Y] [N]   It's a problem that I sometimes CAN'T STAND (CAN'T TOLERATE).

B06- [Y] [N]   It's a problem that will probably ALWAYS have; it will probably NEVER have enough fun - excitement - interests - relaxation - direction - meaning in my life.

B07- [Y] [N]   It's WRONG and UNFAIR for this to happen to me ... I'm just a VICTIM.

B08- [Y] [N]   I DESERVE better than this.

Not having [ ... ]$^1$ or having [ ... ]$^2$, makes me feel:

B09- [Y] [N]   INSECURE, SELF-DOUBTING, SELF-CONSCIOUS, or INADEQUATE

B10- [Y] [N]   DEGRADED, BELITTLED, PUT-DOWN, HUMILIATED, or DISGRACED

B11- [Y] [N]   like I'm NO GOOD or I'm LESS OF A PERSON

B12- [Y] [N]   like someone else is NO GOOD or is LESS OF A PERSON

B13- [Y] [N]   like it's PUNISHMENT for things I have done wrong ... punishment that I DESERVE.

B14- [Y] [N]   I ENVY certain people who have more [ ... ]$^1$ than I do or don't have [ ... ]$^2$ like I do.

B15- [Y] [N]   I sometimes RESENT IT when this happens.

B16- [Y] [N]   I'm sometimes JEALOUS thinking about a special person would rather have fun with people other than me.

Notes:

< Phase II - supplement B to ITEM # 9 >

*No. 10*

When I think about the THINGS I HAVE DONE or MAY DO WRONG, I often feel:

B01- [Y] [N]    HELPLESS - NOT IN CONTROL ... like there's NOTHING I CAN DO ABOUT IT.

I believe that:

B02- [Y] [N]    There are times that I SHOULD NOT (MUST NOT, OUGHT NOT) do certain things wrong.
B03- [Y] [N]    I sometimes NEED TO (or HAVE TO) do certain things right.
B04- [Y] [N]    It's sometimes AWFUL (TERRIBLE) to do certain things wrong.
B05- [Y] [N]    It's a problem that I sometimes CAN'T STAND (CAN'T TOLERATE).
B06- [Y] [N]    It's a problem that will probably ALWAYS have; it will probably NEVER do certain things right.
B07- [Y] [N]    It's WRONG and UNFAIR for this to happen to me ... I'm just a VICTIM.
B08- [Y] [N]    I DESERVE better than this.

When I think about the THINGS I HAVE DONE or MAY DO WRONG, I often feel:

B09- [Y] [N]    INSECURE, SELF-DOUBTING, SELF-CONSCIOUS, or INADEQUATE
B10- [Y] [N]    DEGRADED, BELITTLED, PUT-DOWN, HUMILIATED, or DISGRACED
B11- [Y] [N]    like I'm NO GOOD or I'm LESS OF A PERSON
B12- [Y] [N]    like someone else is NO GOOD or is LESS OF A PERSON
B13- [Y] [N]    like it's PUNISHMENT for things I have done wrong ... punishment that I DESERVE.

E1- [Y] [N]    I ENVY certain people who have NOT done the things I have done wrong ... punishment that I DESERVE.
E2- [Y] [N]    I sometimes RESENT IT when they are not wrong, but I am wrong.

Notes:

< Phase II - supplement B to ITEM # 10 >

*No. 11*

When I think about the THINGS OTHERS HAVE DONE or MAY DO WRONG, I often feel:

B01- [Y] [N]   HELPLESS - NOT IN CONTROL ... like there's NOTHING I CAN DO ABOUT IT.

I believe that:

B02- [Y] [N]   There are times that OTHERS SHOULD NOT (MUST NOT, OUGHT NOT) do certain things wrong.
B03- [Y] [N]   They sometimes NEED TO (or HAVE TO) do certain things right.
B04- [Y] [N]   It's sometimes AWFUL (TERRIBLE) when they do certain things wrong.
B05- [Y] [N]   It's a problem that I sometimes CAN'T STAND (CAN'T TOLERATE).
B06- [Y] [N]   It's a problem that will probably ALWAYS have; they will probably NEVER do certain things right.
B07- [Y] [N]   It's WRONG and UNFAIR for this to happen to me ... I'm just a VICTIM.
B08- [Y] [N]   I DESERVE better than this.

When I think about the THINGS OTHERS HAVE DONE or MAY DO WRONG, I often feel:

B09- [Y] [N]   INSECURE, SELF-DOUBTING, SELF-CONSCIOUS, or INADEQUATE
B10- [Y] [N]   DEGRADED, BELITTLED, PUT-DOWN, HUMILIATED, or DISGRACED
B11- [Y] [N]   like I am NO GOOD or LESS OF A PERSON
B12- [Y] [N]   like someone else is NO GOOD or is LESS OF A PERSON
B13- [Y] [N]   like it's PUNISHMENT for things I have done wrong ... punishment that I DESERVE.

Notes:

< Phase II - supplement B to ITEM # 11 >

*Please answer the following using the scale below:*

| [ Y ] = Usually or Mostly YES    [ N ] = Usually or Mostly NO |
|---|

C1> [Y] [N]  Are you ever confused about WHO you REALLY ARE?

Explain:_____

_____

How do you judge or describe yourself ... what KIND of person are you?

_____
_____
_____
_____

Are you:

C2> [Y] [N] a DISAPPOINTMENT to your PARENTS?  [If so, explain:_____
_____]

C3> [Y] [N] a DISAPPOINTMENT to YOURSELF?  [If so, explain:_____
_____]

C4> [Y] [N] a DISAPPOINTMENT to OTHER PEOPLE?  [If so, explain:_____
_____]

Are you:

C5> [Y] [N]  the kind of person that you OUGHT TO BE?   [Explain:_____
_____]

C6> [Y] [N]  the kind of person that you WANT TO BE?    [Explain:_____
_____]

C7> [Y] [N]  the kind of person that you are EXPECTED TO BE? [Explain:_____
_____]

Notes:

*< Phase II - supplement B >*

THOUGHTS / EMOTIONS ANALYSIS SHEET

PHASE - TWO

* PEOPLE-APPRAISALS *

* No. 12 *
Thinking about how you are NOT A GOOD ENOUGH PERSON

> You believe that you are NOT a GOOD ENOUGH PERSON

What makes you that way?: _____

[Y] [N]   Was there ever a when you got upset thinking about how you were bad, wicked, evil or rotten?

If so, when/why? _____

* No. 14 *
Thinking about how you are NOT a VALUABLE, WORTHY or IMPORTANT ENOUGH PERSON > You believe that you are NOT a VALUABLE, WORTHY or IMPORTANT ENOUGH PERSON What makes you that way?: _____

[Y] [N]   Was there ever a when you got upset thinking about how you were worthless, useless, inferior, a failure?

If so, when/why? _____

* No. 13 *
Thinking about how others are NOT GOOD ENOUGH PEOPLE

> You believe that others are NOT GOOD ENOUGH PEOPLE

> Who are they: _____

What makes you that way?: _____

[Y] [N]   Was there ever a that you got upset while thinking about how bad, wicked, evil, rotten certain people are?

If so, when/why? _____

* No. 15 *
Thinking about how others are NOT a VALUABLE, WORTHY or IMPORTANT ENOUGH PEOPLE > You believe that others are NOT a VALUABLE, WORTHY or IMPORTANT ENOUGH PEOPLE > Who are they: _____

What makes you that way?: _____

[Y] [N]   Was there ever a that you got upset while thinking about how bad, wicked, evil, rotten certain people are?

If so, when/why? _____

* No. 1 *   1. How often do you think about BEING PHYSICALLY HURT, ILL, or HAVING A DISEASE, or DYING?

Frequency of thoughts about:
being PHYSICALLY PAINED, HURT, or INJURED

Appendix B continued havinga PHYSICAL HANDICAP
having a LEARNING DISABILITY
having a SERIOUS ILLNESS or DISEASE
having a SERIOUS EMOTIONAL or MENTAL ILLNESS
(thoughts about your) DEATH S=Self | O=Others (Both may be checked off)
A1a - [Y] [N]     Have you ever been bothered by (any of) the above?
A1b - [S] [O]     > If YES, who was RESPONSIBLE for making it happen? -- Explain>_____

A1c - [S] [O]     > Did you/he/she/they do something UNFORGIVABLE? -- Explain>_____

A2a - [Y] [N]     Will you probably be bothered by the (any of) above in the near future?
A2b - [S] [O]     > If YES, who will probably be RESPONSIBLE for making it happen? -- Explain>_____

A2c - [S] [O]     > Will you/he/she/they probably do something UNFORGIVABLE? -- Explain>_____

What has to happen for you not to feel (that you will be) bothered by physical hurt, illness, disease or handicaps?
_____
_____
_____

When you think about the above, you feel:

ANNOYED/DISAPPOINTED with Yourself
- ANGRY at Yourself
- ASHAMED/EMBARRASSED
- GUILTY
Why do you feel this way? _____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL
Why do you feel this way? _____

* No. 2 *

Frequency of thoughts about:

being REJECTED
being RIDICULED
NOT having enough LOVE
NOT having enough AFFECTION or SEX
NOT being ACCEPTED by certain people
NOT having the APPROVAL of certain people
NOT having the RECOGNITION of certain people S=Self | O=Others (Both may be checked off)
A1a - [Y] [N]     Have you ever been bothered by (any of) the above?
A1b - [S] [O]     > If YES, who was RESPONSIBLE for making it happen? -- Explain>_____

A1c - [S] [O]     > Did you/he/she/they do something UNFORGIVABLE? -- Explain>_____

A2a - [Y] [N]     Will you probably be bothered by the (any of) above in the near future?
A2b - [S] [O]     > If YES, who will probably be RESPONSIBLE for making it happen? -- Explain>_____

A2c - [S] [O]  > Will you/he/she/they probably do something UNFORGIVABLE? -- Explain>_____

What has to happen for you NOT TO BE BOTHERED about the above?
_____
_____
_____

When you think about the above, you feel:

ANNOYED/DISAPPOINTED with Yourself
- ANGRY at Yourself
- ASHAMED/EMBARRASSED
- GUILTY
Why do you feel this way? _____
_____

ANNOYED/DISAPPOINTED with Other People or Circumstances
- ANGRY at Others
Why do you feel this way? _____
_____

SAD or UNHAPPY
- DEPRESSED
Why do you feel this way? _____
_____

CONCERNED or UNEASY
- ANXIOUS/FEARFUL
Why do you feel this way? _____
_____

\* No. 3 \*

Frequency of thoughts about not having (or KEEPING) ENOUGH MONEY or POSSESSIONS

S=Self | O=Others (Both may be checked off)

A1a - [Y] [N]   Have you ever been bothered by (any of) the above?
A1b - [S] [O]   > If YES, who was RESPONSIBLE for making it happen? -- Explain>_____

A1c - [S] [O]   > Did you/he/she/they do something UNFORGIVABLE? -- Explain>_____

A2a - [Y] [N]   Will you probably be bothered by the (any of) above in the near future?
A2b - [S] [O]   > If YES, who will probably be RESPONSIBLE for making it happen? -- Explain>_____

A2c - [S] [O]   > Will you/he/she/they probably do something UNFORGIVABLE? -- Explain>_____

What has to happen for you NOT TO BE BOTHERED about the above?
_____
_____
_____

When you think about the above, you feel:

ANNOYED/DISAPPOINTED with Yourself
- ANGRY at Yourself
- ASHAMED/EMBARRASSED
- GUILTY
Why do you feel this way? _____
_____

ANNOYED/DISAPPOINTED with Other People or Circumstances
- ANGRY at Others
Why do you feel this way? _____
_____

SAD or UNHAPPY
- DEPRESSED
Why do you feel this way? _____

CONCERNED or UNEASY
- ANXIOUS/FEARFUL
Why do you feel this way? _____

* No. 4 *

Frequency of thoughts about:

OTHER PEOPLE BEING PHYSICALLY HURT or ILL
OTHER PEOPLE BEING EMOTIONALLY ILL or UPSET
OTHER PEOPLE DYING

S=Self | O=Others (Both may be checked off)
A1a - [Y] [N]   Have you ever been bothered by (any of) the above?
A1b - [S] [O]   > If YES, who was RESPONSIBLE for making it happen? -- Explain> _____

A1c - [S] [O]   > Did you/he/she/they do something UNFORGIVABLE? -- Explain> _____

A2a - [Y] [N]   Will you probably be bothered by the (any of) above in the near future?
A2b - [S] [O]   > If YES, who will probably be RESPONSIBLE for making it happen? -- Explain> _____

A2c - [S] [O]   > Will you/he/she/they probably do something UNFORGIVABLE? -- Explain> _____

What has to happen for you NOT TO BE BOTHERED about the above?
_____
_____

When you think about the above, you feel:

ANNOYED/DISAPPOINTED with Yourself
- ANGRY at Yourself
- ASHAMED/EMBARRASSED
- GUILTY
Why do you feel this way? _____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL
Why do you feel this way? _____

* No. 5 *

Frequency of thoughts about how:

CERTAIN PEOPLE NOT CARING WHAT YOU SAY
CERTAIN PEOPLE NOT DOING WHAT YOU WANT
CERTAIN PEOPLE NOT RESPECTING YOU
CERTAIN PEOPLE DON'T UNDERSTAND or CARE HOW YOU FEEL

S=Self | O=Others (Both may be checked off)
A1a - [Y] [N]   Have you ever been bothered by (any of) the above?
A1b - [S] [O]   > If YES, who was RESPONSIBLE for making it happen? -- Explain>_____

A1c - [S] [O]   > Did you/he/she/they do something UNFORGIVABLE? -- Explain>_____

A2a - [Y] [N]   Will you probably be bothered by the (any of) above in the near future?
A2b - [S] [O]   > If YES, who will probably be RESPONSIBLE for making it happen? -- Explain>_____

A2c - [S] [O]   > Will you/he/she/they probably do something UNFORGIVABLE? -- Explain>_____

What has to happen for you NOT TO BE BOTHERED about the above?
_____
_____
_____

When you think about the above, you feel:

ANNOYED/DISAPPOINTED with Yourself
- ANGRY at Yourself
- ASHAMED/EMBARRASSED
- GUILTY
Why do you feel this way? _____
_____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL
Why do you feel this way? _____

* No. 6 *

Frequency of thoughts about:

how you CAN'T DEPEND ON CERTAIN PEOPLE
how you CAN'T TRUST CERTAIN PEOPLE

S=Self | O=Others (Both may be checked off)
A1a - [Y] [N]   Have you ever been bothered by (any of) the above?
A1b - [S] [O]   > If YES, who was RESPONSIBLE for making it happen? -- Explain>_____

A1c - [S] [O]   > Did you/he/she/they do something UNFORGIVABLE? -- Explain>_____

A2a - [Y] [N]   Will you probably be bothered by the (any of) above in the near future?
A2b - [S] [O]   > If YES, who will probably be RESPONSIBLE for making it happen? -- Explain>_____

A2c - [S] [O]   > Will you/he/she/they probably do something UNFORGIVABLE? -- Explain>_____

What has to happen for you NOT TO BE BOTHERED about the above?
_____
_____
_____

When you think about the above, you feel:

ANNOYED/DISAPPOINTED with Yourself
- ANGRY at Yourself
- ASHAMED/EMBARRASSED
- GUILTY
Why do you feel this way? _____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL
Why do you feel this way? _____

* No. 7 *

Frequency of thoughts about:

NOT having enough FREEDOM or INDEPENDENCE to do what you want to do
NOT being ABLE TO DO CERTAIN THINGS ON YOUR OWN or BY YOURSELF
being FORCED or PRESSURED into DOING THINGS YOU DON'T WANT TO DO S=Self | O=Others (Both may be checked off)
A1a - [Y] [N]     Have you ever been bothered by (any of) the above?
A1b - [S] [O]     > If YES, who was RESPONSIBLE for making it happen? -- Explain>_____

A1c - [S] [O]     > Did you/he/she/they do something UNFORGIVABLE? -- Explain>_____

A2a - [Y] [N]     Will you probably be bothered by the (any of) above in the near future?
A2b - [S] [O]     > If YES, who will probably be RESPONSIBLE for making it happen? -- Explain>_____

A2c - [S] [O]     > Will you/he/she/they probably do something UNFORGIVABLE? -- Explain>_____

What has to happen for you NOT TO BE BOTHERED about the above? _____

When you think about the above, you feel:

ANNOYED/DISAPPOINTED with Yourself
- ANGRY at Yourself
- ASHAMED/EMBARRASSED
- GUILTY
Why do you feel this way? _____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL

Why do you feel this way? _____

* No. 8 *

Frequency of thoughts about:

YOU NOT TAKING GOOD ENOUGH CARE OF CERTAIN PEOPLE
YOU PHYSICALLY HURTING CERTAIN PEOPLE
YOU EMOTIONALLY HURTING CERTAIN PEOPLE

S=Self | O=Others (Both may be checked off)
A1a - [Y] [N]   Have you ever been bothered because of the above?
A1b - [S] [O]   > If YES, who was RESPONSIBLE for making it happen? -- Explain>_____

A1c - [S] [O]   > Did you/he/she/they do something UNFORGIVABLE? -- Explain>_____

A2a - [Y] [N]   Will you probably be bothered by the (any of) above in the near future?
A2b - [S] [O]   > If YES, who will probably be RESPONSIBLE for making it happen? -- Explain>_____

A2c - [S] [O]   > Will you/he/she/they probably do something UNFORGIVABLE? -- Explain>_____

What has to happen for you NOT TO BE BOTHERED about the above?
_____
_____

When you think about the above, you feel:

ANNOYED/DISAPPOINTED with Yourself
- ANGRY at Yourself
- ASHAMED/EMBARRASSED
- GUILTY
Why do you feel this way? _____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL
Why do you feel this way? _____

* No. 9 *

Frequency of thoughts about:

NOT having enough FUN or EXCITEMENT
NOT having enough INTERESTING THINGS TO DO
being BORED
NOT having enough RELAXATION, COMFORT or PEACE OF MIND
being OVER-WORKED or OVER-STRESSED
how you DO NOT KNOW WHAT TO DO WITH YOUR LIFE
how your LIFE IS EMPTY, MEANINGLESS, or WITHOUT PURPOSE S=Self | O=Others (Both may be checked off)
A1a - [Y] [N]   Have you ever been bothered by (any of) the above?
A1b - [S] [O]   > If YES, who was RESPONSIBLE for making it happen? -- Explain>_____

A1c - [S] [O]     > Did you/he/she/they do something UNFORGIVABLE? – Explain>_____

A2a - [Y] [N]     Will you probably be bothered by the (any of) above in the near future?
A2b - [S] [O]     > If YES, who will probably be RESPONSIBLE for making it happen? – Explain>_____

A2c - [S] [O]     > Will you/he/she/they probably do something UNFORGIVABLE? – Explain>_____

What has to happen for you NOT TO BE BOTHERED about the above?_____

When you think about the above, you feel:

ANNOYED/DISAPPOINTED with Yourself
- ANGRY at Yourself
- ASHAMED/EMBARRASSED
- GUILTY
Why do you feel this way?_____

ANNOYED/DISAPPOINTED with Other People or Circumstances
- ANGRY at Others
Why do you feel this way?_____

SAD or UNHAPPY
- DEPRESSED
Why do you feel this way?_____

CONCERNED or UNEASY
- ANXIOUS/FEARFUL
Why do you feel this way?_____

* No. 10 *

Frequency of thoughts about:

the THINGS YOU HAVE DONE WRONG
the THINGS YOU MAY DO WRONG in the future

S=Self | O=Others (Both may be checked off)
A1a - [Y] [N]     Have you ever been bothered by (any of) the above?
A1b - [S] [O]     > If YES, who was RESPONSIBLE for making it happen? – Explain>_____

A1c - [S] [O]     > Did you/he/she/they do something UNFORGIVABLE? – Explain>_____

A2a - [Y] [N]     Will you probably be bothered by the (any of) above in the near future?
A2b - [S] [O]     > If YES, who will probably be RESPONSIBLE for making it happen? – Explain>_____

> Will you/he/she/they probably do something UNFORGIVABLE? – Explain>_____
A2c - [S] [O]

When you think about the above, you feel:

ANNOYED/DISAPPOINTED with Yourself
- ANGRY at Yourself
- ASHAMED/EMBARRASSED
- GUILTY
Why do you feel this way?_____

ANNOYED/DISAPPOINTED with Other People or Circumstances
- ANGRY at Others

Why do you feel this way? _____

SAD or UNHAPPY
- DEPRESSED
Why do you feel this way? _____

CONCERNED or UNEASY
- ANXIOUS/FEARFUL
Why do you feel this way? _____

* No. 11 *

Frequency of thoughts about:

the THINGS OTHERS HAVE DONE WRONG
the THINGS OTHERS MAY DO WRONG in the future

S=Self | O=Others (Both may be checked off)
A1a - [Y] [N]   Have you ever been bothered by (any of) the above?
A1b - [S] [O]   > If YES, who was RESPONSIBLE for making it happen? – Explain> _____

A1c - [S] [O]   > Did you/he/she/they do something UNFORGIVABLE? – Explain> _____

A2a - [Y] [N]   Will you probably be bothered by the (any of) above in the near future?
A2b - [S] [O]   > If YES, who will probably be RESPONSIBLE for making it happen? – Explain> _____

A2c - [S] [O]   > Will you/he/she/they probably do something UNFORGIVABLE? – Explain> _____

When you think about the above, you feel:

ANNOYED/DISAPPOINTED with Yourself
- ANGRY at Yourself
- ASHAMED/EMBARRASSED
- GUILTY
Why do you feel this way? _____

ANNOYED/DISAPPOINTED with Other People or Circumstances
- ANGRY at Others
Why do you feel this way? _____

SAD or UNHAPPY
- DEPRESSED
Why do you feel this way? _____

CONCERNED or UNEASY
- ANXIOUS/FEARFUL
Why do you feel this way? _____

COPING ATTEMPTS

You reported that you have been distressed thinking about certain problems. Please look at the list of problems below and think about how you have normally tried to handle, deal with, or cope with them when they have occured in the past. Finally, inciate whether your coping attempts have been successful.

Please use the followin scale when anwering:
[ D ]=Totally Disagree/False;   [ d ]=Mostly Disagree;   [ U ]=Uncertain;   [ a ]=Mostly Agree;   [ A ]=Totally Agree/True
[ 0 ] = NEVER Helps . . .   [ 4 ] = Helps a GREAT DEAL You have been thinking about the following problems:
BEING PHYSICALLY HURT; HANDICAPPED; HAVING A SERIOUS MENTAL or PHYSICAL ILLNESS or DISEASE; DYING
BEING REJECTED; RIDICULED; NOT HAVING ENOUGH LOVE; AFFECTION; ACCEPTANCE; APPROVAL; RECOGNITION NOT HAVING (or KEEPING) ENOUGH MONEY or POSSESSIONS
OTHER PEOPLE BEING PHYSICALLY or EMOTIONALLY HURT, ILL, UPSET; DYING
HOW CERTAIN PEOPLE DON'T CARE ABOUT WHAT YOU SAY; WHAT YOU WANT; DON'T RESPECT YOU; DON'T UNDE or CARE HOW YOU FEEL
HOW YOU CAN'T DEPEND ON OR TRUST CERTAIN PEOPLE
NOT HAVING ENOUGH FREEDOM OR INDEPENDENCE; NOT DOING CERTAIN THINGS ON YOUR OWN or BY YOURSEL PRESSURED TO DO THINGS YOU DON'T WANT TO DO
NOT TAKING GOOD ENOUGH CARE OF CERTAIN PEOPLE or HURTING THEM EMOTIONALLY or PHYSICALLY
NOT ENOUGH FUN or EXCITEMENT; INTERESTING THINGS TO DO; BORED; NOT ENOUGH RELAXATION, COMFORTS; NOT KNOW WHAT TO DO WITH YOUR LIFE; EMPTY
THE THINGS I HAVE DONE WRONG; WILL DO WRONG
THE THINGS OTHERS HAVE DONE WRONG; WILL DO WRONG If the problem was caused by another person or persons:
1a>[D] [d] [U] [a] [A]   I tell the person(s) who caused the problem how I feel and try to get them to change the way they act or think.
1b>[0] [1] [2] [3] [4]   How often does this help you to handle the situation?

If you caused the problem:
2a>[D] [d] [U] [a] [A]   I make sure that I know what I did to cause the problem and/or I appologize or try to make up for what I did.
2b>[0] [1] [2] [3] [4]   How often does this help you to handle the situation?

3a>[D] [d] [U] [a] [A]   I act as if nothing has happened or I try to put it out of my mind and not think about it much.
3b>[0] [1] [2] [3] [4]   How often does this help you to handle the situation?

4a>[D] [d] [U] [a] [A]   I try to control my feelings and take my time before I act.
4b>[0] [1] [2] [3] [4]   How often does this help you to handle the situation?

5a>[D] [d] [U] [a] [A]   I talk to someone about what I'm going through or I ask certain people for advice or help.
5b>[0] [1] [2] [3] [4]   How often does this help you to handle the situation?

6a>[D] [d] [U] [a] [A]   I try to spend time by myself, away from most people.
6b>[0] [1] [2] [3] [4]   How often does this help you to handle the situation?

7a>[D] [d] [U] [a] [A]   I hoped that a miracle would somehow make things better or that my dreams or wishes would be answered
7b>[0] [1] [2] [3] [4]   How often does this help you to handle the situation?

8a>[D] [d] [U] [a] [A]   I decide what I have to do to and then I use my plan to try to solve the problem.
8b>[0] [1] [2] [3] [4]   How often does this help you to handle the situation?

9a>[D] [d] [U] [a] [A]   I hoped that a miracle would somehow make things better
9b>[0] [1] [2] [3] [4]   How often does this help you to handle the situation?

10a>[D] [d] [U] [a] [A]  The problem helped me change or grow in a good way, helped me find new faith, or helped me re-discover what is important in life.
10b>[0] [1] [2] [3] [4]  How often does this help you to handle the situation?

11a>[D] [d] [U] [a] [A]  I accepted that there was nothing I could do about it, so I did nothing.
11b>[0] [1] [2] [3] [4]  How often does this help you to handle the situation?

GENERAL BACKGROUND INFORMATION

Is you mother alive? .............................................................................. [YES]  [NO]  [Uncertain]
Is your father alive? ............................................................................. [YES]  [NO]  [Uncertain]
Who presently lives with you:
o certain of my BROTHERS or SISTERS ........................................................ [YES]
o my SPOUSE or LOVER ...................................................................... [YES]
o certain of my CHILDREN .................................................................... [YES]
o certain of my STEP-CHILDREN .............................................................. [YES]
o certain of my FOSTER-CHILDREN ........................................................... [YES]
o my MOTHER ................................................................................ [YES]
o my MOTHER-IN-LAW ........................................................................ [YES]
o my FATHER ................................................................................ [YES]
o my FATHER-IN-LAW ........................................................................ [YES]
o my GRANDMOTHER .......................................................................... [YES]
o my GRANDFATHER .......................................................................... [YES]
o Other RELATIVES or IN-LAWs ............................................................... [YES]

Are you adopted? ................................................................................ [YES]
How many OLDER brothers or sisters do you have? ............. [0] [1] [2] [3] [4] [5] [6] [7] [8] [9] [10]
How many YOUNGER brothers or sisters do you have? .......... [0] [1] [2] [3] [4] [5] [6] [7] [8] [9] [10]
If YOU ARE DIVORCED, how many times have you re-married .................................. [0] [1] [2] [3] [4+]
If your PARENTS ARE DIVORCED, how old were you when they divorced? ....... [0-2] [3-5] [6-8] [9-11] [12-14] [15-17] [18+]

| What is your RACE: | What is your RELIGION: | How STRONG are your religious beliefs: | What is you FAMILY ORIGIN: |
|---|---|---|---|
| American Indian [ ] | Babtist [ ] | Very Strong Religious Beliefs [ ] | Africa [ ] |
| Asian [ ] | Buddhist [ ] | Strong Religious Beliefs [ ] | Asia [ ] |
| Black (Negroid) [ ] | Catholic [ ] | Moderate Religious Beliefs [ ] | Australia [ ] |
| White (Caucasion) [ ] | Christian Scientist [ ] | Weak Religious Beliefs [ ] | Central or South America [ ] |
| Indian [ ] | Episcopalian [ ] | Very Weak Religious Beliefs [ ] | United States of America [ ] |
| Oriental [ ] | Hindu [ ] | No Religious Beliefs (Athiest) [ ] | Baltics [ ] |
| Spanish [ ] | Jewish [ ] | Italy [ ] | Canada [ ] |
| <Other> [ ] | Lutheran [ ] | Japan [ ] | China [ ] |
| | Mormon [ ] | Middle East [ ] | Cuba [ ] |
| | Muslem, Islam [ ] | Puerto Rico [ ] | England [ ] |
| | Protestant [ ] | Russia (Soviet Union) [ ] | France [ ] |
| | <Other Religion> [ ] | Scandinavia [ ] | Greece [ ] |
| | NO Religion [ ] | Spain [ ] | India or Pakistan [ ] |
| | | | Indonesia [ ] |
| What is your SEX: | | | Ireland [ ] |

Appendix C page 1

What is your AGE? (in Years)

What is your WEIGHT? (in Pounds)

What is your HEIGHT? (Feet) (Inches)

Age columns: [0][0], [1][1][1], [2][2], [3][3], [4][4], [5][5], [6][6], [7][7], [8][8], [9][9]

Weight columns: [0][0][0], [1][1][1], [2][2][2], [3][3][3], [4][4][4], [5][5][5], [6][6][6], [7][7][7], [8][8][8], [9][9][9]

Height (Feet): [3], [4], [5], [6], [7], [8], [9]

Height (Inches): [0], [1], [2], [3], [4], [5], [6], [7], [8], [9]

What is your present occupation?

| Occupation | | Occupation | | Occupation | | Occupation | |
|---|---|---|---|---|---|---|---|
| Accountant | [ ] | Student | [ ] | Manufactoring | [ ] | Entertainment | [ ] |
| School/Gov't. Administrator | [ ] | Teacher | [ ] | Wholesale | [ ] | Financial/Banking | [ ] |
| Business Executive | [ ] | Religious worker | [ ] | Retail | [ ] | Layer/Judge | [ ] |
| Homemaker | [ ] | Politician | [ ] | Farming | [ ] | Military | [ ] |
| Insurance Broker/Sales | [ ] | Advertising/Marketing | [ ] | Public Relations | [ ] | Small Business Owner | [ ] |
| Real Estate Broker/Sales | [ ] | Architect | [ ] | Scientist-execept social | [ ] | Secretary | [ ] |
| Engineer | [ ] | Reasercher | [ ] | Physican | [ ] | Medical/Dental Aide | [ ] |
| Clerk | [ ] | Mathematician | [ ] | Cashier | [ ] | Landscaper | [ ] |
| Office worker | [ ] | Human Services worker | [ ] | Bankteller | [ ] | Construction worker | [ ] |
| Office manager | [ ] | Scientist-Social | [ ] | Mail delivery/clerk | [ ] | Cosmotology/Barber | [ ] |
| Food & beverage preparation/sevice | [ ] | Health assessment & treatment | [ ] | Health technologist/technician | [ ] | Mechanic, Installer or Repairer | [ ] |
| Occupational therapist | [ ] | Communications | [ ] | Computer programmer | [ ] | Truck/Bus/Cab driver | [ ] |
| Physical therapist | [ ] | Visual arts Performing arts | [ ] | Marketing & Sales | [ ] | Production worker - assemblers, processors operators, inspectors | [ ] |
| | | Animal care | [ ] | | | Production supervisor | [ ] |
| | | Cildcare worker | [ ] | | | Other | [ ] |

Have you ever had a head injury or disease with any of the following symptoms: .............................. [YES]
o concussion
o repeatedly seeing lights or stars
o coma
o seizures Where there any problems when you were born such as: ................................................. [YES]
o being deprived oxygen
o having head or spinal injury Do you smoke about a pack or more of cigarette most days? ................................................. [YES]

page 2

If you used to smoke cigarettes but stopped, did you quit "cold turkey?" ........................................ [YES]

How many cups of beverages containing caffeine (tea, coffee, cola) do you normally drink per day:   [0]  [1-2] [3-4] [4-5] [5-6] [over 6]

Do you have asthma or other serious allergies? ........................................................ [YES]

School Information

Highest grade completed in school: ........................... [1-6] [7-8] [9] [10] [11] [12] [13] [14] [15] [16] [over 17]

What was your average grades in elementary school? .............................................. [A] [B] [C] [D] [F]

What was your average grades in high school? ...................................................... [A] [B] [C] [D] [F]

Have you ever been retained (left back a grade) in school? ..................................................... [YES]

Have you been told that you have Learning Disabilities, Hyperactivity, or Attention Deficit Disorder? ............. [YES]

Other

Do you enjoy reading? ............................................................................... [YES]

Do you enjoy doing math or arithmetic? ............................................................... [YES]

page 3

Personal Information

Are you:
- SMART (INTELLIGENT) enough? ........................................................... [YES]
- STRONG, ATHLETIC, and COORDINATED enough? ............................... [YES]
- GOOD-LOOKING (ATTRACTIVE or HANDSOME) enough? ....................... [YES]
- SKILLFUL, KNOWLEDGEABLE, or TALENTED enough? ........................... [YES]
- PHYSICALLY HEALTHY enough? ............................................................. [YES]

Mental Health History

Have you ever received mental health services before? ............................... [YES]

> If YES, then what type(s) and for how much total time:
- Outpatient Individual psychotherapy ............. [less than 6 months] [6 mos to 1 year] [1-2 years] [2-3 years] [3-4 year] [over 4 years]
- Outpatient Marital/Couple/Pre-marital psychotherapy ... [less than 6 months] [6 mos to 1 year] [1-2 years] [2-3 years] [3-4 years] [over 4 years]
- Outpatient Family psychotherapy ............. [less than 6 months] [6 mos to 1 year [1-2 years] [2-3 years] [3-4 years] [over 4 years]
- Outpatient Group psychotherapy ............. [less than 6 months] [6 mos to 1 year] [1-2 years] [2-3 years] [3-4 years] [over 4 years]
- Treatment in a psychiatric hospital ............. [less than 6 months] [6 mos to 1 year] [1-2 years] [2-3 years] [3-4 years] [over 4 years]
- Treatment in a drug rehabilitation facility ............. [less than 6 months] [6 mos to 1 year] [1-2 years] [2-3 years] [3-4 years] [over 4 years]

Have you ever taken psychotherapeutic medication for a mental health problem? ............................... [YES]

> If YES, what type(s) and for how much total time:
- Anxiety/Panic Attacks/Phobias ............. [less than 6 months] [6 mos to 1 year] [1-2 years] [2-3 years] [3-4 years] [over 4 years]
- Depression ............. [less than 6 months] [6 mos to 1 year] [1-2 years] [2-3 years] [3-4 years] [over 4 years]
- Bipolar Disorder (Manic-Depression) ............. [less than 6 months] [6 mos to 1 year] [1-2 years] [2-3 years] [3-4 years] [over 4 years]
- Eating Disorder ............. [less than 6 months] [6 mos to 1 year] [1-2 years] [2-3 years] [3-4 years] [over 4 years]
- Obsessive-Compulsive Disorder ............. [less than 6 months] [6 mos to 1 year] [1-2 years] [2-3 years] [3-4 years] [over 4 years]
- Psychosis (Schizophrenia) ............. [less than 6 months] [6 mos to 1 year] [1-2 years] [2-3 years] [3-4 years] [over 4 years]
- Sleeping Disorder ............. [less than 6 months] [6 mos to 1 year] [1-2 years] [2-3 years] [3-4 years] [over 4 years]
- Alchohol-related Disorder ............. [less than 6 months] [6 mos to 1 year] [1-2 years] [2-3 years] [3-4 years] [over 4 years]
- Attention Deficit Disorder ( Hyperactivity) ............. [less than 6 months] [6 mos to 1 year] [1-2 years] [2-3 years] [3-4 years] [over 4 years]

What types of prescription medication do you presently take:
- Cardiac or antihypertension drugs ................................................................. [YES]
- Sedatives ................................................................. [YES]
- Steroids or hormones ................................................................. [YES]

Which of the following illnesses or diseases do you have:
- Coronary heart disease ................................................................. [YES]
- Cardiovascular discease or Cardiac arrhythmias ................................................................. [YES]
- Cancer ................................................................. [YES]
- Diabetes ................................................................. [YES]
- Parkinson's disease, Huntington's disease, or Wilson's disease ................................................................. [YES]
- Cerebrovascular disease ................................................................. [YES]
- Multiple sclerosis ................................................................. [YES]
- Hyperthyroidism ................................................................. [YES]
- Herpes or other Venerial diseases ................................................................. [YES]
- AIDS ................................................................. [YES]
- Epilepsy ................................................................. [YES]
- Lupus or Rhematoid athritis ................................................................. [YES]
- Anemia ................................................................. [YES]

page 4

This section examines any sleeping or eating problems that you may be experiencing. Answer each statement below by placing a mark in the [ T ] box if the statement is MOSTLY TRUE or mark the [ F ] box if the statement is MOSTLY FALSE.

| [ True ] = Usually or Mostly TRUE; [ False ] = Usually or Mostly FALSE |
|---|

EATING and BODY WEIGHT problems

| | | | | | | |
|---|---|---|---|---|---|---|
| How many pounds have you GAINED in the last 2 months? | [ 0-5 ] | [6-10] | [11-15] | [16-20] | [21-25] | [ 26 +] |
| How many pounds have you LOST in the last 2 months? | [ 0-5 ] | [6-10] | [11-15] | [16-20] | [21-25] | [ 26 +] |

I am very unhappy with the shape of my body because I am overweight ............ [True] [False]

I am very fearful of gaining weight and becoming fat (or fatter) ............ [True] [False]

I eat very little because I am losing my appetite for most foods ............ [True] [False]

I eat too much because I have trouble controlling how much I eat ............ [True] [False]

At times I "binge" eat (I eat large amounts of good-tasting foods in a very short period of time) ............ [True] [False]

I have recently used one or more of the following methods of weight control: ............ [True] [False]
o fasting (not eating anything)
o making myself vomit
o using laxatives or diuretics,

SLEEPING problems

I have much trouble falling or staying asleep ............ [True] [False]

I have nightmares (bad dreams) every few nights ............ [True] [False]

It takes me a very long time to feel fully awake after I wake up ............ [True] [False]

I sometimes walk in my sleep ............ [True] [False]

This section examines your physical symptoms (things that happen in your body). Look over the list of symptoms below. Next to each of the symptoms, mark the appropriate boxes using the following scale:

Indicate how much of a problem is caused by the symptom on a scale from
[ 0 ] = NEVER HAPPENS to [ 4 ] = HAPPENS OFTEN and is VERY SERIOUS or UNCOMFORTABLE If you or your doctor KNOW the medical cause of the symptom, check off the [ K ] box; If the medical cause is not known, leave it blank.

If you have PANIC ATTACKS (sudden, unexpected feelings of great panic or fear), and the symptom occurs *ONLY* during PANIC ATTACKS, then mark the [ PA ] box

[ 0 ] = NEVER Happens . . . [ 4 ] = Happens OFTEN and is VERY SERIOUS or UNCOMFORTABLE;
[ K ] = medical cause is KNOWN;  [PA] = Panic Attack;

STOMACH, SWALLOWING, or DIGESTION problems:
- abdominal pain (other than when menstruating) ............ [0] [1] [2] [3] [4] --- [K] --- [PA]
- bloating (gassy) ............ [0] [1] [2] [3] [4] --- [K] --- [PA]
- diarrhea ............ [0] [1] [2] [3] [4] --- [K] --- [PA]
- constipation ............ [0] [1] [2] [3] [4] --- [K] --- [PA]
- acid indigestion or an upset stomach ............ [0] [1] [2] [3] [4] --- [K] --- [PA]
- nausea or vomiting (other than motion sickness or during pregnancy) .... [0] [1] [2] [3] [4] --- [K] --- [PA]
- intolerance of (gets sick from) several different foods ............ [0] [1] [2] [3] [4] --- [K] --- [PA]
- difficulty swallowing or "lump in the throat" ............ [0] [1] [2] [3] [4] --- [K] --- [PA]
- dry mouth ............ [0] [1] [2] [3] [4] --- [K] --- [PA]
- urinary retention or difficulty urinating ............ [0] [1] [2] [3] [4] --- [K] --- [PA]
- frequent urination ............ [0] [1] [2] [3] [4] --- [K] --- [PA]

ACHES and PAINS in BODY
- pain in extremities ............ [0] [1] [2] [3] [4] --- [K] --- [PA]
- back pain ............ [0] [1] [2] [3] [4] --- [K] --- [PA]
- joint pain ............ [0] [1] [2] [3] [4] --- [K] --- [PA]
- chest pain or discomfort ............ [0] [1] [2] [3] [4] --- [K] --- [PA]
- pain during urination ............ [0] [1] [2] [3] [4] --- [K] --- [PA]
- pain in the jaw when opened and closed ............ [0] [1] [2] [3] [4] --- [K] --- [PA]
- muscle aches or soreness ............ [0] [1] [2] [3] [4] --- [K] --- [PA]
- other pain ............ [0] [1] [2] [3] [4] --- [K] --- [PA]

HEADACHES
- headaches (other than Migraine Headaches) ............ [0] [1] [2] [3] [4] --- [K] --- [PA]
- Do you have MIGRAINE HEADACHES? ............ [YES]

Feeling DIZZY, FAINT, SWEATING, or FLUSHED
- dizziness or lightheadedness ............ [0] [1] [2] [3] [4] --- [K] --- [PA]
- feeling faint or loss of consciousness ............ [0] [1] [2] [3] [4] --- [K] --- [PA]
- seizure or convulsion ............ [0] [1] [2] [3] [4] --- [K] --- [PA]
- sweating ............ [0] [1] [2] [3] [4] --- [K] --- [PA]
- cold clammy hands ............ [0] [1] [2] [3] [4] --- [K] --- [PA]
- flushes (hot flashes) or chills ............ [0] [1] [2] [3] [4] --- [K] --- [PA]

| [ 0 ] = NEVER Happens . . . [ 4 ] = Happens OFTEN and is a SERIOUS PROBLEM or DISCOMFORT; |
| --- |
| [ K ] = medical cause is KNOWN; [PA] = Panic Attack; | feeling TENSE, AGITATED, or RESTLESS
- o feeling restless or on edge ............................................. [ 0] [ 1] [ 2] [ 3] [ 4] --- [ K ] --- [PA]
- o easily startled or jumpy ................................................ [ 0] [ 1] [ 2] [ 3] [ 4] --- [ K ] --- [PA]
- o irritable, tense, agitated, or unable to relax ........................ [ 0] [ 1] [ 2] [ 3] [ 4] --- [ K ] --- [PA]
- o trembling, twitching, jittery, or feeling shaky ...................... [ 0] [ 1] [ 2] [ 3] [ 4] --- [ K ] --- [PA]

NUMBNESS, TINGLING, TROUBLE WALKING
- o numbness or tingling sensations ..................................... [ 0] [ 1] [ 2] [ 3] [ 4] --- [ K ] --- [PA]
- o trouble walking ........................................................... [ 0] [ 1] [ 2] [ 3] [ 4] --- [ K ] --- [PA]

BREATHING problems
- o shortness of breath when not exerting yourself ..................... [ 0] [ 1] [ 2] [ 3] [ 4] --- [ K ] --- [PA]
- o smothering sensations (like you can't breath or are choking) ...... [ 0] [ 1] [ 2] [ 3] [ 4] --- [ K ] --- [PA]

HEART BEAT problems
- o heart beating hard (palpitations) ..................................... [ 0] [ 1] [ 2] [ 3] [ 4] --- [ K ] --- [PA]
- o heart beating very fast (tachycardia) ................................ [ 0] [ 1] [ 2] [ 3] [ 4] --- [ K ] --- [PA]

VISION, HEARING, and VOICE problems
- o double vision ............................................................. [ 0] [ 1] [ 2] [ 3] [ 4] --- [ K ] --- [PA]
- o blurred vision ............................................................ [ 0] [ 1] [ 2] [ 3] [ 4] --- [ K ] --- [PA]
- o blindness ................................................................... [ 0] [ 1] [ 2] [ 3] [ 4] --- [ K ] --- [PA]
- o deafness ................................................................... [ 0] [ 1] [ 2] [ 3] [ 4] --- [ K ] --- [PA]
- o loss of voice .............................................................. [ 0] [ 1] [ 2] [ 3] [ 4] --- [ K ] --- [PA]

Feeling WEAK, TIRED, LACKING ENERGY
- o feeling sluggish, easily tired, like you have no energy .............. [ 0] [ 1] [ 2] [ 3] [ 4] --- [ K ]
- o feeling unrested or sleepy during the day, even after a full night's sleep ... [ 0] [ 1] [ 2] [ 3] [ 4] --- [ K ]
- o muscles feel weak or paralyzed ...................................... [ 0] [ 1] [ 2] [ 3] [ 4] --- [ K ]

SEXUAL problems
- o burning sensations in sexual organs or rectum (other than during intercourse)  [ 0] [ 1] [ 2] [ 3] --- [ 4 ] --- [ K ]
- o pain during intercourse ................................................. [ 0] [ 1] [ 2] [ 3] [ 4] --- [ K ]
- o loss of interest in sex (loss of desire for sex) ...................... [ 0] [ 1] [ 2] [ 3] [ 4] --- [ K ]
- o impotence ................................................................. [ 0] [ 1] [ 2] [ 3] [ 4] --- [ K ]

FEMALE problems, including:
- o painful menstruation .................................................... [ 0] [ 1] [ 2] [ 3] [ 4] --- [ K ]
- o irregular menstrual periods ........................................... [ 0] [ 1] [ 2] [ 3] [ 4] --- [ K ]
- o excessive menstrual bleeding ......................................... [ 0] [ 1] [ 2] [ 3] [ 4] --- [ K ]

CURRENT PROBLEMS OR DIFFICULTIES

*Please answer the following using the scale below:*

| [ 0 ] = NOT a Problem . . . [ 4 ] = A HUGE Problem |
|---|

How much of a problem are you having because of the following:

Problems with WORK or SCHOOL

I am unemployed or I am likely to lose my job ................................................... [ 0 ] [ 1 ] [ 2 ] [ 3 ] [ 4 ]
I don't like my present job or school class(es) .................................................. [ 0 ] [ 1 ] [ 2 ] [ 3 ] [ 4 ]
I'm performing poorly (I'm not doing a good job) at work or in school ............................ [ 0 ] [ 1 ] [ 2 ] [ 3 ] [ 4 ]
There is too much stress at work or in school ................................................... [ 0 ] [ 1 ] [ 2 ] [ 3 ] [ 4 ]

Problems with my LIVING or WORKING ENVIRONMENT

I live in a bad neighborhood .................................................................... [ 0 ] [ 1 ] [ 2 ] [ 3 ] [ 4 ]
My home/apartment is too small or in need of repair ............................................. [ 0 ] [ 1 ] [ 2 ] [ 3 ] [ 4 ]
I live too far from work or school .............................................................. [ 0 ] [ 1 ] [ 2 ] [ 3 ] [ 4 ]
My workplace or school is unsafe ................................................................ [ 0 ] [ 1 ] [ 2 ] [ 3 ] [ 4 ]
I have recently moved or I will be moving in the near future .................................... [ 0 ] [ 1 ] [ 2 ] [ 3 ] [ 4 ]

LEGAL problems

I am going to court or am being punished for a non-assaultive crime (I did not hurt anyone) ...... [ 0 ] [ 1 ] [ 2 ] [ 3 ] [ 4 ]
I am going to court or am being punished for an assaultive crime (I did hurt someone) ........... [ 0 ] [ 1 ] [ 2 ] [ 3 ] [ 4 ]
I have other legal problems ..................................................................... [ 0 ] [ 1 ] [ 2 ] [ 3 ] [ 4 ]

DEATH or serious ILLNESS of a LOVED ONE or FAMILY MEMBER

A parent of mine has died or is seriously ill ................................................... [ 0 ] [ 1 ] [ 2 ] [ 3 ] [ 4 ]
My spouse, boyfriend, girlfriend has died or is seriously ill ................................... [ 0 ] [ 1 ] [ 2 ] [ 3 ] [ 4 ]
A child of mine has died or is seriously ill .................................................... [ 0 ] [ 1 ] [ 2 ] [ 3 ] [ 4 ]
A sibling (brother or sister) of mine has died or is seriously ill .............................. [ 0 ] [ 1 ] [ 2 ] [ 3 ] [ 4 ]
Another close family member or friend of mine has died or is seriously ill ...................... [ 0 ] [ 1 ] [ 2 ] [ 3 ] [ 4 ]

Other problems

If you are a MALE: My partner recently got pregnant or I recently became a parent ............... [ 0 ] [ 1 ] [ 2 ] [ 3 ] [ 4 ]
If you are FEMALE: I recently became pregnant or gave birth ..................................... [ 0 ] [ 1 ] [ 2 ] [ 3 ] [ 4 ]
If you WANT TO BE a PARENT: We are unable to have children ...................................... [ 0 ] [ 1 ] [ 2 ] [ 3 ] [ 4 ]
I have recently become the victim of a natural disaster ......................................... [ 0 ] [ 1 ] [ 2 ] [ 3 ] [ 4 ]
If family member, loved one, or close friend is having serious troubles ......................... [ 0 ] [ 1 ] [ 2 ] [ 3 ] [ 4 ]
If you are going to RETIRE shortly or have already retired: My retirement is a problem ........... [ 0 ] [ 1 ] [ 2 ] [ 3 ] [ 4 ]

| [ 0 ] = NOT a Problem . . . [ 4 ] = A HUGE Problem |
|---|

How much of a problem are you having because of the following:

Problems with PEOPLE

| | |
|---|---|
| I don't get along with certain of my parents or guardians | [ 0 ] [ 1 ] [ 2 ] [ 3 ] [ 4 ] |
| I don't get along with certain of my brothers or sisters | [ 0 ] [ 1 ] [ 2 ] [ 3 ] [ 4 ] |
| I don't get along with my spouse, boyfriend or girlfriend | [ 0 ] [ 1 ] [ 2 ] [ 3 ] [ 4 ] |
| If you a parent: I have trouble with certain of my children or stepchildren | [ 0 ] [ 1 ] [ 2 ] [ 3 ] [ 4 ] |
| If you are divorced or have ended a relationship: I am having trouble with an ex-spouse or ex-lover | [ 0 ] [ 1 ] [ 2 ] [ 3 ] [ 4 ] |
| I don't get along with certain extended family members (grandparents, aunts, uncles, or cousins) | [ 0 ] [ 1 ] [ 2 ] [ 3 ] [ 4 ] |
| I have problems with certain bosses or teachers or other people in authority | [ 0 ] [ 1 ] [ 2 ] [ 3 ] [ 4 ] |
| I don't get along with my certain of my co-workers or classmates | [ 0 ] [ 1 ] [ 2 ] [ 3 ] [ 4 ] |
| I don't have enough friends or close companions; I am lonely | [ 0 ] [ 1 ] [ 2 ] [ 3 ] [ 4 ] |
| I cannot find the right mate/boyfriend/girlfriend | [ 0 ] [ 1 ] [ 2 ] [ 3 ] [ 4 ] |
| I am upset over a failing or failed love relationship | [ 0 ] [ 1 ] [ 2 ] [ 3 ] [ 4 ] |
| I avoid certain people or situations because I am afraid that I others will judge me poorly or I worry that I might do something that makes me feel humiliated, embarrassed, or look stupid | [ 0 ] [ 1 ] [ 2 ] [ 3 ] [ 4 ] |
| I feel shy, anxious, or uncomfortable around new people | [ 0 ] [ 1 ] [ 2 ] [ 3 ] [ 4 ] |
| People expect me to do certain things that are too difficult, dangerous or risky for me to do | [ 0 ] [ 1 ] [ 2 ] [ 3 ] [ 4 ] |
| I am reluctant to enter into new relationships because I do not want to be rejected or hurt | [ 0 ] [ 1 ] [ 2 ] [ 3 ] [ 4 ] |
| I don't stand up for my rights; I let people push me around too much | [ 0 ] [ 1 ] [ 2 ] [ 3 ] [ 4 ] |
| People get upset with me because they don't understand some of the things I say or do | [ 0 ] [ 1 ] [ 2 ] [ 3 ] [ 4 ] |
| I am disappointed with some of the friends I make | [ 0 ] [ 1 ] [ 2 ] [ 3 ] [ 4 ] |
| When I get close to someone, I just know that the relationship will soon turn bad or fall apart | [ 0 ] [ 1 ] [ 2 ] [ 3 ] [ 4 ] |
| I keep becoming attracted to the sort of person that I have had trouble with in the past | [ 0 ] [ 1 ] [ 2 ] [ 3 ] [ 4 ] |
| When close relationships end, I feel crushed or I feel helpless because I can't do anything about it | [ 0 ] [ 1 ] [ 2 ] [ 3 ] [ 4 ] |
| One (or both) of my parents has a drinking or drug problem | [ 0 ] [ 1 ] [ 2 ] [ 3 ] [ 4 ] |
| My spouse/boyfriend/girlfriend has a drinking or drug problem | [ 0 ] [ 1 ] [ 2 ] [ 3 ] [ 4 ] |
| If you are a parent: One (or more) of my children has a drinking or drug problem | [ 0 ] [ 1 ] [ 2 ] [ 3 ] [ 4 ] |

VICTIM of ACCIDENT, ABUSE or CRIME

| | |
|---|---|
| I have been the victim of a serious accident | [ 0 ] [ 1 ] [ 2 ] [ 3 ] [ 4 ] |
| I have been criminally attacked or assaulted (including being raped) | [ 0 ] [ 1 ] [ 2 ] [ 3 ] [ 4 ] |
| I have been the victim of a non-assaultive crime (I was not physically harmed) | [ 0 ] [ 1 ] [ 2 ] [ 3 ] [ 4 ] |

EXAMINING YOUR EMOTIONS

*Please answer the following using the scale below:*

| [ True ] = Usually or Mostly TRUE | [ False ] = Usually or Mostly FALSE |
|---|---|

When I feel depressed, I tend to awake early in the morning (at least 2 hours before I usually awake) ............... [True] [False]
When I am depressed, I normally feel the worst in the morning ............................................. [True] [False]
When I get depressed, my depression normally lasts for more than a day or two ............................. [True] [False]
I get depressed during certain seasons of the year, but not others ........................................ [True] [False]
When I am really angry, I have trouble controlling my temper ............................................. [True] [False]
When I lose my temper, I tend to break things or do things that hurt people .............................. [True] [False]
I have certain fears that are unrealistic or excessive; that is, I am afraid of certain things or situations
that are <u>unlikely</u> to cause me any real or lasting harm .................................................. [True] [False]
> If True, then do these fears interfere with your ability to function on your job (or at school) or
in social situations? ............................................................................. [Yes]
Openly expressing affectionate (warm and loving) feelings makes me feel uncomfortable ...................... [True] [False]
I sometimes feel like my life is not real, it's like I am living in a dream or movie; these feelings upset me ........... [True] [False]
I sometimes feel like I am observing myself from outside my body; these feelings upset me ..................... [True] [False]

*Please answer the following using the scale below:*

| [ 0 ] = NEVER Happens . . .   [ 4 ] = Happens a GREAT DEAL |
|---|

When I leave my home, I become afraid that I will be stuck in a place or situation where I can't escape .... [ 0 ] [ 1 ] [ 2 ] [ 3 ] [ 4 ]
I sometimes get sudden, unexpected feelings of panic or fear and feel like: .......................... [ 0 ] [ 1 ] [ 2 ] [ 3 ] [ 4 ]
- I am going to die, or
- I am going crazy or can't control what you are doing, or
- things are unreal,
- or I am not in my body I sometimes get extremely emotional, excitable, and full of energy for periods of time and I am not sure why
I feel that way ..................................................................................... [ 0 ] [ 1 ] [ 2 ] [ 3 ] [ 4 ]
I sometimes get strong, intense moods or feelings that change very quickly and make me think that my
emotions are unstable ............................................................................... [ 0 ] [ 1 ] [ 2 ] [ 3 ] [ 4 ]
I sometimes feel sorry (remorseful) about bad things I have done .................................... [ 0 ] [ 1 ] [ 2 ] [ 3 ] [ 4 ]
I sometimes get upset thinking about other people's problems ........................................ [ 0 ] [ 1 ] [ 2 ] [ 3 ] [ 4 ]

page 10

OTHER ISSUES

*Please answer the following using the scale below:*

| [ True ] = Usually or Mostly TRUE | [ False ] = Usually or Mostly FALSE |
|---|---|

| | | |
|---|---|---|
| I enjoy doing certain things that most people consider very dangerous | [True] | [False] |
| People do not give me enough credit or compliments for the work I do | [True] | [False] |
| I am a special kind of person with special kinds of problems that most people just don't understand | [True] | [False] |
| I believe that it is foolish to take risks in most things in life | [True] | [False] |
| I have found that it is usually better to live day to day than to a waste my time planning ahead | [True] | [False] |
| I have very little respect for most people in authority (such as bosses, teachers, or police); they have no right telling me what to do, so I do what I want to do | [True] | [False] |
| I have certain talents or abilities that are far superior to most other people | [True] | [False] |
| I really hate to give away or discard any of my possessions, even though people don't understand why I want to keep them | [True] | [False] |
| I have been very tense and upset as a result of a traumatic event (very frightening or life-threatening experience) | [True] | [False] |
| I get very upset or distressed when I think about one or more of the following issues: | [True] | [False] |

- What should be my long-term goals, career or occupation?
- Who are my real friends?
- What is the right sexual activities for me?
- What is the right religion or religious beliefs for me?
- What moral values should I accept (what is right and what is wrong)?
- What groups should I belong to?

| | | |
|---|---|---|
| I have been involved in a totally monogamous relationship (intimate with only one person) for more than one year | [True] | [False] |
| I hate to be alone | [True] | [False] |
| I am very quiet and hardly talk at all when I am with a group of people who are not my close friends | [True] | [False] |
| If I take the time to show someone the right way to do something, it bothers me greatly if he/she doesn't do it the right way. | [True] | [False] |
| People should follow all moral laws and never do anything considered wrong | [True] | [False] |
| I hear voices in my head that talk to each other or a voice that makes comments on what I am doing or thinking | [True] | [False] |
| I can see people, animals, or things that others cannot see | [True] | [False] |
| I can hear voices that others cannot hear | [True] | [False] |
| Other people can sometimes hear my thoughts | [True] | [False] |
| Spirits of the dead possess me at times | [True] | [False] |
| Someone or something has control over my mind or body at times | [True] | [False] |
| Certain people want to hurt me or get me for some special reason | [True] | [False] |
| I have been convicted of DWI (driving while intoxicated or impaired) | [True] | [False] |
| I have used certain "street drugs" (such as pot, cocaine, LSD, or heroine) in order to feel good | [True] | [False] |
| Have you ever drunk alcohol and later could not remember what you had done? | [True] | [False] |
| Have you ever overdosed on drugs or alcohol? | [Yes] | |
| Have you ever received drug or alcohol rehabilitation counseling | [Yes] | |
| I am not always truthful | [True] | [False] |
| I sometimes gossip a little | [True] | [False] | page 11

*Please answer the following using the scale below:*

| [ 0 ] = NEVER Happens . . . [ 4 ] = Happens a GREAT DEAL |
|---|

| | |
|---|---|
| I have difficulty concentrating, making decisions, or finishing things that I have started | [ 0 ] [ 1 ] [ 2 ] [ 3 ] [ 4 ] |
| I am easily distracted by things that happening around me | [ 0 ] [ 1 ] [ 2 ] [ 3 ] [ 4 ] |
| I feel restless, fidgety, or I have the urge to be very active or "on the go" | [ 0 ] [ 1 ] [ 2 ] [ 3 ] [ 4 ] |
| I get impatient when things take longer than expected or when I have to wait for things I really want | [ 0 ] [ 1 ] [ 2 ] [ 3 ] [ 4 ] |
| I get into trouble when I say or do things without thinking of the consequences | [ 0 ] [ 1 ] [ 2 ] [ 3 ] [ 4 ] |
| I keep putting off or postponing doing certain important things | [ 0 ] [ 1 ] [ 2 ] [ 3 ] [ 4 ] |
| I have a poor memory, I tend to forget to do certain things | [ 0 ] [ 1 ] [ 2 ] [ 3 ] [ 4 ] |
| I feel rejected or uncomfortable if someone important to me fails to give me most of his or her attention | [ 0 ] [ 1 ] [ 2 ] [ 3 ] [ 4 ] |
| I am not satisfied with things I start to do | [ 0 ] [ 1 ] [ 2 ] [ 3 ] [ 4 ] |
| I must do certain things over and over and over again because something in my mind tells me to keep doing it | [ 0 ] [ 1 ] [ 2 ] [ 3 ] [ 4 ] |
| Certain people complain that I spend too much time working | [ 0 ] [ 1 ] [ 2 ] [ 3 ] [ 4 ] |
| I am afraid that someone important to me is going to leave or be gone forever | [ 0 ] [ 1 ] [ 2 ] [ 3 ] [ 4 ] |
| I allow others to make my major decisions | [ 0 ] [ 1 ] [ 2 ] [ 3 ] [ 4 ] |
| I get upset when there is no one to assure me that my problems will turn out all right | [ 0 ] [ 1 ] [ 2 ] [ 3 ] [ 4 ] |
| When I want certain people to like me, I agree with them even when they are wrong | [ 0 ] [ 1 ] [ 2 ] [ 3 ] [ 4 ] |
| When I want certain people to like me, I do things that I don't really want to do | [ 0 ] [ 1 ] [ 2 ] [ 3 ] [ 4 ] |
| I get involved in relationships that quickly become intense ("hot and heavy") then soon fall apart | [ 0 ] [ 1 ] [ 2 ] [ 3 ] [ 4 ] |
| There are periods of time when my thoughts race ahead very fast | [ 0 ] [ 1 ] [ 2 ] [ 3 ] [ 4 ] |
| Certain thoughts, ideas, or images -- that are senseless or disturbing -- keep repeating in my mind even though I wish they would stop | [ 0 ] [ 1 ] [ 2 ] [ 3 ] [ 4 ] |
| Certain people complain that I drink too much (beer, wine, liquor, etc.) or get "high" too often | [ 0 ] [ 1 ] [ 2 ] [ 3 ] [ 4 ] |
| My drinking or drug use causes problems in my life | [ 0 ] [ 1 ] [ 2 ] [ 3 ] [ 4 ] |

*Please answer the following using the scale below:*

| [ True ] = Usually or Mostly TRUE  /  [ False ] = Usually or Mostly FALSE  /  [ Uncertain ] |
|---|

| | | | |
|---|---|---|---|
| One (or both) of my parents have a serious emotional (mental, psychiatric) problem | [ True ] | [ False ] | [ Uncertain] |
| One (or more) of my brothers or sisters has a serious emotional (mental, psychiatric) problem | [True ] | [ False ] | [ Uncertain] |
| If you are a parent: One (or more) of my children has a serious emotional (mental, psychiatric) problem | [ True ] | [ False ] | [ Uncertain] |
| I feel that my life is hopeless | [ True ] | [ False ] | [ Uncertain] |
| I believe that death would be a good way to end my problems | [ True ] | [ False ] | [ Uncertain] |
| Certain people would be better off if I were dead | [ True ] | [ False ] | [ Uncertain] |
| I have family members or friends who attempted or committed suicide | [ True ] | [ False ] | [ Uncertain] |
| I have been seriously thinking of killing myself and know how to do it | [ True ] | [ False ] | [ Uncertain] | page 12

MENTAL-BEHAVIORAL STATUS EXAMINATION

*To be completed by the CLINICIAN*

Mark an "X" in the boxes next to all signs and symptoms that are TRUE or evident at a PSYCHOPATHOLICAL LEVEL based on the client's answers and/or on your clinical observations. Indicate the SEVERITY or FREQUENCY of your observations using the following scale:

| 1 = Moderately Severe or Often occurs | 2 = Severe or Usually occurs | 3 = Very Severe or Almost Always occurs |
|---|---|---|

PHYSICAL APPEARANCE

HYGIENE, GROOMING, AND DRESS:
- STRONG BODY ODOR .................................................................................................... [1] [2] [3]
- SOILED/WORN/TORN CLOTHING .................................................................................. [1] [2] [3]
- DISHEVELED/UNKEMPT APPEARANCE ........................................................................ [1] [2] [3]
- EXTREME NEATNESS ..................................................................................................... [1] [2] [3]
- Inappropriately SEDUCTIVE APPAREL and/or BEHAVIOR ............................................ [1] [2] [3]
- FLAMBOYANT OUTFIT / MISMATCHED CLOTHING / LOUD MAKEUP ........................ [1] [2] [3]

EYE CONTACT:
- WANDERING EYES .......................................................................................................... [1] [2] [3]
- AVOIDANCE OF EYE CONTACT ..................................................................................... [1] [2] [3]
- CONSTANT TRACKING ................................................................................................... [1] [2] [3]

OTHER:
- RED HANDS ..................................................................................................................... [1] [2] [3]
- RED NOSE ........................................................................................................................ [1] [2] [3]
- BLOODSHOT EYES .......................................................................................................... [1] [2] [3]
- DILATED PUPILS ............................................................................................................. [1] [2] [3]
- CONSTRICTED PUPILS ................................................................................................... [1] [2] [3]
- EXCESSIVE PERSPIRATION (on forehead, hands, etc.) ................................................. [1] [2] [3]
- Family history of allergies or asthma or looks or acts allergic (see symptoms below): ..... [1] [2] [3]
    - Red ear lobes, cheeks, eyes
    - Glassy eyes
    - Bags under eyes
    - Clucking throat sounds
    - Snorting sounds
    - Itchy skin
    - Extreme reactions to certain foods

FACTITIOUS SYMPTOMS

- Is the individual intentionally producing or feigning psychological symptoms? ................. [1] [2] [3]
- Is the individual intentionally producing or feigning physiological symptoms? .................. [1] [2] [3]

Appendix D page 1

| 1 = Moderately Severe or Often occurs | 2 = Severe or Usually occurs | 3 = Very Severe or Almost Always occurs |
|---|---|---|

PSYCHOSOMATIC SYMPTOMS o Impairment in physical functioning is etiologically related to psychosocial stressors or conflicts ........................................ [1] [2] [3]
o The symptoms are NOT culturally sanctioned and have no apparent physiological/medical cause (i.e.,
  the symptoms are not due to organic pathology or pathophysiologic mechanisms) .................................................... [1] [2] [3]
o If related organic pathology exists, the person's complaints or impairment of social/occupational
  functioning is grossly in excess of reasonable expectations based on the medical findings ......................................... [1] [2] [3]
o Is the person fearfully preoccupied with the belief that he/she has a serious disease despite medical reassurance to the contrary? ............ [1] [2] [3]
  ▪ YES, does the person acknowledge that his/her belief may be incorrect or exaggerated (i.e., it is NON-DELUSIONAL)? ............... [1] [2] [3]
o Does the person have a history in which he/she as had many physical complaints or has often felt sickly, prior to age 30
  and persisting for several years? ................................................................................................. [1] [2] [3]

DISORDERED EATING BEHAVIORS o EXCESSIVE eating (Overeating) ................................................................................................. [1] [2] [3]
o UNDEREATING
  ▪ POOR APPETITE ............................................................................................................ [1] [2] [3]
  ▪ EXCESSIVE DIETING or FASTING .............................................................................................. [1] [2] [3]
  ▪ VOMITING or USE OF LAXATIVES .............................................................................................. [1] [2] [3]
  ▪ BINGING and PURGING ....................................................................................................... [1] [2] [3]

DISORDERED SLEEPING BEHAVIORS o INSOMNIA - Difficulty in initiating or maintaining sleep, or sleep that is non-restorative ........................................ [1] [2] [3]
  ▪ Frequency of insomnia - Average number of nights per week :    [1] [2] [3] [4] [5] [6] [7]
  ▪ Duration of insomnia - How many month has it occurred within the past year:    [under 1] [1-2] [3-4] [5-6] [7-8] [9 +]
  ▪ If Insomnia occurs, does it result in daytime fatigue or some impairment in daytime functioning .................................. [1] [2] [3]
o HYPERSOMNIA - Excessive daytime sleepiness or frequent daytime sleep episodes .................................................... [1] [2] [3]
o SLEEP-WAKE SCHEDULE DISORDER - Complaint for either insomnia or hypersomnia occur as a result of a mismatch between
  the normal sleep-wake schedule for a person's environment and his/her circadian sleep-wake pattern ................................. [1] [2] [3]
o DREAM ANXIETY DISORDER (NIGHTMARE DISORDER) - Repeated awakening by frightening dreams that can be recalled ........... [1] [2] [3]
o SLEEP TERROR DISORDER - Abrupt awakening from sleep with intense anxiety reaction, but no detailed dream is recalled .............. [1] [2] [3]
o SLEEPWALKING DISORDER (SOMNAMBULISM) ............................................................................................. [1] [2] [3]

1 = Moderately Severe or Often occurs    2 = Severe or Usually occurs    3 = Very Severe or Almost Always occurs

SUBSTANCE ABUSE

- The person used the substance in GREATER AMOUNTS or for LONGER PERIODS of time than initially intended ........ [1] [2] [3]
- The excessive use of the substance continues despite attempts to stop or limit its use .................................. [1] [2] [3]
- A strong desire for the substance persists ................................................................................ [1] [2] [3]
- The acquisition, use, or recovery from the effects of the substance requires a great deal of time ...................... [1] [2] [3]
- The symptoms of intoxification and/or withdrawal frequently interfere with major social and/or occupational (including school) responsibilities or create potentially hazardous situations (e.g., overdosing or driving while intoxicated) .................. [1] [2] [3]
- The substance use causes the person to give up or reduce important recreational activities ............................. [1] [2] [3]
- Despite acknowledging the deleterious effects of the substance on the person's psychological, physical, and/or social life, the substance use continues ................................................................................................ [1] [2] [3]
- TOLERANCE: Over a 50% increase in substance use before desired intoxification effect is achieved, or a markedly diminished effect when the same amount is continually used ........................................ [1] [2] [3]
- WITHDRAWAL
  - withdrawal symptoms ................................................................................................ [1] [2] [3]
  - Withdrawal symptoms are often relieved or avoided by use of the substance ...................................... [1] [2] [3]

SUICIDAL IDEATION AND BEHAVIOR

- HELPLESS / HOPELESS - Believes that one's serious problems are insurmountable .................................. [1] [2] [3]
- Believes that DEATH is a DESIRED MEANS of SOLVING ONE'S PROBLEMS ........................................ [1] [2] [3]
- Has been SERIOUSLY THINKING of KILLING ONESELF ........................................................ [1] [2] [3]
- Has a REALISTIC PLAN for killing oneself ................................................................... [1] [2] [3]
- Has previously THREATENED or ATTEMPTED SUICIDE ........................................................ [1] [2] [3]
- Knows of others (family members or friends) who have attempted or committed suicide ............................. [1] [2] [3]

Self-Mutilating Behavior

- Engages in VOLUNTARY SELF-MUTILATING BEHAVIOR ........................................................... [1] [2] [3]
- Engages in INVOLUNTARY SELF-MUTILATING BEHAVIOR ......................................................... [1] [2] [3]

1 = Moderately Severe or Often occurs    2 = Severe or Usually occurs    3 = Very Severe or Almost Always occurs

Disturbances of Sexual Behaviors

Paraphilias:

- EXHIBITIONISM - For a period of 6 months or more, there have been recurrent intense sexual urges and fantasies involving genital exposure to unsuspecting strangers ........................................ [1] [2] [3]
  - If YES, the person either acted on these urges or was markedly distressed by them ........................................ [1] [2] [3]
- FETISHISM - For a period of 6 months or more, there have been recurrent intense sexual urges and fantasies involving the use of nonliving objects (but not limited to the use of female garments used for cross-dressing or devices used for genital stimulations such as vibrators) ..... [1] [2] [3]
  - If YES, the person either acted on these urges or was markedly distressed by them ........................................ [1] [2] [3]
- FROTTEURISM - For a period of 6 months or more, there have been recurrent intense sexual urges and fantasies involving rubbing against or touching an unsuspecting, nonconsenting person ........................................ [1] [2] [3]
  - If YES, the person either acted on these urges or was markedly distressed by them ........................................ [1] [2] [3]
- PEDOPHILIA - For a period of 6 months or more, there have been recurrent intense sexual urges and fantasies involving sexual activity with one or more prepubescent children ) ........................................ [1] [2] [3]
  - If YES, the person either acted on these urges or was markedly distressed by them and is at least 16 years of age and at least 5 years older than the child ........................................ [1] [2] [3]
- SEXUAL MASOCHISM - For a period of 6 months or more, there have been recurrent intense sexual urges and fantasies involving actual humiliation, beating, bounding, or other painful acts ........................................ [1] [2] [3]
  - If YES, the person either acted on these urges or was markedly distressed by them ........................................ [1] [2] [3]
- TRANSVESTIC FETISHISM - For a period of 6 months or more, there have been recurrent intense sexual urges and fantasies, in a heterosexual man, involving cross-dressing ........................................ [1] [2] [3]
  - If YES, the person either acted on these urges or was markedly distressed by them ........................................ [1] [2] [3]
- VOYEURISM - For a period of 6 months or more, there have been recurrent intense sexual urges and fantasies involving the observing of unsuspecting naked or disrobing persons, or people engaged in sexual activity ........................................ [1] [2] [3]
  - If YES, the person either acted on these urges or was markedly distressed by them ........................................ [1] [2] [3]
- OTHER PARAPHILIAS
  - Telephone scatologia (Lewdness) ........................................ [1] [2] [3]
  - Necrophilia (sex with corpses) ........................................ [1] [2] [3]
  - Partialism (exclusive focus on part of body) ........................................ [1] [2] [3]
  - Zoophilia (sex with animals) ........................................ [1] [2] [3]
  - Coprophilia (use of feces) ........................................ [1] [2] [3]
  - Klismaphilia (use of Enemas) ........................................ [1] [2] [3]
  - Urophilia (use of urine) ........................................ [1] [2] [3]

Sexual Dysfunctions

Sexual Desire / Aversion Disorders

- HYPOACTIVE SEXUAL DESIRE DISORDER - Lack of sexual desire/drive (taking age into account) ........................................ [1] [2] [3]
- SEXUAL AVERSION DISORDER - Aversion to and/or Avoidance of sexual contact ........................................ [1] [2] [3]

Sexual Arousal Disorders

- FEMALE SEXUAL AROUSAL DISORDER ........................................ [1] [2] [3]
- MALE ERECTILE DISORDER ........................................ [1] [2] [3]

Orgasm Disorders

- INHIBITED FEMALE ORGASM ........................................ [1] [2] [3]
- INHIBITED MALE ORGASM ........................................ [1] [2] [3]
- PREMATURE EJACULATION ........................................ [1] [2] [3]

Sexual Pain Disorders

- DYSPAREUNIA - Genital pain, recurrent or persistent, before, during, or after sexual intercourse in either a male or female (not due exclusively to the lack of lubrication or Vaginismus) ........................................ [1] [2] [3]
- VAGINISMUS - Involuntary spasm of the musculature of the outer third of the vagina, that is recurrent or persistent, and that interferes with coitus; not due to a physical disorder ........................................ [1] [2] [3]

| 1 = Moderately Severe or Often occurs | 2 = Severe or Usually occurs | 3 = Very Severe or Almost Always occurs |
|---|---|---|

Disorders of Activity/Energy Level and Behavioral Repetition

Overactivity / Exaggerated Energy Level:
- PSYCHOMOTOR AGITATION or TENSION - Trembling, shaky; tense, or rigid posture; easily startled ............................... [1] [2] [3]
- RESTLESS or IMPATIENT ............................................................................................................. [1] [2] [3]
- RECKLESS or IMPULSIVE ............................................................................................................ [1] [2] [3]
- TICS (Spasmodic movement occurring involuntarily) ............................................................................... [1] [2] [3]

Compulsions
The impulse to perform an act that the person identifies as meaningless, but which produces anxiety if resisted; may be a repetitive behavior performed in response to an obsession or performed according to a specific set of rules; the behavior has no real function except possibly to prevent something from happening in the future:
- Excessive or ritualized washing and grooming one's body ........................................................................... [1] [2] [3]
- REPETITION RITUALS - Repeated performance of various useless physical acts ....................................................... [1] [2] [3]
- Excessive CHECKING of doors, locks, appliances, automobile brakes, etc. ........................................................... [1] [2] [3]
- Excessive or ritualized CLEANING or ORGANIZING .................................................................................... [1] [2] [3]
- COUNTING .......................................................................................................................... [1] [2] [3]
- HOARDING and COLLECTING ........................................................................................................... [1] [2] [3]
- ACTIONS performed to PREVENT HARM to self or others ............................................................................... [1] [2] [3]
- Compulsive stealing (Kleptomania) ................................................................................................. [1] [2] [3]
- Compulsive sexual activity (Nymphomania/Satyriasis) ............................................................................... [1] [2] [3]
- Compulsive GAMBLING ............................................................................................................... [1] [2] [3]
- Compulsive FIRE SETTING (Pyromania) - Other than fire-setting for malicious or profit motives ..................................... [1] [2] [3]
- Compulsive pulling out OF one's hair (Trichotillomania) ........................................................................... [1] [2] [3]
- > The person RECOGNIZES that the behaviors above are EXCESSIVE or UNREASONABLE .................................................... [1] [2] [3]
- If CHILD: Intentional repetition of nonfunctional behaviors causes physical injury or prevents engagement in normal activities ........... [1] [2] [3]

Underactivity / Inhibited Energy Level; Low Sex Drive/Desire
- PSYCHOMOTOR RETARDATION - Slow motor and cognitive activity ....................................................................... [1] [2] [3]
- LETHARGY - Low energy level ....................................................................................................... [1] [2] [3]

Odd, Bizarre, or Disorganized Psychomotor Behaviors:
- ECHOPRAXIA - Automatic, pathological copying and repetition of another's movements ................................................ [1] [2] [3]
- CATATONIA - Non-organic motor anomalies, including the signs below: .............................................................. [1] [2] [3]
  - Catalepsy - remains immobile for long periods of time in any fixed position
  - Catatonic Excitement - period excessive motor activity and restlessness unrelated to external stimuli
  - Catatonic Stupor - immobility and inaccessibility to external stimuli
  - Catatonic Rigidity - voluntary maintenance of extremely rigid posture resisting attempts to be moved
  - Catatonic Posturing - extended period of time during which a voluntary odd or bizarre posture is maintained
  - Waxy Flexibility - the person's limbs can be moved into any position which is then maintained; limbs feel wax-like
  - NEGATIVISM - Motiveless and persistent resistance to the requests of others or to attempts at being moved
- GROSSLY DISORGANIZED BEHAVIOR - Including the following: ......................................................................... [1] [2] [3]
  - CATAPLEXY - Emotionally precipitated temporary loss of muscle tone resulting in body collapse
  - STEREOTYPY - Persistent pathological repetition of a fixed pattern of movement or speech
  - MANNERISMS - Ingrained and habitual gesture, facial or verbal expression occurring involuntarily
  - AUTOMATISM - An activity that is performed automatically, without intention or awareness
  - MUTISM - Voicelessness despite an intact vocal system
- TALKS to SELF (does not include normal self-talk in children) ..................................................................... [1] [2] [3]

1 = Moderately Severe or Often occurs    2 = Severe or Usually occurs    3 = Very Severe or Almost Always occurs

Passive / Dependent / Avoidant Behavior

- INSECURE / CONSTANTLY SEEKS REASSURANCE ... [1] [2] [3]
- DEPENDENT / CONSTANTLY SEEKS ASSISTANCE ... [1] [2] [3]
- CONSTANTLY SEEKS ATTENTION or ADMIRATION ... [1] [2] [3]
- PASSIVITY / UNASSERTIVENESS ... [1] [2] [3]
- AVOIDANCE of PEOPLE / WITHDRAWN WANTS to be with PEOPLE, but withdraws (is isolated) due to FEAR of REJECTION or HARM [1] [2] [3]
  - Does NOT WANT or ENJOY being with people; prefers ISOLATION ... [1] [2] [3]
  - If CHILD: Lack of adequate peer relationships due to avoidance of unfamiliar people ... [1] [2] [3]

Aggressive, Hurtful, Cruel, and Exploitive Behavior

- Frequent LYING (other than to avoid being abused) ... [1] [2] [3]
- Frequently EXPLOITIVE / MANIPULATIVE - Takes advantage of others for own ends ... [1] [2] [3]
- Frequently BLAMES OTHERS for ONE'S OWN MISTAKES or WRONGDOINGS ... [1] [2] [3]
- Frequently SPITEFUL or VINDICTIVE ... [1] [2] [3]
- Often DEFIES, UNREASONABLY CRITICIZES, or SCORNS AUTHORITY ... [1] [2] [3]
- Often CRUEL, OFFENSIVE, or ANNOYING TOWARD OTHER PEOPLE ... [1] [2] [3]
- Often uses obscene language ... [1] [2] [3]
- Often INITIATES PHYSICAL FIGHTS (including spouse- and child-beating) ... [1] [2] [3]
- Has USED A WEAPON WHILE FIGHTING - Indicate approx. frequency ... [1] [2] [3] [4+]
- Has FORCED OTHERS INTO SEXUAL ACTIVITY (including rape) - Indicate approx. frequency ... [1] [2] [3] [4+]
- NON-confrontationAL THEFT (including forgery) - Indicate approx. frequency ... [1] [2] [3] [4+]
- confrontational THEFT (including mugging, armed robbery, and extortion) - Frequency ... [1] [2] [3] [4+]
- BREAKING AND ENTRY (into homes, buildings, or cars - Indicate approx. frequency ... [1] [2] [3] [4+]
- DELIBERATE DESTRUCTION of OTHER'S PROPERTY (other than by fire-setting) - Frequency ... [1] [2] [3] [4+]
- Deliberate FIRE-SETTING (other than Compulsive Pyromania) - Indicate approx. frequency ... [1] [2] [3] [4+]
- ANIMAL CRUELTY - Indicate approx. frequency ... [1] [2] [3] [4+]

Irresponsible and other Maladaptive Behaviors

- RAN AWAY FROM HOME of parent /guardian (except to avoid abusive treatment) - Indicate approx. frequency (NR=Never Returned) ... [1] [2] [3+] [NR]
- Lack of consistent work (including school) behavior as evidenced by any of the following: ... [1] [2] [3]
  - Unemployed for 6 months or more in five years although work is available
  - Frequent absences from work (or truancy from school) not due to illness or legitimate emergency
  - Quitting several jobs (or dropping out of school) without realistic future plans
- FINANCIALLY IRRESPONSIBLE - repeatedly defaults on debts ... [1] [2] [3]
- Pattern of UNSTABLE or POOR INTERPERSONAL RELATIONSHIPS ... [1] [2] [3]
- If a parent or guardian: fails to function as a responsibly as evidenced by one or more of the following: ... [1] [2] [3]
  - Allows one's children to be malnourished
  - Fails to provide minimal hygiene results in child's illness
  - Fails to take seriously ill child for appropriate medical care
  - Relies on others to provide basic child nuturance (other than child care assistance while working)
  - Fails to arrange for adequate child care when parents are away from the home
  - Repeatedly squanders necessary family monies on items for one's personal pleasure
- PROCRASTINATES, FAILS to MAKE DECISIONS, or AVOIDS ONE'S RESPONSIBILITIES ... [1] [2] [3]
- PERFECTIONISM - Failure to complete tasks in a timely manner due to overconcern that self-imposed excessively high standards are not being met ... [1] [2] [3]
- WORKAHOLISM - Excessive engagement in work-related activities has caused other life-problems ... [1] [2] [3]

| 1 = Moderately Severe or Often occurs | 2 = Severe or Usually occurs | 3 = Very Severe or Almost Always occurs |

Disturbances of Conscious State of Awareness

Disturbance of Consciousness:
o DISORIENTATION in Time, Place, or Person ... [1] [2] [3]
o CLOUDING OF CONSCIOUSNESS - Person is in a "Mental Fog" with serious impairment in sensory perceptual, and thought processes .... [1] [2] [3]
o STUPOR - (Almost) total unresponsiveness or awareness to the surrounding environment ... [1] [2] [3]
o DELIRIUM - A state of restless, confused disorientation in which the environment is misperceived and hallucinations occur ... [1] [2] [3]
o TWILIGHT STATE- Temporary unawareness of surroundings with fleeting hallucinations ... [1] [2] [3]
o SOMNOLENCE - Pathological drowsiness or sleepiness ... [1] [2] [3]

Disturbance of Attention/Concentration:
o Poor Concentration due to DISTRACTIBILITY - Attention is easily drawn to extraneous external stimuli ... [1] [2] [3]
o Poor Concentration due to PREOCCUPATION with SUBJECTIVE INTERNAL EXPERIENCES - Attention is drawn to the person's own subjective emotional or cognitive activity ... [1] [2] [3]
o Poor Concentration due to LACK of MENTAL ENERGY ... [1] [2] [3]
o SELECTIVE ATTENTION ... [1] [2] [3]
o HYPERVIGILANCE ... [1] [2] [3]
o PERSEVERATION - Failure to shift attention to new external stimuli ... [1] [2] [3]

Problems with Self-Esteem, Self-Identity, Self-Image (from part C)

{NOTE: If DELUSIONAL, see Delusions on page 7}

Self-Esteem
o GRANDIOSE / INFLATED SELF-ESTEEM / SENSE OF ENTITLEMENT - Overestimates one's importance, power, accomplishments, etc.; sees self as deserving of or entitled to special treatment ... [1] [2] [3]
o LOW SELF-ESTEEM / DEFLATED SELF-WORTH - Diminishes one's human value ... [1] [2] [3]
o Sense that one is DIFFERENT than others, or ESTRANGED or DETACHED from others ... [1] [2] [3]

Self-Identity
o IDENTITY Problems - The person experiences severe emotional distress concern regarding:
  * long-term goals or choices of career ... [1] [2] [3]
  * friendship patterns or type of desired friendships ... [1] [2] [3]
  * sexual orientation, sexual behavior, and/or gender-identification ... [1] [2] [3]
  * religious identification ... [1] [2] [3]
  * moral and other preferred values ... [1] [2] [3]

Self-Image
o Despite normal physical appearance, the person is preoccupied with an imagined or grossly exaggerated defect in appearance ... [1] [2] [3]
  * If YES, can the person acknowledge that his/her perception of appraisal of the defect is exaggerated (i.e., it is NON-DELUSIONAL) ... [1] [2] [3]

1 = Moderately Severe or Often occurs     2 = Severe or Usually occurs     3 = Very Severe or Almost Always occurs

Disturbances of Affect / Mood / Emotion

Inappropriate Affect / Mood / Emotion:
o  An emotional feeling that is not consistent with the accompanying thoughts or situation ............................................. [1] [2] [3]

Unstable Affect / Mood / Emotion:
o  Labile Affect (mood swings) - The feeling tone changes rapidly, abruptly and independently
   of external stimuli; periodic alternation between feelings of euphoria and dysphoria ..................................... [1] [2] [3]

Abnormally LOW-intensity Affect / Mood / Emotion:
o  BLUNTED affect - The feeling tone is severely dulled in intensity .................................................................... [1] [2] [3]
o  RESTRICTED/CONSTRICTED affect- Feeling tone is reduced, but not as severe as blunted affect ......................... [1] [2] [3]
o  FLAT affect - Absence or near absence of emotional expression in all situations ............................................... [1] [2] [3]
o  APATHY - A dulled emotional tone associated with indifference to one's surroundings
   • ANHEDONIA - The person loses interest in and withdraws from all pleasurable activities ........................... [1] [2] [3]
   • LACK of EMPATHY FOR or CONCERN ABOUT OTHERS ............................................................... [1] [2] [3]
   • Does NOT CARE what others think about him/her; INDIFFERENT to praise or criticism ......................... [1] [2] [3]
   • RESTRICTED EXPRESSION of AFFECTION ..................................................................................... [1] [2] [3]
o  LACK of REMORSE - Feeling justified in hurting others ................................................................................ [1] [2] [3]
o  AMBIVALENCE - Mixed, contradictory emotions occurring simultaneously ........................................................ [1] [2] [3]
o  ALEXITHYMIA - The person is unaware of or unable to describe one's own emotions .................................. [1] [2] [3]

Abnormally HIGH-intensity Affect / Mood / Emotion:

Positive
o  EXPANSIVE - Unrestrained expression of one's emotions, often with the exaggeration of self-importance ............................. [1] [2] [3]
o  EUPHORIA - Intense, elated feelings of boundless strength, happiness, and optimism ................................................ [1] [2] [3]
o  ECSTASY - A feeling of extreme euphoric pleasure or rapture ......................................................................... [1] [2] [3]

Negative
o  DYSPHORIC mood - A mood that is unpleasant ................................................................................................ [1] [2] [3]
o  IRRITABLE mood (including LOW FRUSTRATION TOLERANCE) - The person becomes
   annoyed or angered easily .............................................................................................................................. [1] [2] [3]
o  OVERLY SENSITIVE, SELF-CONSCIOUS, EASILY HURT or SLIGHTED by criticism /disapproval ................................. [1] [2] [3]
o  ANXIETY/FEAR - Apprehension related to a perceived danger with the goal of avoiding the threat ..................................... [1] [2] [3]
   • Great FEAR of real or imagined ABANDONMENT ............................................................................... [1] [2] [3]
o  PANIC Attack - Unexpected feelings of panic not triggered by being the focus of the attention of others ................................ [1] [2] [3]
o  FREE-FLOATING ANXIETY - Pervasive fear that is not associated with a recognizable threat .......................................... [1] [2] [3]
o  ANGER/RESENTMENT - A response to frustration or threat (including ego-threat with the goal of
   removing or destroying the source of the threat ............................................................................................. [1] [2] [3]
o  DEPRESSION - Pathological sadness .......................................................................................................... [1] [2] [3]
   • History of depression which has been helped by prescription medication or ECT ............................................. [1] [2] [3]
o  Feels extremely DISTRAUGHT or HELPLESS when ALONE or when a RELATIONSHIP ENDS .......................... [1] [2] [3]
o  Extreme PESSIMISM ABOUT ONE'S FUTURE ............................................................................................. [1] [2] [3]
o  GRIEF or MOURNING - Appropriate sadness related to a real loss ................................................................. [1] [2] [3]
o  GUILT (Pathological) - Exaggerated reaction to real or imagined transgression .................................................. [1] [2] [3]
o  SHAME (Pathological) - Painful feeling of humiliation, self-disgrace, or extreme embarrassment ......................... [1] [2] [3]
o  JEALOUSY (Pathological) - A rival is believed to be threatening the person's relationship with another ................. [1] [2] [3]
o  ENVY (Malicious) - Desire to see harm befall someone perceived to be enjoying a superior situation ..................... [1] [2] [3]

| 1 = Moderately Severe or Often occurs | 2 = Severe or Usually occurs | 3 = Very Severe or Almost Always occurs |
|---|---|---|

Disturbances of THINKING

Thought Process/Form

Goal Is Reached
- CIRCUMSTANTIALITY - Digressive, indirect speech that eventually reaches the desired goal, but in which thinking is frequently sidetracked by inclusion of irrelevant details and parenthetical remarks ................................. [1] [2] [3]

Goal Is Not Reached
- TANGENTIALITY - Person fails to reach the desired goal despite goal-directed association of thought ................................. [1] [2] [3]
- NEOLOGISM - New, idiosyncratic, nonsense word often formed by combining syllable of other words ................................. [1] [2] [3]
- NON SEQUITUR - A totally unrelated response to a question ................................. [1] [2] [3]
- FRAGMENTATION - A continuous flow of non sequiturs ................................. [1] [2] [3]
- RAMBLING - Groups of closely connected sentences followed by other sentence groups lacking connection or goal ................................. [1] [2] [3]
- DRIVELING - Syntax and sentence linkage appear maintained, but neologisms and lack of goal-directness make the speech impossible to understand ................................. [1] [2] [3]
- PERSEVERATION - A word, phrase, or theme is repeated despite changes in the conversation topic ................................. [1] [2] [3]
- VERBIGERATION - Words or phrases are automatically repeated, especially at the ends of sentences ................................. [1] [2] [3]
- ECHOLALIA - Persistent repeating of words or phrases spoken by another person ................................. [1] [2] [3]
- LOOSENING of ASSOCIATIONS or DERAILMENT - The stream of thought is interrupted, but then resumes with an entirely new thought; the flow of thought is shifted from one subject to another unrelated subject ................................. [1] [2] [3]
- FLIGHT OF IDEAS - Non-goal-oriented speech in which ideas constantly switch from one to another; there is a connection between adjacent ideas, but new trains of thought are triggered by a word spoken in the previous sentence; may be subjectively experienced as RACING THOUGHTS ................................. [1] [2] [3]
- CLANG ASSOCIATION - Similarly sounding words are associated such as in rhyming and punning, there is no logical or meaningful connection between the spoken words ................................. [1] [2] [3]
- BLOCKING - The train of thought is suddenly interrupted with no recall in what was said ................................. [1] [2] [3]
- WORD SALAD (JARGON APHASIA) - Incomprehensible speech formed by a incoherent mixture of unrelated neologisms, words, and phrases ................................. [1] [2] [3]

> Other
- DOGMATIC, INFLEXIBLE beliefs or opinions; RIGID, SINGLE-MINDED style of thinking ................................. [1] [2] [3]
- Tendency to EXAGGERATE the LIKELIHOOD or ADVERSE EFFECT of occurrences; "BLOWS THINGS UP" OUT of PROPORTION ... [1] [2] [3]

| 1 = Moderately Severe or Often occurs | 2 = Severe or Usually occurs | 3 = Very Severe or Almost Always occurs |

Content of Thought o POVERTY OF CONTENT of THOUGHT/SPEECH (IMPOVERISHED SPEECH) - Vague, empty,
   or obscure speech comprised of phrases or repetitions that fail to convey meaningful information ............................................ [1] [2] [3]
o OVERVALUED IDEAS / Odd or magical thinking - False, unreasonable beliefs that are strongly maintained and are inconsistent
   with subcultural norms, but are not of delusional quality or intensity (e.g., superstitiousness, belief in telepathy, clairvoyance, or
   having a "sixth sense;") .......................................................................................................................................... [1] [2] [3]
o BIZARRE FANTASIES or PREOCCUPATIONS in CHILDREN & ADOLESCENTS ............................................................... [1] [2] [3]
o Preoccupation with ORGANIZATION, ORDER, RULES, DETAILS, etc. is focus of activity ............................................. [1] [2] [3]

Delusions
False beliefs, inconsistent with external reality, that is rigidly maintained

*with DEPRESSIVE Themes*
- NIHILISM and DEATH ...................................................................................................................................... [1] [2] [3]
- ILLNESS ......................................................................................................................................................... [1] [2] [3]
- POVERTY ....................................................................................................................................................... [1] [2] [3]
- GUILT - Self-accusation .................................................................................................................................. [1] [2] [3]

*GRANDIOSE Delusions*
- MESSIANIC ABILITIES .................................................................................................................................... [1] [2] [3]
- WEALTH ......................................................................................................................................................... [1] [2] [3]
- INDESTRUCTIBILITY ...................................................................................................................................... [1] [2] [3]
- POWER and GIFTEDNESS ............................................................................................................................... [1] [2] [3]
- MARTYRDOM ................................................................................................................................................ [1] [2] [3]

*PARANOID Delusions*
- Delusion of PERSECUTION - The belief that one is being persecuted, cheated, or harassed
  - PERSECUTORS are JEALOUS of the person ................................................................................................ [1] [2] [3]
  - The person is being PUNISHED for MORAL FAILURE or SIN ....................................................................... [1] [2] [3]
  - PERSECUTORS have MISUNDERSTOOD the persons GOOD INTENTIONS .................................................. [1] [2] [3]
  - The person CANNOT FIGURE OUT the REASON for the persecution ........................................................... [1] [2] [3]
- Delusion of REFERENCE - The belief that the behaviors of others are referring to oneself or that
  various external events have some special relationship to oneself or unusual personal significance ..................... [1] [2] [3]

*Delusion of CONTROL*
- THOUGHT WITHDRAWAL - Outside forces or people are stealing one's thoughts ............................................... [1] [2] [3]
- THOUGHT INSERTION - Outside forces or people are implanting their thoughts into one's mind ......................... [1] [2] [3]
- THOUGHT BROADCASTING - One's thoughts can be heard by others as though they were broadcasted through the air ............... [1] [2] [3]
- THOUGHT, WILL, or FEELING INSERTION CONTROL - Outside forces people are controlling one's thoughts, behaviors, or feelings . [1] [2] [3]

*ROMANTIC Delusions*
- Delusion of INFIDELITY (Delusional Jealousy) - False belief that one's partner is unfaithful ......................................... [1] [2] [3]
- EROTOMANIA - False belief that someone is deeply in love with oneself ...................................................... [1] [2] [3]

Other
- Did the person's delusion develops (in a second person) in the context as a result of a close
  relationship with another person or persons who already has an established delusion? ............................................. [1] [2] [3]

Hypochondria
Exaggerated concern about one's physical health due to an unrealistic interpretation of bodily signs or sensations as being abnormal ........... [1] [2] [3]

Obsessions
Thoughts that the person identifies as useless and unacceptable, but which persist despite the person's attempts to stop them; they include thought about:
- BECOMING CONTAMINATED ........................................................................................................................ [1] [2] [3]
- HAVING FORGOTTEN SOMETHING .............................................................................................................. [1] [2] [3]
- HURTING or KILLING OTHERS ..................................................................................................................... [1] [2] [3]
- IMAGES of TRAUMATIC EVENTS ................................................................................................................. [1] [2] [3]
- PHILOSOPHICAL RUMINATIONS .................................................................................................................. [1] [2] [3]

| 1 = Moderately Severe or Often occurs | 2 = Severe or Usually occurs | 3 = Very Severe or Almost Always occurs |

Coprolalia
An uncontrollable impulse to utter obscene words or make obscene expressions ................................................... [1] [2] [3]

Trauma-Induced Stress Reactions
- RE-EXPERIENCING the TRAUMA - in dreams, recurrent distressing recollections, sense of re-living the trauma ................... [1] [2] [3]
- AVOIDANCE of THOUGHTS, FEELINGS, or MEMORIES CONNECTED TO or SITUATIONS that RESEMBLE the TRAUMA ...... [1] [2] [3]

Phobias
Excessive, unrealistic, persistent, irrational fear of particular objects or situations that result in strong avoidance behaviors; some of the more typical phobias include the following:
- SIMPLE Phobia - dread of a specific, discrete object or situation, such as dogs, spiders, snakes, etc. ................................. [1] [2] [3]
  - ACROPHOBIA - dread of high places ............................................................................ [1] [2] [3]
  - AGORAPHOBIA - dread of being in public places where escape may be difficult ............................................. [1] [2] [3]
  - ALGOPHOBIA - dread of pain .................................................................................. [1] [2] [3]
  - CLAUSTROPHOBIA - dread of closed in places ................................................................... [1] [2] [3]
  - XENOPHOBIA - dread of strangers .............................................................................. [1] [2] [3]
  - ZOOPHOBIA - dread of animals ................................................................................. [1] [2] [3]
- SOCIAL Phobia - dread of being humiliated or embarrassed in public ............................................................ [1] [2] [3]
- Occupational functioning and/or with social functioning is impaired by the fear, or the person experiences great distress about being afraid [1] [2] [3]

Disturbances of Speech

Disturbances in Speech Style or Production:
- PRESSURE of speech - Rapid speech that is difficult to interrupt ................................................................. [1] [2] [3]
- VOLUBILITY (LOGORRHEA) - Excessive, uncontrollable speech that is logical and coherent ......................................... [1] [2] [3]
- POVERTY of speech (also see: POVERTY of CONTENT of THOUGHT/SPEECH) - Speech that is excessively brief and unelaborated ..... [1] [2] [3]
- NONSPONTANEOUS speech - Speech is not self-initiated; person responds only when spoken to first ................................. [1] [2] [3]
- DYSPROSODY - Disruption of normal speech melody .............................................................................. [1] [2] [3]
- DYSARTHRIA - Articulation difficulty ........................................................................................... [1] [2] [3]
- VOLUME abnormality- Speech is excessively loud or soft ....................................................................... [1] [2] [3]
- STUTTERING - Speech fluency impaired by frequent repetition or prolongation of sounds or syllables .............................. [1] [2] [3]
- CLUTTERING - Jumbled and imprecise speech is produced in rapid and jerky spurts ............................................... [1] [2] [3]
- Speech style is excessively impressionistic and without detail ................................................................. [1] [2] [3]

Disturbances in Language Output (Aphasia):
- MOTOR (EXPRESSIVE) aphasia - Organically caused gross impairment in one's ability to speak, but
  the person's ability to understand language is normal ........................................................................ [1] [2] [3]
- SENSORY (RECEPTIVE) aphasia - Organically caused gross impairment in one's ability to understand
  the meaning of words; the person is unable to speak coherently or sensibly' ................................................... [1] [2] [3]
- NOMINAL aphasia (ANOMIA) - Difficulty recalling the name of objects ........................................................ [1] [2] [3]
- SYNTACTICAL aphasia - Unable to arrange words in the proper syntactic sequence ............................................. [1] [2] [3]
- ELECTIVE MUTISM - Able to speak, but refuses to do so ...................................................................... [1] [2] [3]

1 = Moderately Severe or Often occurs 2 = Severe or Usually occurs 3 = Very Severe or Almost Always occurs

Perception

ILLUSION:
A false sensory perception or interpretation of stimuli existing in the environment ............ [1] [2] [3]

HALLUCINATIONS:
A false sensory perception in which non-existing stimuli are perceived as real
- AUDITORY hallucination - False perception involving sound ............ [1] [2] [3]
- VISUAL hallucination - False perception involving sight ............ [1] [2] [3]
- OLFACTORY hallucination - False perception involving smell ............ [1] [2] [3]
- GUSTATORY hallucination - False perception involving taste ............ [1] [2] [3]
- TACTILE (HAPTIC) hallucination - False perception involving touch or surface sensation ............ [1] [2] [3]
- SOMATIC hallucination - False perception involving sensation of occurrences in or on the body ............ [1] [2] [3]
- LILLIPUTIAN hallucination False perception in which objects are seen as smaller than actual size ............ [1] [2] [3]
- HALLUCINOSIS - Hallucinations associated with chronic alcohol abuse ............ [1] [2] [3]

Organically Induced Perceptual Disturbances:
- ANOSOGNOSIA - Failure to recognize a defect or disease as occurring to oneself ............ [1] [2] [3]
- AUTOTOPAGNOSIA - Failure to recognize a body part as belonging to oneself ............ [1] [2] [3]
- VISUAL AGNOSIA - Failure to recognize common objects or persons ............ [1] [2] [3]
- ASTEREOGNOSIA - Failure to recognize objects by touch ............ [1] [2] [3]
- PROSOPAGNOSIA - Inability to recognize faces ............ [1] [2] [3]
- APRAXIA - Inability to perform purposeful movement and tasks ............ [1] [2] [3]

Conversion and Dissociative Disturbances:
- HYSTERICAL ANESTHESIA - Sensory modality are lost as a consequence of emotional conflicts:
- DEAFNESS ............ [1] [2] [3]
- BLINDNESS ............ [1] [2] [3]
- TUNNEL VISION ............ [1] [2] [3]
- MACROPSIA - Objects appear larger than they are ............ [1] [2] [3]
- MICROPSIA - Objects appear smaller than they are ............ [1] [2] [3]
- DEPERSONALIZATION - A state of mind in which the self seems unreal, strange, or unfamiliar ............ [1] [2] [3]
- DEREALIZATION - A state of mind in which one's environment seems unreal or strange ............ [1] [2] [3]
- FUGUE - Amnesic state in which one forgets the past (possibly relocates) & takes on a new identity ............ [1] [2] [3]
- MULTIPLE PERSONALITY - Two or more distinct personalities exist within the individual and appear at different times ............ [1] [2] [3]

1 = Moderately Severe or Often occurs    2 = Severe or Usually occurs    3 = Very Severe or Almost Always occurs

Memory Problems

- AMNESIA - Inability to recall important personal information or experiences from the past; may be partial or complete, organic or emotionally caused ............................................................................. [1] [2] [3]
- Short-term memory impairment - Failure to remember three objects after five minutes ................................................ [1] [2] [3]
- Long-term memory impairment - Failure to remember past personal information (what happened yesterday, birthplace, occupation) or facts of common knowledge (e.g., past Presidents, well-known dates) .................................................................. [1] [2] [3]
- PARAMNESIA - Memory is falsified or distorted ................................................................................ [1] [2] [3]
- EIDETIC IMAGE - A memory image of extremely vivid detail ................................................................... [1] [2] [3]

Specific Learning Disabilities

- DYSLEXIA ............................................................................................................................ [1] [2] [3]
- DYSCALCULIA ...................................................................................................................... [1] [2] [3]
- RECEPTIVE LANGUAGE Impairment ................................................................................................ [1] [2] [3]

Intellectual Deficiencies

- MENTAL RETARDATION - IQ below 70 ............................................................................................ [1] [2] [3]
- DEMENTIA - Global deterioration of intellectual functioning due to organic causes, but without clouding of consciousness ................ [1] [2] [3]
  - Insidious onset and progressive deterioration ................................................................................ [1] [2] [3]
- PSUEDODEMENTIA - Global deterioration of intellectual functioning NOT due to organic causes, a symptom of depression ............. [1] [2] [3]
- Abstract thinking impairment - Inability to understand the nuances of meaning, understand metaphor, or appropriate use hypotheses; concrete, literal thinking ............................................................................................................. [1] [2] [3]

Problems with Insight and Judgement

IMPAIRED Insight - Inability (or diminished ability) to understand the true, objective cause and meaning of a situation; shows poor discretion ......................................................................................... [1] [2] [3]
IMPAIRED SOCIAL Judgment - Inability to understand and plan how to deal with social and job-related problems and issues in a reasonable and appropriate manner ................................................................ [1] [2] [3]

Other

- If a CHILD: Frequent complaints of physical symptoms (e.g., headaches, stomachache distress) on many school days or on other occasions when anticipating separation from major attachment figures ......................................... [1] [2] [3]
- {Ask} 'What are your life goals?'
  - Do they indicate a lack of initiative, motivation, or interest in one's future? ...................................................... [1] [2] [3]
- Significant cerebrovascular disease etiologically related to the disturbance ........................................................... [1] [2] [3]
- Constructional difficulty (e.g., inability to copy three-dimensional figures, assemble blocks, or arrange sticks in specific designs)
- FOCAL NEUROLOGICAL SIGNS and SYMPTOMS - Exaggeration of deep tendon reflexes, extensor plantar response, pseudobulbar palsy, gait abnormalities, weakness of an extremity, etc." (DSMIII-R) .................................. [1] [2] [3]

INFORMATION ABOUT YOUR PAST

The following pages examine your early relationships with people in your family and people not in your family. On the left side of the page are statements numbered { 1 }, { 2 }, { 3 }, or { 4 }. On the right side of the page are three columns labeled < A >, < B >, and < C > that contain the description of various people who may have been part of your past. As you read each statement, think about the people in your life when you were growing up for whom the statement was MOSTLY TRUE. Then, for each statement that fairly accurately describes a person in your past, mark an "X" in the corresponding boxes.

For example, if the statement is MOSTLY TRUE about:

o your mother or primary female caretaker (such a stepmother or foster mother), then mark the [1A] box;

o your father or primary male caretaker (such a stepfather or foster father), then mark the [1B] box;

o someone other than a parent or primary caretaker who affected your life (including grandparents, brothers, sisters, aunts, uncles, cousins, or non-family members such as teachers, friends, etc., then mark the [1C] box. You need not refer to the same person each time you answer a question.

Mark all the boxes that are mostly true. You may mark any or all of the boxes.

| Please answer the following about your relationships with others when you were growing up. Mark the boxes that are MOSTLY TRUE. You may mark any or all of the boxes in whatever combination you choose. | < A > my Mother or Female Caretaker | < B > my Father or Male Caretaker | < C > Another Person who affected my life |
|---|---|---|---|

1. The amount of ACCEPTANCE, RESPECT, and APPROVAL I received from this person:

{ 1 } *TOO LITTLE* ............................................................. [1A]   [1B]   [1C]
    This person either:
    · CRITICIZED, RIDICULED or REJECTED me too much ;
    · made me feel like I was usually DISAPPOINTING him/her;
    · made me feel that I was NEVER GOOD ENOUGH.

{ 2 } *TOO MUCH* ............................................................. [2A]   [2B]   [2C]
    This person either:
    · SPOILED ME;
    · made me feel SO SPECIAL that I felt I DESERVED ONLY THE BEST;
    · made me feel that things SHOULD ALWAYS BE MY WAY or that I MUST GET WHATEVER I WANTED;
    · told me that I was GREAT even when I knew it was NOT TRUE.

{ 3 } *INCONSISTENT* ............................................................. [3A]   [3B]   [3C]
    This person either:
    · gave me ACCEPTANCE, RESPECT, or APPROVAL *ONLY* if I LIVED UP TO his/her EXPECTATIONS or if I SUCCEEDED in the things he/she wanted me to do;
    · REJECTED, RIDICULED, or TREATED ME POORLY if I DISAPPOINTED him/her or if I FAILED to do well at certain things { 4 } *A GOOD AMOUNT* ............................................................. [4A]   [4B]   [4C]
    This person either:
    · gave me LOVE, ACCEPTANCE, or RESPECT was shown to me by this person ALL THE TIME;
    · made me feel like I was SPECIAL and IMPORTANT to him/her even when I didn't do things well.

Appendix E

|   | \<A\> my Mother or Female Caretaker | \<B\> my Father or Male Caretaker | \<C\> Another Person who affected my life |
|---|---|---|---|

*Please answer the following about your relationships with others when you were growing up.*

2. The amount of AFFECTION I received from this person:

{ 1 } *TOO LITTLE* ............................................................. [ 1A ]  [ 1B ]  [ 1C ]

This person was usually:
  - *NOT* physically or verbally AFFECTIONATE;
  - usually COLD, ALOOF, SHY, or UNCOMFORTABLE with affection { 2 } *TOO MUCH* ............................................................. [ 2A ]  [ 2B ]  [ 2C ]

This person was usually *OVERLY* or *INAPPROPRIATELY* AFFECTIONATE with me (such as being SEDUCTIVE)

{ 3 } *A GOOD AMOUNT* ....................................................... [ 3A ]  [ 3B ]  [ 3C ]

This person was usually *APPROPRIATELY* AFFECTIONATE with me; I felt a HEALTHY

---

3. The amount of ENCOURAGEMENT, SUPPORT, and INSPIRATION I received from this person:

{ 1 } *TOO LITTLE* ............................................................. [ 1A ]  [ 1B ]  [ 1C ]

This person usually either:
  - DISCOURAGED, BLOCKED, or INHIBITED me;
  - made me feel HOPELESS or made me believe that I could NEVER AMOUNT TO ANYTHING { 2 } *TOO MUCH* ............................................................. [ 2A ]  [ 2B ]  [ 2C ]

This person usually either:
  - ENCOURAGED me TO DO *TOO MUCH*;
  - PUSHED to do things that were *TOO* DIFFICULT for me
  - made me feel either FRUSTRATED, STRESSED-OUT or like a FAILURE { 3 } *A GOOD AMOUNT* ....................................................... [ 3A ]  [ 3B ]  [ 3C ]

This person usually ENCOURAGED, SUPPORTED, MOTIVATED or INSPIRED me in a *GOOD WAY*

---

4. Type of GUIDANCE and DISCIPLINE I received from this person:

{ 1 } *TOO LITTLE* ............................................................. [ 1A ]  [ 1B ]  [ 1C ]

This person was either:
  - *TOO* LENIENT, TRUSTING, or PERMISSIVE with me;
  - allowed me to GET AWAY WITH *TOO* MUCH bad behavior or laziness { 2 } *TOO MUCH* ............................................................. [ 2A ]  [ 2B ]  [ 2C ]

This person was either:
  - *OVERLY* STRICT, INTRUSIVE, DOMINEERING, DISTRUSTING, OVERBEARING with me;
  - made me feel like I was BEING CONTROLLED { 3 } *INCONSISTENT* ......................................................... [ 3A ]  [ 3B ]  [ 3C ]

This person was very *INCONSISTENT* in the way he/she guided or disciplined me

{ 4 } *A GOOD AMOUNT* ....................................................... [ 4A ]  [ 4B ]  [ 4C ]

This person usually RESPECTED my RIGHTS and ENCOURAGED my INDEPENDENCE while his/her guidance and discipline HELPED ME MAKE GOOD DECISIONS

|  | <A><br>my<br>Mother<br>or Female<br>Caretaker | <B><br>my<br>Father<br>or Male<br>Caretaker | <C><br>Another<br>Person who<br>affected<br>my life |
|---|---|---|---|

*Please answer the following about your relationships with others when you were growing up.*

5. The amount that I could DEPEND UPON, TRUST, or FEEL SECURE with this person:

{ 1 } *TOO LITTLE* .................................................... [ 1A ]   [ 1B ]   [ 1C ]
    This person either:
    • could *NOT* BE DEPENDED UPON or TRUSTED;
    • DISHONEST, INSINCERE, or HYPOCRITICAL, or often ACTED in a FALSE (FAKE or PHONEY) WAY;
    • made me feel INSECURE because he/she often THREATENED TO ABANDON ME;

{ 2 } *TOO MUCH* ..................................................... [ 2A ]   [ 2B ]   [ 2C ]
    This person either:
    • was *OVERLY* HELPFUL, DID *TOO* MUCH for me, or was *OVER*-PROTECTIVE;
    • made me DEPENDENT ON him/her;
    • made me feel INSECURE or FEARFUL *WITHOUT* him/her { 3 } *INCONSISTENT* ................................................ [ 3A ]   [ 3B ]   [ 3C ]
    This person was so *INCONSISTENT* that I usually DIDN'T KNOW whether to trust or depend upon him/her { 4 } *A GOOD AMOUNT* ............................................. [ 4A ]   [ 4B ]   [ 4C ]
    This person was DEPENDABLE and TRUSTWORTHY in a *GOOD WAY* and made me FEEL SECURE 6. The amount of UNDERSTANDING and COMMUNICATION I had with this person:

{ 1 } *TOO LITTLE* .................................................... [ 1A ]   [ 1B ]   [ 1C ]
    This person:
    • NEVER REALLY UNDERSTOOD what I thought or what I felt;
    • could *NOT* COMMUNICATE well with me { 2 } *TOO MUCH* ..................................................... [ 2A ]   [ 2B ]   [ 2C ]
    This person:
    • UNDERSTOOD ME *TOO WELL*;
    • made me feel like I had NO MIND OF MY OWN { 3 } *A GOOD AMOUNT* ............................................. [ 3A ]   [ 3B ]   [ 3C ]
    This person really UNDERSTOOD ME in a *GOOD WAY*, we COMMUNICATED *WELL*

7. The amount of CARE, CONCERN, or EMPATHY shown by this person:

{ 1 } *TOO LITTLE* .................................................... [ 1A ]   [ 1B ]   [ 1C ]
    This person was usually either:
    • SELF-CENTERED, SELFISH, or was mostly interested in being the CENTER OF ATTENTION;
    • INSENSITIVE, UNSYMPATHETIC, IGNORED MY EMOTIONAL NEEDS, MADE ME FEEL UNWANTED;
    • a MANIPULATIVE USER who TOOK ADVANTAGE OF OTHERS { 2 } *TOO MUCH* ..................................................... [ 2A ]   [ 2B ]   [ 2C ]
    This person either:
    • was TOO INVOLVED in other people's lives;
    • often SUFFERED for OTHERS like a SELF-SACRIFICING MARTYR { 3 } *A GOOD AMOUNT* ............................................. [ 3A ]   [ 3B ]   [ 3C ]
    This person was UNSELFISH and DEVOTED to OTHERS in a PLEASANT and HEALTHY WAY

|  | <A><br>my<br>Mother<br>or Female<br>Caretaker | <B><br>my<br>Father<br>or Male<br>Caretaker | <C><br>Another<br>Person who<br>affected<br>my life |
|---|---|---|---|

*Please answer the following about your relationships with others when you were growing up.*

8. The amount of HUMOR, ENJOYMENT, and HAPPINESS shown by this person:

{ 1 } *TOO LITTLE* .......................................................... [ 1A ]  [ 1B ]  [ 1C ]
    This person was usually either:
    • *TOO* SERIOUS, DULL, UNHAPPY, TENSE, or EASILY UPSET;
    • almost NEVER HAD FUN or LAUGHED { 2 } *TOO MUCH* ........................................................... [ 2A ]  [ 2B ]  [ 2C ]
    This person was usually either:
    • *TOO* SILLY or FOOLISH;
    • almost NEVER TOOK ANYTHING SERIOUSLY { 3 } *INCONSISTENT* ....................................................... [ 3A ]  [ 3B ]  [ 3C ]
    This person was: very *INCONSISTENT*; one day HAPPY or HAVING FUN and the next day UPSET or UNHAPPY { 4 } *A GOOD AMOUNT* ..................................................... [ 4A ]  [ 4B ]  [ 4C ]
    This person was usually PLEASANT, ENJOYABLE, ABLE TO LAUGH and FOOL AROUND, but he/she could be SERIOUS WHEN NECESSARY

OTHER IMPORTANT INFORMATION ABOUT DIFFERENT PEOPLE

*When I was growing up, this person...*

9. was mostly ABSENT FROM MY LIFE .......................................... [ A ]  [ B ]  [ C ]
10. EMOTIONALLY ABUSED me .................................................. [ A ]  [ B ]  [ C ]
11. PHYSICALLY or SEXUALLY ABUSED people in my family ...................... [ A ]  [ B ]  [ C ]
12. EMOTIONALLY ABUSED other people in my family ........................... [ A ]  [ B ]  [ C ]
13. was in serious TROUBLE with the LAW .................................... [ A ]  [ B ]  [ C ]
14. let ALCOHOL or DRUG USE cause serious problems ......................... [ A ]  [ B ]  [ C ]
15. DIED NON-VIOLENTLY while relatively YOUNG .............................. [ A ]  [ B ]  [ C ]
16. DIED VIOLENTLY (other than Suicide) .................................... [ A ]  [ B ]  [ C ]
17. KILLED HIM/HERSELF (committed SUICIDE) ................................. [ A ]  [ B ]  [ C ]
18. was seriously PHYSICAL DISABLED or ILL ................................. [ A ]  [ B ]  [ C ]
19. had serious EMOTIONAL problems ......................................... [ A ]  [ B ]  [ C ]
20. had serious LEARNING problems .......................................... [ A ]  [ B ]  [ C ]

OTHER ISSUES ABOUT MY PAST

Please answer the following about your life when you were growing up. Mark the boxes that are MOSTLY TRUE.

*When I was growing up, I often felt:*

21. DIFFERENT, LONELY or like I DIDN'T FIT IN with my peers ........................ [ ]
22. UNWANTED, UNLOVABLE or UNDESIRABLE ................................. [ ]
23. very FEARFUL, WORRIED or ANXIOUS ...................................... [ ]
24. very ANGRY ................................................................. [ ]
25. very SAD or DEPRESSED ................................................... [ ]
26. very ASHAMED or EMBARRASSED ......................................... [ ]
27. very GUILTY ................................................................ [ ]
28. very JEALOUS or ENVIOUS of certain people ................................. [ ]

*When I was growing up, there was a rather long period of time during which I believed that:*

29. I was UNATTRACTIVE (UGLY, FUNNY-LOOKING) ............................ [ ]
30. I was INTELLECTUALLY INFERIOR (UNINTELLIGENT, STUPID) ................ [ ]
31. I was PHYSICALLY INFERIOR (WEAK, UNCOORDINATED) ..................... [ ]
32. I was ECONOMICALLY INFERIOR (POOR, LOW SOCIAL CLASS) ................ [ ]

*When I was growing up:*

33. I was very OVERWEIGHT .................................................... [ ]
34. I was very UNDERWEIGHT ................................................... [ ]
35. I was BULIMIC or ANOREXIC ................................................ [ ]
36. I had a DRINKING or DRUG ABUSE PROBLEM ................................ [ ]
37. I had SERIOUS MEDICAL or PHYSICAL PROBLEMS ........................... [ ]
38. I had SERIOUS EMOTIONAL PROBLEMS ...................................... [ ]
39. I tried to KILL MYSELF ..................................................... [ ]
40. I had been HOSPITALIZED for EMOTIONAL PROBLEMS ...................... [ ]
41. I RAN AWAY FROM HOME for a long time .................................... [ ]
42. I did things that got me into serious TROUBLE WITH THE LAW ................ [ ]
43. I was very CONFUSED about my SEXUAL IDENTITY .......................... [ ]
44. If you are Adopted: I was VERY UPSET ABOUT MY ADOPTION ................ [ ]

*I sometimes regret that:*

45. I was a TEENAGE PARENT ................................................... [ ]
46. I DROPPED OUT of SCHOOL ................................................. [ ]
47. I had an ABORTION ......................................................... [ ]

What is claimed is:

1. In an apparatus for processing psychological data, said apparatus comprising means for processing data indicative of at least one of an individual's psychological condition, psychological states, concomitant physiological states, states of dysfunction, a health care provider and a health care payer, in conjunction with at least one of psychological, concomitant physiological, and psychopathological, at least one of principles, theories and research data in order to generate output data indicative of at least one of psychological states, concomitant physiological states, states of dysfunction, psychological profile, diagnosis, treatment goals, individual to provider matching, a treatment plan, a treatment outcome, a treatment process, a treatment progress, a health care provider and a health care payer, related to an individual, the improvement comprising:

a remote user interactive means for providing at least one of a remote accessing and utilization of said apparatus, said remote user interactive means further comprising:

a user input means for inputting data pertaining to an individual; and a user display means for providing at least one of an indication of apparatus operation and data relevant to an individual;

wherein said remote user interactive means facilitates at least one of data entry and control over said apparatus, and further wherein said output data indicative of at least one of psychological states, concomitant physiological states, states of dysfunction, psychological profile, diagnosis, treatment goals, individual to provider matching, a treatment plan, a treatment process, a treatment outcome, a treatment progress, a health care provider and a health care payer, related to an individual, is obtained at said remote user interactive means.

2. The improved apparatus of claim 1, further comprising:
a communication means for linking said remote user interactive means to said apparatus.

3. The improved apparatus of claim 1, wherein said user input means comprises at least one of a keyboard, a scanner, and a modem.

4. The improved apparatus of claim 1, further comprising:
a user output device for outputting said output data in a form useful for a user.

5. The improved apparatus of claim 1, further comprising:
a means for storing said output data indicative of at least one of psychological states, concomitant physiological states, states of dysfunction, psychological profile, diagnosis, treatment goals, individual to provider matching, a treatment plan, a treatment process, a treatment outcome, a treatment progress, a health care provider and a health care payer, related to an individual.

6. The improved apparatus of claim 1, further comprising:
a means for securing said output data indicative of at least one of psychological states, concomitant physiological states, states of dysfunction, psychological profile, diagnosis, treatment goals, individual to provider matching, a treatment plan, a treatment process, a treatment outcome, a treatment progress, a health care provider and a health care payer, related to an individual, against unauthorized access.

7. The improved apparatus of claim 1, further comprising:
a means for one of analyzing and comparing said output data indicative of at least one of psychological states, concomitant physiological states, states of dysfunction, psychological profile, diagnosis, treatment goals, individual to provider matching, a treatment plan, a treatment process, a treatment outcome, a treatment progress, a health care provider and a health care payer, related to an individual, for a plurality of individuals.

8. In an apparatus for processing psychological data, said apparatus comprising means for processing data indicative of at least one of an individual's psychological condition, psychological states, concomitant physiological states, and states of dysfunction, in conjunction with at least one of psychological, concomitant physiological, and psychopathological, at least one of principles, theories and research data in order to generate output data indicative of at least one of a diagnosis and a treatment plan for the individual, the improvement comprising:

a remote user interactive means for providing at least one of a remote accessing and utilization of said apparatus, said remote user interactive means further comprising:

a user input means for inputting data pertaining to the individual; and a user display means for providing at least one of an indication of apparatus operation and data relevant to the individual;

wherein said remote user interactive means facilitates at least one of data entry and control over said apparatus, and further wherein said output data pertinent to at least one of an individual's diagnosis and treatment plan is obtained from said apparatus via said remote user interactive means.

9. The improved apparatus of claim 8, further comprising:
a communication means for linking said remote user interactive means to said apparatus.

10. The improved apparatus of claim 8, wherein said user input means comprises at least one of a keyboard, a scanner, and a modem.

11. The improved apparatus of claim 8, further comprising:
a user output device for outputting said output data in a form useful for a user.

12. The improved apparatus of claim 8, further comprising:
a means for storing said output data indicative of at least one of a diagnosis and a treatment plan for an individual.

13. The improved apparatus of claim 8, further comprising:
a means for securing said output data indicative of at least one of a diagnosis and a treatment plan for an individual against unauthorized access.

14. The improved apparatus of claim 8, wherein said communication means is at least one of a telecommunication means, a radio communication means and a satellite communication means.

15. A method for remotely utilizing an apparatus for processing psychological data, said apparatus comprising means for processing data indicative of at least one of an individual's psychological condition, psychological states, concomitant physiological states, states of dysfunction, a health care provider and a health care payer, in conjunction with at least one of psychological, concomitant physiological, and psychopathological, at least one of principles, theories and research data in order to generate output data indicative of at least one of psychological states, concomitant physiological states, states of dysfunction, psychological profile, diagnosis, treatment goals, individual to provider matching, a treatment plan, a treatment outcome, a treatment process, a treatment progress, a health care provider and a health care payer, related to an individual, said method comprising the steps of:

accessing said apparatus at a location remote from said apparatus;

entering input data indicative of at least one of an individual's psychological condition, psychological states, concomitant physiological states and states of dysfunction, via a user input device;

transmitting said input data to said apparatus;

processing said input data at said apparatus; and receiving output data from said apparatus, wherein said output data is indicative of at least one of psychological states, concomitant physiological states, states of dysfunction, psychological profile, diagnosis, treatment goals, individual to provider matching, a treatment process, treatment outcome, a treatment process, a treatment progress, related to an individual, at said remote location.

16. The method of claim 15, further comprising the step of:

one of inspecting and analyzing said output data indicative of at least one of psychological states, concomitant physiological states, states of dysfunction, psychological profile, diagnosis, treatment goals, individual to provider matching, a treatment plan, a treatment outcome, a treatment process, a treatment progress, related to an individual, at said remote location.

17. The method of claim 15, further comprising the step of:

outputting at least a portion of said output data at said remote location.

18. The method of claim 15, further comprising the step of:

storing said output data received from said apparatus at said remote location.

19. The method of claim 18, further comprising the step of:

one of analyzing and comparing said output data for a plurality of individuals.

20. The method of claim 15, further comprising the step of:

securing said output data against unauthorized access.

* * * * *